United States Patent
Sternberg et al.

(10) Patent No.: US 6,723,557 B1
(45) Date of Patent: Apr. 20, 2004

(54) CAENORHABDITIS ELEGANS LOV-1 GENE

(75) Inventors: Paul W. Sternberg, Pasadena, CA (US); Maureen M. Barr, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 09/479,467

(22) Filed: Jan. 6, 2000

Related U.S. Application Data

(60) Provisional application No. 60/115,127, filed on Jan. 6, 1999.

(51) Int. Cl.⁷ .................. C12N 15/00; C12N 15/09; C12N 15/63; C12N 15/70; C12N 15/74

(52) U.S. Cl. .................. 435/320.1; 536/23.1; 536/23.5; 800/13

(58) Field of Search .................. 435/320.1, 325, 435/455; 536/23.1, 23.5, 23.9; 800/13, 3; 530/356

(56) References Cited

U.S. PATENT DOCUMENTS

| | | | |
|---|---|---|---|
| 4,568,639 A | 2/1986 | Lew | 435/68 |
| 4,756,908 A | 7/1988 | Lew | 424/88 |
| 5,196,333 A | 3/1993 | Chalfie et al. | 435/240.1 |
| 5,472,871 A | 12/1995 | Wood et al. | 435/252.3 |
| 5,559,026 A | 9/1996 | Price et al. | 435/254.2 |
| 5,741,668 A | 4/1998 | Ward et al. | 435/69.1 |
| 5,789,189 A | 8/1998 | Woo | 435/30 |
| 5,840,540 A | 11/1998 | St. George-Hyslop et al. | 435/69.1 |
| 5,891,628 A | 4/1999 | Reeders et al. | 435/6 |
| 5,929,207 A | 7/1999 | Horvitz et al. | 530/324 |
| 5,962,301 A | 10/1999 | Horvitz et al. | 435/226 |
| 5,972,882 A | 10/1999 | Gattone, II | 514/11 |
| 5,985,830 A | 11/1999 | Acott et al. | 514/12 |
| 5,986,054 A | 11/1999 | St. George-Hyslop et al. | 530/350 |

FOREIGN PATENT DOCUMENTS

| | | |
|---|---|---|
| WO | 9534573 | 12/1995 |
| WO | 9638555 | 12/1996 |
| WO | 9937770 | 7/1999 |

OTHER PUBLICATIONS

Wilson et al, 1994, Nature, 368: 32–38.*
Ebert et al, 1988, Mol. Endocrin., 2: 277–283.*
Hammer et al, 1986, J. Animal Sci., 63: 269–278.*
Houdebine et al, 1994, J. of Biotech, 34: 269–287.*
Kappel et al, 1992, Cur. Opin. Biotech., 3: 548–553.*
Mullins et al, 1996, J. Clin. Invest., 98(11): S37–40.*
Strojek et al, 1988, Genetic Engineering: Prin. and Meth., 10: 221–246.*
Wall et al, 1996, Theriogenology, 45: 57–68.*
Barr et al., A polycystic kidney–disease gene homologue required for male mating behaviour in *C. elegans, Nature*, 401:386–389 (1999).
Bronner–Fraser, M. and P.W. Sternberg, Pattern formation and development mechanisms: The cell biological basis of inductive signaling, *Curr. Opin. Genet. Dev.* 10:347–9 (2000).
Chang et al., *Caenorhabditis elegans* SOS–1 is necessary for multiple RAS–mediated developmental signals, *The EMBO Journal* 19(13):3283–94 (2000).
Chang et al., *C. elegans* vulval development as a model system to study the cancer biology of EGFR signaling, *Cancer and Metastasis Reviews* 18:203–13 (1999).
Database Embl Nucleotide and Protein Sequences, Nov. 1, 1996, XP002140195 Hinxton, GB AC=Q21027, Similar to Glycoproteins, F59A6.3. *Caenorhabditis elegans* abstract.
Database Embl Nucleotide and Protein Sequences, Mar. 1, 1995, XP002140194 Hinxton, GB AC=Z48544, *Caenorhabditis elegans* cosmid ZK945. Polysystic kidney disease protein 1. From nt 24444 to nt 25742.
Database Embl Nucleotide and Protein Sequences, Nov. 9, 1999, XP002140196 Hinxton, GB AC=AL132862. *Caenorhabditis elegans* cosmid Y73F8A. From nt 1605–9677.
Felix et al., Evolution of Vulva Development in the *Cephalobina* (Nematoda), *Developmental Biology* 221:68–86 (2000).
Gabow et al. Polycystic Kidney Disease, *Diseases of the Kidney* Schrier, R.W. and C.W. Gottschalk (eds.) 1993.
Hopper et al., ARK–1 Inhibits EGFR Signaling in *C. elegans, Molecular Cell*, 6:65–75 (2000).
*Methods in Cell Biology* vol. 48: *Caenorhabditis elegans: Modern Biological Analysis of an Organism*. Epstein, H.F. and D.C. Shakes (eds.) Academic Press, Inc. 1995.
Newman et al., Morphogenesis of the *C. elegans* hermaphrodite uterus, *Development* 122(11):3617–3626 (1996).

(List continued on next page.)

*Primary Examiner*—Peter Paras
(74) *Attorney, Agent, or Firm*—Gray Cary Ware & Freidenrich, LLP

(57) ABSTRACT

Nematodes, such as *Caenorhabditis elegans*, that express mutant and wild-type orthologs of human genes involved in polycystic kidney diseases (PKDs), are used to study the functions of the proteins encoded by the genes, to screen for other genes involved in the diseases, to identify mutations involved in the diseases, and to screen for drugs that affect PKD. Behaviors controlled by the action of the genes or gene products are identified and used in the assays. Hence an animal model is provided that permits study of the etiology of polycystic kidney disease and provides a tool to identify the genes involved in the disease pathway, and to identify compounds that may be used to treat or alter the disease progression, lessen its severity or ameliorate symptoms. The nematode genes that encode protein products, mutants of the genes, vectors contain the genes and mutant genes and nematode strains that contain the vectors are also provided.

6 Claims, 6 Drawing Sheets

OTHER PUBLICATIONS

Newman et al., The *Caenorhabditis elegans* heterochronic gene lin–29 coordinates the vulval–uterine–epidermal connections, *Curr. Biol.* 10:1479–88 (2000).
Newman et al., The lin–11 LIM domain transcription factor is necessary for morphogenesis of *C. elegans* uterine cells, *Development* 126(23):5319–26 (1999).
Sambrook et al. (1989) *Molecular Cloning: A Laboratory Manual*, 2nd ed. Cold Spring Harbor Laboratory Press, Cold Spring Harbor, NY.
Shim et al., Distinct and Redundant Functions of u1 Medium Chains of the AP–1 Clathrin–Associated Protein Complex in the Nematode *Caenorhabditis elegans, Molecular Biology* 11:2743–56 (2000).
Sternberg et al., Intercellular Signaling and Signal Transduction in *C. elegans, Annu. Rev. Genet.* 27:497–521 (1993).
Wang et al., Patterning of the *C. elegans* 1 degree vulval lineage by RAS and Wnt pathways, *Development* 127:5047–58 (2000).
Yoon et al., Requirements of Multiple Domains of SLI–1, a *Caenorhabditis elegans* Homologue of c–Cbl, and an Inhibitory Tyrosine in LET–23 in Regulating Vulvsl Differentiation, *Molecular Biology of the Cell* 11:4019–31 (2000).
Database EMBL Nucleotide and Protein Sequences, XP002140194, *C. elegans* cosmid ZK945, Mar. 1, 1995.
Database EMBL Nucleotide and Protein Sequences, XP002140196, *C. elegans* cosmid Y73F8A, Nov. 9, 1999.
Database EMBL Nucleotide and Protein Sequences, XP002140195, Similar to Glycoproteins, F59A6.3, Nov. 1, 1996.
Aroian et al., Mutations in the *Caenorhabditis elegans* let–23 EGFR–like gene define elements of important for cell–type specificity and function, *The EMBO Journal* 13(2):360–366 (1994).
Aroian et al., Multiple Functions of let–23, a *Caenorhabditis elegans* Receptor Tyrosine Kinase Gene Required for Vulval Induction, *Genetics* 128:251–267 (1991).
Bargmann, Neurobiology of the *Caenorhabditis elegans* Genome, *Science* 282:2028–2033 (1998).
Barr et al., A polycystic kidney–disease gene homologue required for male mating behaviour in *C. elegans, Nature* 401:386–389 (1999).
Brenner, The Genetics of *Caenorhabditis Elegans, Genetics* 77:71–94 (1974).
Brundage et al., Mutations of *C. elegans* $G_q\alpha$ Gene Disrupt Movement, Egg Laying, and Viability, *Neuron* 16(5):999–1009 (1996).
Carraway et al., Mucin Structure and Function: Insights from Molecular Biology, *Trends in Glycoscience and Glycotechnology* 7(33):31–44 (1995).
Chalfie et al., Green Fluorescent Protein as a Marker for Gene Expression, *Science* 263:802–805 (1994).
Chamberlin et al., Multiple cell interactions are required for fate specification during male spicule development in *Caenorhabditis elegans, Development* 118(2):297–324 (1993).
Chamberlin et al., Characterization of Seven Genes Affecting *Caenorhabditis elegans* Hindgut Development, *Genetics* 153(2):731–742 (1999).
Chamberlin et al., The PAX gene egl–38 mediates developmental patterning in *Caenorhabditis elegans, Development* 124(20):3919–3928 (1997).
Chamberlin et al., The lin–3/let–23 pathway mediates inductive signalling during male spicule development in *Caenorhabditis elegans, Development* 120:2713–2721 (1994).

Chang et al., Reciprocal EGF signaling back to the uterus from the induced *C. elegans* vulva coordinates morphogenesis of epithelia, *Current Biology* 9(5):237–246 (1999).
Chen et al., Polycystin–L is a calcium–regulated cation channel permeable to calcium ions, *Nature* 401:383–386 (1999).
Clandinin et al., Inositol Triphosphate Mediates a RAS–Independent Response to LET–23 Receptor Tyrosine Kinase Activation in *C. elegans, Cell* 92(4):523–533 (1998).
Clandinin et al., *Caenorhabditis elegans* HOM–C genes Regulate the Response of Vulval Precursor Cells to Inductive Signal, *Developmental Biology* 182(1):150–161 (1997).
Collet et al., Analysis of osm–6, a Gene That Affects Sensory Cilium Structure and Sensory Neuron Function in *Caenorhabditis elegans, Genetics* 148:187–200 (1998).
Daoust et al., Evidence for a Third Genetic Locus for Autosomal Dominant Polycystic Kidney Disease, *Genomics* 25:733–736 (1995).
Driscoll et al., Mechanotransduction, *C. elegans II,* pp. 645–677 (1997).
Emmons et al., Mating, channels and kidney cysts, *Nature*, 401:339–340 (1999).
Felix et al., Symmetry breakage in the development of one–armed gonads in nematodes, *Development* 122(7):2129–2142 (1996).
Felix et al., A gonad–derived survival signal for vulval precursor cells in two nematode species, *Curr. Biol.* 8(5):287–290 (1998).
Ferguson et al., A genetic pathway for the specification of the vulval cell lineages of *Caenorhabditis elegans, Nature* 326:259–267 (1987).
Gabow, Autosomal Dominant Polycystic Kidney Diseases—More Than a Renal Disease, *American Journal of Kidney Diseases* 16(5):403–413 (1990).
Germino et al., The Gene for Autosomal Dominant Polycystic Kidney Disease Lies in a 750–kb CpG–Rich Region, *Genomics* 13:144–151 (1992).
Golden et al., The Roles of SH2/SH3 Domains in Nematode Development, *Bioassays* 14(7):481–484 (1992).
Hajdu–Cronin et al., Antagonism between $G_o\alpha$ and $G_q\alpha$ in *Caenorhabditis elegans:* the RGS protein EAT–16 is necessary for $G_o\alpha$ signaling and regulates $G_q\alpha$ activity, *Genes & Development* 13(14):1780–1793 (1999).
Han et al., *C. elegans* lin–45 raf gene participates in let–60 ras–stimulated vulval differentiation, *Nature* 363(6426):133–140 (1993).
Han et al., The let–60 Locus Controls the Switch Between Vulval and Nonvulval Cell Fates in *Caenorhabditis elegans, Genetics* 126:899–913 (1990).
Han et al., Analysis of dominant–negative mutations of the *Caenorhabditis elegans* let–60 ras gene, *Genes & Development* 5(12A):2188–2198 (1991).
Herskowitz, Functional inactivation of genes by dominant negative mutations, *Nature* 329:219–222 (1987).
Hill et al., The gene lin–3 encodes an inductive signal for vulval development in *C. elegans, Nature* 358(6386):470–476 (1992).
Hill et al., Cell fate patterning during *C. elegans* vulval development, *Development* pp. 9–18 (1993).
Himmelbauer et al., Human–Mouse Homologies in the Region of the Polycystic Kidney Disease Gene (PKD1), *Genomics* 13:35–38 (1992).
Hodgkin, Male Phenotypes and Mating Efficiency in *Caenorhabditis elegans, Genetics* 103:43–64 (1983).

Hodgkin, Sexual Dimorphism and Sex Determination, *The Nematode C. elegans,* pp. 243–279 (1988).

Hoffmann et al., Learning about cancer genes through invertebrate genetics, *Curr. Opin. Genet. Dev.* 2(1):45–52 (1992).

Horvitz et al., Multiple intercellular signalling systems control the development of the *Caenorhabditis elegans* vulva, *Nature* 351:535–541 (1991).

Hsieh et al., The RING finger/B–box factor TAM–1 and a retinoblastoma–like protein LIN–35 modulate context–dependent gene silencing in *Caenorhabditis elegans, Genes & Development* 13(22):2958–70 (1999).

Huang et al., Genetic Dissection of Developmental Pathways, *Methods Cell Biol.* 48:97–122 (1995).

Huang et al., The lin–15 Locus Encodes Two Negative Regulators of *Caenorhabditis elegans* Vulval Development, *Molecular Biology of the Cell* 5:395–412 (1994).

Hudspeth, How the ear's works work, *Nature* 341:397–404 (1989).

Hughes et al., The polycystic kidney disease 1 (PKD1) gene encodes a novel protein with multiple cell recognition domains, *Nature Genetics* 10:151–161 (1995).

Hughes et al., Identification of a human homologue of the sea urchin receptor for egg jelly: a polycystic kidney disease–like protein, *Human Molecular Genetics* 8(3):543–549 (1999).

Jiang et al., An HMG1–like protein facilitates Wnt signaling in *Caenorhabditis elegans, Genes & Developmental* 13(7):877–889 (1999).

Jiang et al., Interactions of EGF, Wnt and HOM–C genes specify the P12 neuroectoblast fate in *C. elegans, Development,* 125(12):2337–2347 (1998).

Jiang et al., Socket Cells Mediate Spicule Morphogenesis in *Caenorhabditis elegans* Males, *Development Biology* 211(1):88–99 (1999).

Jongeward et al., sli–1, a Negative Regulator of let–23–Mediated Signaling in *C. elegans, Genetics,* 139(4):1553–1556 (1995).

Kaplan et al., A dual mechanosensory and chemosensory neuron in *Caenorhabditis elegans, Proc. Natl. Acad. Sci. USA* 90:2227–2231 (1993).

Katz et al., A plethora of intercellular signals during *Caenorhabditis elegans* development, *Curr. Opin. Cell Biol.* 4(6):939–947 (1992).

Katz et al., Different Levels of the *C. elegans* Growth Factor LIN–3 Promote Distinct Vulval Precursor Fates, *Cell* 82(2):297–307 (1995).

Katz et al., A Point Mutation in the Extracellular Domain Activates LET–23, the *Caenorhabditis elegans* Epidermal Growth Factor Receptor Homolog, *Mol. Cell. Biol.* 16(2):529–537 (1996).

Kayne et al., Ras pathways in *Caenorhabditis elegans, Curr. Opin. Genet. Dev.* 5(1):38–43 (1995).

Kimberling et al., Autosomal Dominant Polycystic Kidney Disease: Localization of the Second Gene to Chromosome 4q13–q23, *Genomics* 18:467–472 (1993).

Lee et al., unc–101, a gene required for many aspects of *Caenorhabditis elegans* development and behavior, encodes a clathrin–associated protein, *Genes & Development* 8:60–73 (1994).

Lesa et al., Positive and Negative Tissue–specific Signaling by a Nematode Epidermal Growth Factor Receptor, *Mol. Biol. Cell* 8(5):779–793 (1997).

Liu et al., Sensory Regulation of Male Mating Behavior in *Caenorhabditis elegans, Neuron* 14:79–89 (1995).

McDonald et al., Inherited Polycystic Kidney Disease in Children, *Seminars in Nephrology* 11(6):632–642 (1991).

Mendel et al., Participation of the Protein $G_o$ in Multiple Aspects of Behavior in *C. elegans, Science* 267(5204):1652–1655 (1995).

Mochizuki et al., PKD2, a Gene for Polycystic Kidney Disease That Encodes an Integral Membrane Protein, *Science* 272:1339–1342 (1996).

Montell et al., Molecular Characterization of the Drosophila trp Locus: A Putative Integral Membrane Protein Required for Phototransduction, *Neuron* 2:1313–1323 (1989).

Mori et al., The identification of a *Caenorhabditis elegans* homolog of $p34^{cdc2}$ kinase, *Mol. Gen. Genet.* 245:781–786 (1994).

Newman et al., The lin–11 LIM domain transcription factor is necessary for morphogenesis of *C. elegans* uterine cells, *Development* 126(23):5319–26 (1999).

Newman et al., Coordinated morphogenesis of epithelia during development of the *Caenorhabditis elegans* uterine––vulval connection, *Proc. Natl. Acad. Sci. USA* 93(18):9329–9333 (1996).

Newman et al., The *Caenorhabditis elegans* lin–12 gene mediates induction of ventral uterine specialization by the anchor cell, *Development* 121(2):263–271 (1995).

Newman et al., Morphogenesis of the *C. elegans* hermaphrodite uterus, *Development* 122(11):3617–3626 (1996).

Nomura et al., Identification of PKDL, a Novel Polycystic Kidney Disease 1–Like Gene Whose Murine Homologue Is Deleted in Mice with Kidney and Retinal Defects, *J. Biol. Chem.* 273(40):25967–25973 (1998).

Perkins et al., Mutant Sensory Cilia in the Nematode *Caenorhabditis elegans, Developmental Biology* 117:456–487 (1986).

Qian et al., PKD1 interacts with PKD2 through a probable coiled–coil domain, *Nature Genetics* 16:179–183 (1997).

Reeders et al., A highly polymorphic DNA marker linked to adult polycystic kidney disease on chromosome 16, *Nature* 317:542–544 (1985).

Schnabel et al., An Organ–Specific Differentiation Gene, pha–1, from *Caenorhabditis elegans, Science* 250:686–688 (1990).

Scott et al., TRP, TRPL and trouble in photoreceptor cells, *Current Opinion in Neurobiology* 8:383–388 (1998).

Somlo et al., Fine Genetic Localization of the Gene for Autosomal Dominant Polycystic Kidney Disease (PKD1) with Respect to Physically Mapped Markers, *Genomics* 13:152–158 (1992).

Sommer et al., Changes of Induction and Competence During the Evolution of Vulva Development in Nematodes, *Science* 265:114–118 (1994).

Sommer et al., Apoptosis and change of competence limit the size of the vulva equivalence group in *Pristionchus pacificus:* a genetic analysis, *Current Biology* 6(1):52–59 (1996).

Sommer et al., Evolution of Nematode Vulval Fate Patterning, *Developmental Biology* 173(2):396–407 (1996).

Sternberg et al., Role of a raf proto–oncogene during *Caenorhabditis elegans;* vulval development, *Phil. Trans. R. Soc. Lond. B. Biol. Sci.* 340(1293):259–265 (1993).

Sternberg et al., Molecular Genetics of Proto–oncogenes and Candidate Tumor Suppressors in *Caenorhabditis elegans, Cold Spring Harb. Symp. Quant. Biol.* 59:155–163 (1994).

Sternberg, Control of cell fates within equivalence groups in *C. elegans, TINS,* 11(6):259–264 (1988).

Sternberg et al., Intracellular Signaling and Signal Transduction in *C. elegans, Annu. Rev. Genet.* 27:497–521 (1993).

Sternberg et al., lin–17 Mutations of *Caenorhabditis elegans* Disrupt Certain Asymmetric Cell Divisions, *Developmental Biology* 130:67–73 (1988).

Sternberg et al., Genetics of RAS signaling in *C. elegans, TIG* 14(11):466–472 (1998).

Sternberg et al., LET–23–Mediated Signal Transduction During *Caenorhabditis elegans* Development, *Mol. Reprod. Dev.* 42(4):523–528 (1995).

Sulston et al., The *Caenorhabditis elegans* Male: Postembryonic Development of Nongonadal Structures, *Developmental Biology* 78:542–576 (1980).

The *C. elegans* Sequencing Consortium, Genome Sequence of the Nematode *C. elegans:* A Platform for Investigating Biology, *Science* 282:2012–2018 (1998).

Torres et al., New insights into polycystic kidney disease and its treatment, *Current Opinion in Nephrology and Hypertension* 7:159–169 (1998).

Tsiokas et al., Homo– and heterodimeric interactions between the gene products of PKD1 and PKD2, *Proc. Natl. Acad. Sci. USA* 94:6965–6970 (1997).

Wang et al., Competence and Commitment of *Caenorhabditis elegans* Vulval Precursor Cells, *Developmental Biology* 212(1):12–24 (1999).

Ward et al., Electron Microscopical Reconstruction of the Anterior Sensory Anatomy of the Nematode *Caenorhabditis elegans, J. Comp. Neur.* 160:313–337 (1975).

Watson et al., The Fine Structure of Bacterial and Phage Genes, *Molecular Biology of the Gene,* 4th Edition, p. 224 (1987).

White et al., The Structure of the Nervous System of the Nematode *Caenorhabditis Elegans, Phil. Trans. R. Soc. Lond. B* 314:1–67 (1986).

Yoon et al., Similarity of sli–1, a Regulator of Vulval Development in *C. elegans,* to the Mammalian Proto–Oncogene c–cbl, *Science* 269(5227):1102–1105 (1995).

Zerres et al., Mapping of the gene for autosomal recessive polycystic kidney disease (ARPKD) to chromosome 6p21–cen, *Nature Genetics* 7:429–432 (1994).

Zhen et al., The liprin protein SYD–2 regulates the differentiation of presynaptic termini in *C. elegans, Nature* 401:371–375 (1999).

Zwaal et al., Two Neuronal G Proteins are Involved in Chemosensation of the *Caenorhabditis elegans* Dauer–Inducing Pheromone, *Genetics* 145(3):715–727 (1997).

* cited by examiner

A. *lov-1(sy552)* rescue data

B. *lov-1* gene structure: 16.7 kb rescuing clone

C. Schematic of GFP fusion constructs and expression data

D. LOV-1 structural features and sequence homologies

CAENORHABDITIS ELEGANS LOV-1 GENE

RELATED APPLICATIONS

For U.S. purposes, benefit of priority under 35 U.S.C. §119(e) to U.S. Provisional Application Serial No. 60/115,127, entitled "CAENORHABDITIS ELEGANS STRAINS PERTURBED IN POLYCYSTIN FUNCTION" to Paul W. Sternberg and Maureen M. Barr, filed Jan. 6, 1999, is claimed herein. The subject matter of U.S. Provisional Application Serial No. 60/115,127 is incorporated in its entirety by reference.

FIELD OF INVENTION

Systems and assays for identification of compounds that can be used to treat polycystic kidney disease (PKD) are provided. Nematode orthologs of genes involved in PKD are identified and associated with mating behaviors. In particular, nematodes, such as Caenorhabditis elegans, that express mutant and wild-type orthologs of human genes involved in this disease, are used to study the functions of the proteins encoded by the genes, to screen for other genes involved in the disease, to identify mutations involved in the disease, and to screen for drugs that affect PKD. Hence an animal model is provided that permits study of the etiology of polycystic kidney disease and provides a tool to identify the genes and factors involved in the disease pathway, and to identify compounds that may be used to treat or alter the disease progression, lessen its severity or ameliorate symptoms.

BACKGROUND
Polycystic Kidney Diseases

Polycystic kidney diseases (PKD) are a group of disorders characterized by the presence of a large number of fluid-filled cysts throughout grossly enlarged kidneys (Gabow et al. (1992) *Diseases of the Kidney*, Schrier et al. eds.). In humans, PKDs can be inherited in autosomal dominant (ADPKD) or autosomal recessive (ARPKD) forms. ADPKD is the more common form and is the most common, dominantly-inherited kidney disease in humans, occurring at a frequency of about 1 in 800. ARPKD occurs at a frequency of about 1 in 10,000.

ADPKD is the most common single-gene disorder leading to kidney failure (see, Emmons et al. (1999) *Nature* 401:339–340). Since ADPKD is inherited as an autosomal dominant disorder, children of affected parents have a one in two chance of inheriting the disease. Although the kidney is the most severely affected organ, the disease is systemic and affects the liver, pancreas cardiovascular system and cerebro-vascular system. The major manifestation of the disorder is the progressive cystic dilation of renal tubules (Gabow (1990) *Am. J. Kidney Dis.* 16:403–413), leading to renal failure in half of affected individuals by age 50. Microdissection, histochemical and immunologic studies show that cysts in ARPKD kidneys arise from focal dilations of medullary collecting ducts (McDonald (1991) *Semin. Nephrol.* 11:632–642). Although end-stage renal failure usually supervenes in middle age (ADPKD is sometimes called adult polycystic kidney disease), children may occasionally have severe renal cystic disease.

ADPKD-associated renal cysts may enlarge to contain several liters of fluid and the kidneys usually enlarge progressively causing pain. Other abnormalities such as hematuria, renal and urinary infection, renal tumors, salt and water imbalance and hypertension frequently result from the renal defect. Cystic abnormalities in other organs, including the liver, pancreas, spleen and ovaries are commonly found in ADPKD. Massive liver enlargement can causes portal hypertension and hepatic failure. Cardiac valve abnormalities and an increased frequency of subarachnoid and other intracranial hemorrhage have also been observed in ADPKD. Progressive renal failure causes death in many ADPKD patients and dialysis and transplantation are frequently required to maintain life in these patients.

Numerous biochemical abnormalities associated with this disease also are observed. These include defects in protein sorting, the distribution of cell membrane markers within renal epithelial cells, extracellular matrix, ion transport, epithelial cell turnover, and epithelial cell proliferation.

Three distinct loci have been shown to cause phenotypically indistinct forms of the AKPKD in humans. These include polycystin-1 (PKD1) on chromosome 16, polycystin-2 (PKD2) on chromosome 4, and polycystin-3 (PKD3) (see, e.g., Reeders et al. (1985) *Nature* 317:542–544; Kimberling et al. (1993) *Genomics* 18:467–472; Daoust et al. (1995) Genomics, 25:733–736). The ARPKD mutation is on human chromosome 6 (Zerres et al. (1993) *Nature Genet.* 7:429–432). Two proteins polycystin-1 (PKD1) and polycystin-2 (PKD2) are defective in human autosomal dominant polycystic kidney disease.

Mutations in either PKD1 or PKD2 cause almost indistinguishable clinical symptoms. Mutations in PKD1 or PKD2 account for 95% of autosomal dominant polycystic disease (Torres et al. (1998) Current Opinion in Nephrology and *Hypertension* 7:159–169) with greater than 85–90% of disease incidence being due to mutations in PKD1.

The human PKD1 protein is an approximately 4,300 amino-acid integral-membrane glycoprotein with a large amino-terminal extracellular domain and a small, carboxy-terminal cytoplasmic tail. The human PKD1 gene (see, e.g., U.S. Pat. No. 5,891,628), including the complete nucleotide sequence of the gene's coding region (se SEQ ID No. 1) and encoded amino acid sequence, is known (see, SEQ ID No. 2). The predicted structure of the domains suggested that it is involved in cell-cell interactions or in interactions with the extracellular matrix. The PKD2 protein has similarities to PKD1, but its topology and domain structure suggest that it might act as a subunit of a cation channel. These proteins have been shown to interact directly (Mochizuki et al. (1996) *Science* 272:1339–1342, Qian (1997) *Nature Genetics* 16:179–183).

Although these genes have been implicated in the disorders their role in it etiology is not established. In addition, while studies of kidneys from ADPKD patients exhibit a number of different biochemical, structural and physiological abnormalities, the disorder's underlying causative biochemical defect is not known. Hence the molecular mechanisms leading to cyst enlargement and progressive loss of renal function in the PKDs are not understood. Presently there are no cures or effective treatments, other than palliative treatments, for these diseases. Hence there is a need to understand the underlying biochemistry and physiology of the ADPKD and to provide treatments.

Therefore, it is an object herein to provide a means to identify the underlying biochemistry and genetics of these diseases and to provide a means to identify compounds for use in treatment of these diseases.

SUMMARY

Isolated genes, cDNA and encoded proteins from nematodes that participate in a pathway leading to an observable phenotype are provided. In particular, it is shown herein, that a mutation in *C. elegans*, which gives rise to males that are defective in certain aspects of mating behavior, lies in a gene designed herein lov-1 (location of vulva), and that this gene is an ortholog of the mammalian, particularly human, PKD1 gene. A mutation in a gene designated pkd-2 herein also gives rise to these behaviors. This gene is shown to be an ortholog of the mammalian, including human, PKD2 gene.

The expression pattern of lov-1 and pkd-2 was studied and it was found that promoter sequences of both genes cause reporter genes to be expressed in the rays and the hook sensory neurons required for 'response" and vulva location. Thus showing that the LOV-1 and PKD-2 proteins are involved in chemosensory or mechanosensory signal transduction in sensory neurons.

Hence genes that are components of a pathway in nematodes are provided and are shown to be linked to observable behaviors. Each of the encoded proteins, LOV-1 and PKD-2 are components in a pathway, which appears to be a signal transduction pathway, that leads to the observed phenotype. The genes from the nematode *Caenorhabditis elegans* are exemplified herein.

The pathway is shown to be homologous to the pathway in which the human polycystins, PKD1 and PKD2, participate. In particular, it is shown herein, that a mutation in nematodes, which gives rise to males that are defective in mating behavior, lies in a gene designated herein lov-1 (location of vulva). This gene, lov-1, is shown herein to be required for two male sensory behaviors, 'response' and 'location of vulva' (Lov).

A second gene, designated pkd-2, that affects this behavior in a similar manner is also identified and provided herein. The encoded proteins are also provided. The gene, cDNA, and encoded protein is also provided. In an exemplary embodiment, the *C. elegans* genome sequence was used to isolate pkd-2. This gene is a nematode ortholog of the mammalian, particularly human PKD2 gene. Strains that contain knock-out mutants of this gene also exhibit the defective mating behaviors.

In an exemplary embodiment, provided herein are the *C. elegans* genes, designated lov-1 and pkd-2. SEQ ID No. 3 sets forth the complement (i.e., the non-coding strand) of the lov-1 gene from *C. elegans*. SEQ ID No. 4 sets forth the sequence of amino acids of the protein (N-terminus to C-terminus)). SEQ ID No. 5 sets forth the complement (i.e., the non-coding strand) of the *C. elegans* pkd-2 gene from *C. elegans*. SEQ ID No. 6 sets forth the encoded sequence of amino acids.

Also provided are the mutants of the genes, lov-1, and pkd-2 and the resulting mutant encoded proteins. Nucleic acid molecules encoding mutants of these genes are also provided. For example, deletion mutants of these genes, particularly deletion mutants that substantially or completely knock-out gene product function, are provided. Thus, nucleic acid molecules containing deletions of each of these genes and deletion mutants that alter the phenotype of nematodes, such as *C. elegans*, that contain these mutant genes are also provided. Constructs, vectors, plasmids and strains containing each of the nucleic molecules are also provided. Also provided are strains defective in these genes.

Also provided are strains containing the mutant nucleic acids. Strains that manifest the defective male sensory behaviors are also provided herein. Constructs containing the genes, vectors containing the constructs, cells containing the vectors and transgenic *C. elegans*. Assays that use these strains of *C. elegans* are also provided.

As noted, it is shown herein that these genes are human homologs of the human genes that encode polycystins, proteins polycystin-1 (PKD1) and polycystin-2 (PKD2), which are defective in human autosomal dominant polycystic kidney disease. Hence, the genes and nematode strains provide model systems for studying this pathway, identifying additional components of the pathway, and for use in drug screening assays to identify compounds affect the pathway and/or compounds that serve as leads for development of drugs for treatment of polycystic kidney disease.

Each gene is shown to affect two sensory behaviors in *C. elegans*. One behavior designated "Response" and refers to the response of males to hermaphrodites; and the other behavior, designated "Lov" refers to location of the vulva by the male. Strains that are defective in either or both of these genes are also provided. In particular deletion mutants are provided.

By correlating the phenotypic behaviors with wild-type or defects in these genes, nematodes, such as *C. elegans*, can be used to identify other genes involved in this pathway and also means for direct screening for lead candidate compounds for drugs for treatment of PKD. Identification of additional genes necessary for PKD function can provide additional diagnostic tools for PKD. Hence, provided herein are mutant strains of *C. elegans* and assays that use the strains.

Also provided herein are assays that employ the constructs, vectors, plasmids and strains containing each of the nucleic molecules are also provided. In particular, in one type of assays wild-type nematodes are mutagenized or treated with a test compound, and those that exhibit a change in behavior are identified.

In other types of assays, nematodes that are defective in LOV and/or Response are mutagenized or treated with a compound, and those that exhibit a change in behavior are identified. Test compounds or mutations responsible for the change in behavior are identified. Such compounds are candidates for treatment of PKDs.

Among these methods are those that involved contacting a nematode that exhibits normal mating behavior with a test compound; and selecting compounds that result in altered mating behavior, wherein the altered mating behavior comprises alteration in the behavior involving location of vulva and/or response to contact with the hermaphrodite.

Also provided are methods for identifying genes involved in autosomal dominant polycystic kidney disease (ADPKD). Among these methods are those in involving mutagenizing nematodes that exhibit normal mating behavior; and identifying and selecting nematodes that exhibit altered mating behavior, where the altered mating behavior is manifested as an alteration in location of vulva and/or response to contact with the hermaphrodite. The mutated gene(s) responsible for the alteration in behavior are then identified. Databases or libraries of mammalian genes can be screened to identify homologs of these genes, which can then serve as therapeutic or diagnostic targets or aid in elucidation of the disease pathology.

Methods for identifying compounds that are candidate therapeutic agents for treatment of autosomal dominant polycystic kidney disease (ADPKD) are provided. Among the methods are those in which normal males are treated with a candidate compound. Compounds that result in changes in mating behaviors or changes in mating efficiencies are selected.

Methods for identifying genes involved in the disease pathway are also provided. Among the methods are those in which normal males are mutagenized. Offspring that exhibit changes in mating behaviors or changes in mating efficiencies are selected and mutated genes are identified and shown to be part of the pathway. Mammalian, particularly human, homologs of the mutated genes are then identified. Such genes are likely to be part of the disease pathway. Such genes can serve as therapeutic targets and disease markers for diagnostic.

Other assays use nematode strains that have mutations in either or both of lov-1 or pkd-2. As described herein, suppressor and enhancer genetics can be used to assign functions to genes, to assign genes to pathways, to identify the key switches in these pathways and to provide a sensitive assay to identify new genes in a pathway and lead compounds that modulate the activity of genes and/or gene products in the pathway.

Assays that identify the role of PKD proteins in sensory function are also provided. Since lov-1 and pkd-2 are expressed in CEM neurons, they have activity in other sensory functions, such as finding the mating partner at a distance. Accordingly assays using sexual chemotaxis or kinesis are provided. For example, males that are mutagenized or treated with a test compound are placed on a surface containing males and hermaphrodites, and are then observed to assess whether they can choose between males and hermaphrodites. If the male is defective in this sensory function, it will not distinguish between males and hermaphrodites.

Assays that use dominant negative forms of PKD in nematodes or in other cells to identify mutations and/or compounds that inhibit PKD function are also provided. Transgenic nematodes that express a version of the LOV-1 or PKD-2 protein that inhibits the activity of LOV-1 and/or PKD-2 as assessed by manifestation of the altered LOV and/or response phenotypic behavior(s) are used in these assays. Transgenic nematodes can be produced by any method known to those of skill in the art, including, but are limited to, injection of the nucleic acid into the embryos or cells of the animal. Transgenic nematodes that contain a dominant negative lov-1 or pkd-2 transgene are contacted with a test compound, and compounds that interfere with a remaining activity of the LOV-1 or PKD-2 protein are selected. Alternatively, these transgenic nematodes are mutagenized and mutants that lose a remaining activity are selected and the gene or mutation responsible for the loss or that contributes to the loss is identified.

Assays based on localization and trafficking of LOV-1 and/or PKD-2 within a cell or cells are also provided. These assays can identify regulators and factors necessary for synthesis and transport of LOV-1 and/or PKD-2 proteins and employ strains in which LOV-1 and PKD-2 are expressed linked to a detectable label, such as a fluorescent protein. These strains are used to assess the effects of compounds or mutagenesis on the trafficking patterns of LOV-1 and PKD-2 and cellular location(s) of the proteins in the animal. Identified mutations can be mapped and the genes identified. If mammalian, particularly human, homologs of these identified genes exist, such genes can serve as therapeutic or diagnostic targets and can aid in elucidation of the disease in mammals, particularly humans.

Assays for identification of transcriptional regulators of expression of lov-1 and/or pkd-2 are also provided. These assays screen for loss or alteration of expression of either gene and use transgenic nematodes with a reporter gene, such as a gene encoding a FP or lacZ or other detectable product, linked to the nucleic acid encoding lov-1 or pkd-2. The animal is mutagenized or treated with a test compound and loss of expression or reduction in expression of either gene is assessed. These assays identify regulators of and factors that affect lov-1 and pkd-2 expression. Mammalian, particularly human homologs of these regulators and factors are identified. Such regulators and factors can be therapeutic or diagnostic targets, and/or can aid in developing an understanding of the development and progression of PKD in mammals.

Kits for performing the assays, particularly, the drug screening assays, are also provided. The kits include transgenic or wild-type nematodes or both that express either wild-type or a mutant or a transgenic form of lov-1 and/or pkd-2. The nematodes may be on plates, in wells or in any form suitable for the assays. Kits containing nucleic acid encoding either of the two genes or probes based upon these sequences or reporter gene constructions containing all or portions of either or both genes are also provided. The nucleic acids may be in solution, in lyophilized or other concentrated form, or may be bound to a suitable substrate. The kits can include additional reagents for performing the assays, such reagents include any for performing any of the steps of the methods. The kits include instructions for performing the assays.

DETAILED DESCRIPTION

Definitions

Figure 1:
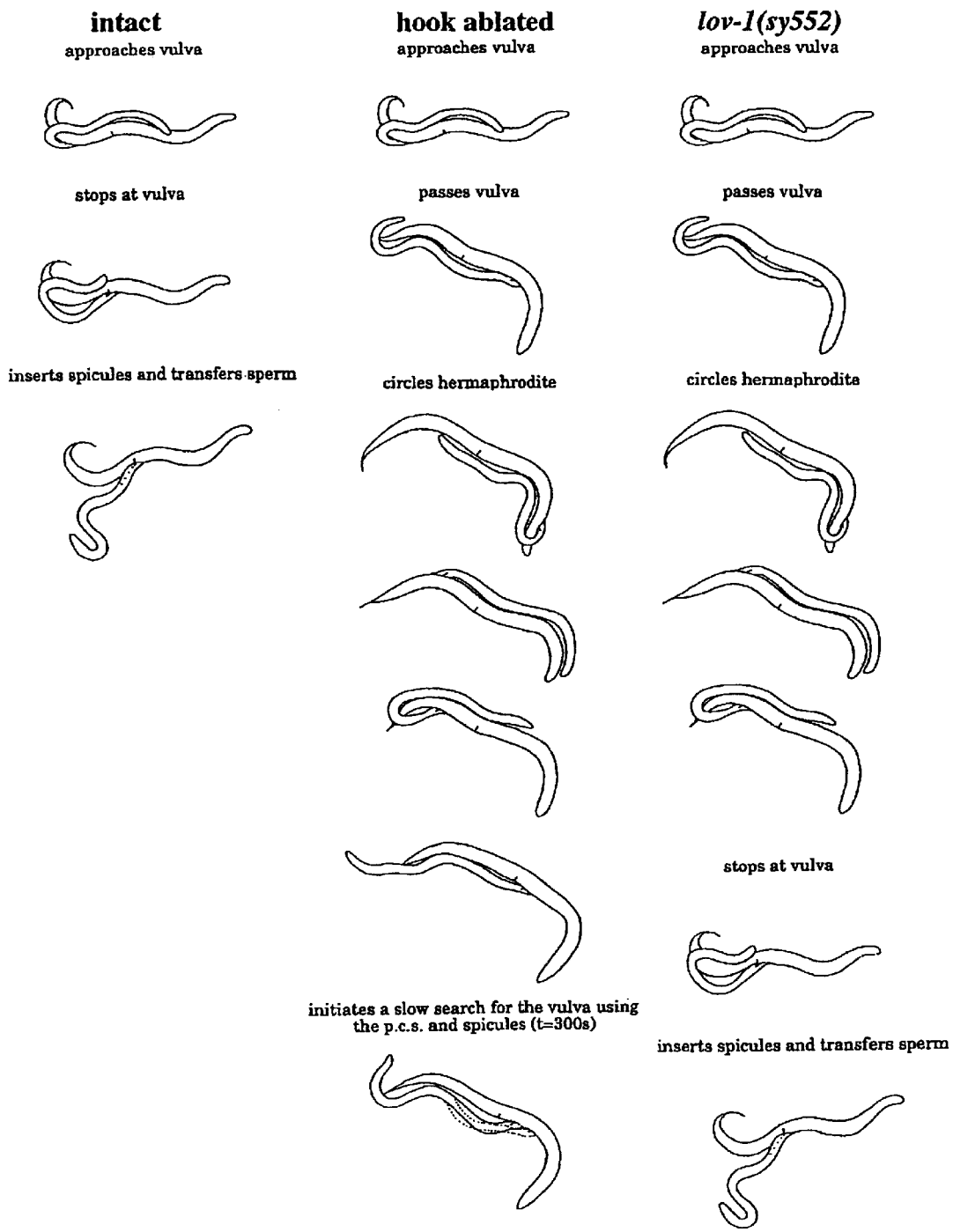
FIG. 1 depicts male mating behavior of *C. elegans*. The hermaphrodite is larger than the male and her vulva is depicted as a slit on the ventral, posterior third of her body. The male tail is place flush on the hermaphrodite, ventral side down. His spicules are depicted by a line in the tail. The hook is anterior to the spicules, the post cloacal sensilla is posterior. Sequence 1 illustrates wild-type male Lov. Sequence 2 represents hook ablated aberrant Lov behavior (passing and slow search). Sequence 3 portrays lov-1(sy552) mutant behavior (passing and eventually stopping).

Unless defined otherwise, all technical and scientific terms used herein have the same meaning as is commonly understood by one of skill in the art to which this invention belongs. *Caenorhabditis elegans* nomenclature is well understood by those of skill in this area (see, e.g., *Methods in Cell Biology C. elegans* I, and II, Cold Spring Harbor Press Books, Shakes, Epstein eds).

All patents, patent applications and publications referred anywhere herein, including the background, are, unless noted otherwise, incorporated by reference in their entirety. In the event a definition in this section is not consistent with definitions elsewhere, the definition set forth in this section will control.

As used herein, nematode is intended to refer generally to the class Nematoda or Nematoidea and includes those animals of a slender cylindrical or thread-like form commonly called roundworms. Among those species, members of the genus Caenorhabditis are preferred, but species that can be cultured in the laboratory may be used.

As used herein, the term "mutant," as in "nematode mutant" or "mutant nematode," is intended to refer generally to a nematode which contains an altered genotype, preferably stably altered. The altered genotype results from a mutation not generally found in the genome of the wild-type nematode.

As used herein, a mutant gene, such as a mutant lov-1 or pkd-2 gene, refers to a gene that is altered, whereby a nematode with such gene, expresses an altered phenotype compared to a nematode with the wild type gene, such as a the genes set forth in SEQ ID Nos. 3 and 5 (which set forth the non-coding strands). Mutations include point mutations, insertions, deletions, rearrangements and any other change in the gene that results in an altered phenotype. Deletion mutants that eliminate the function of the encoded protein (knock-out mutations) are exemplified herein. Not all mutation necessarily completely destroy the activity of the protein.

As used herein, "normal mating behavior" means that the animal exhibits behavior typical of wild-type nematodes with respect to the location of vulva (Lov) and response to of males to hermaphrodites. Thus a male that exhibits "normal mating behavior" upon encountering a hermaphrodite, ceases forward motion, places his tail flush on the hermaphrodite, commences backing along her body, and turns at her ends until he encounters her vulva and stops. This is the behavior of a lov-1(+) male. Mutant males defective in lov-1 frequently do not respond to contact with the hermaphrodite and continue blindly moving forward. When response is initiated, lov-1 mutants back and turn normally but pass the vulva at a high frequency. Thus, they can mate with paralyzed or otherwise slow moving hermaphrodites.

As used herein, a mammalian homolog of a nematode gene refers to a gene that encodes a protein that exhibits identifiable sequence homology and conservation of structure. The degree of sequence homology between a mammalian and nematode protein or gene to be considered homologs depends upon the gene considered but is typically at least about 30% at the protein level. An ortholog will typically have greater sequence similarity, and conservation of structure and often function. Methods and criteria for identifying mammalian, including human, homologs of nematode genes are known to those of skill in the art and involve a comparison of the sequence and structural features of the encoded protein.

As used herein, a dominant negative mutation is a mutation that encodes a polypeptide that when expressed disrupts that activity of the protein encoded by the wild-type gene (see, Herskowitz (1987) *Nature* 329:219–222). The function of the wild-type gene is blocked, a cloned gene is altered so that it encodes a mutant product that inhibits the wild-type gene product in a cell or organism. As a result, the cell or organism is deficient in the product. The mutation is "dominant" because its phenotype is manifested in the presence of the wild-type gene, and it is "negative" in the sense that it inactivates the wild-type gene function. It is possible to do this because proteins have multiple functional sites.

As used herein, a "library" of nematodes is a collection of a plurality of nematodes, typically more than 10, preferably more than 100. Typically a library will include variety of different nematodes and may include wild-type and mutant nematodes and a sufficient number to achieve the intended purpose for which the library is used.

As used herein, a gene encoding LOV-1 protein refers to a gene (a sequence of nucleotides including introns, and exons, and optionally transcriptional regulatory sequences) from any nematode that encodes a protein that performs the same function in the nematode as the LOV-1 protein provided herein. Such protein can be identified using the methods provided herein for identifying it in *C. elegans*, or by isolating cDNA encoding the protein using probes constructed from the nucleic acid provided herein to isolate it using standard methods. Typically the coding sequence of the gene provided herein will hybridize along its length to the coding sequence of a related gene under conditions of at least low stringency, preferably moderate stringency, and likely under conditions of high stringency. Nucleic acid encoding a LOV-1 protein includes any nucleic acid molecule, DNA, cDNA, RNA, that encodes a protein that has substantially the sequence of amino acids set forth in SEQ ID No. 4 and encodes a protein that has the same activity as this protein. Minor sequence variations from species to species and even among a species are considered to be substantially the same sequence. Such nucleic acid will hybridize to the nucleic acid encoding the proteins provided herein under conditions of at least low stringency, preferably moderate stringency and more preferably high stringency.

As used herein, a gene encoding PKD-2 protein from a nematode is similarly defined, except that it has the substantially the same sequence as the sequence of amino acids set forth in SEQ ID No. 6. Having identified these proteins and functions therefor in *C. elegans* permits similar identification in other nematode species.

As used herein, stringency conditions refer to the washing conditions for removing the non-specific probes and conditions that are equivalent to either high, medium, or low stringency as described below:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

As used herein, percentage or amount or degree of sequence identity is used interchangeable with homology and refers to sequence identity or homology determined using standard alignment programs with gap penalties and other parameters set to the manufacturer's default settings. It is understood that for relatively high levels of sequence identity or homology, the particular program selected and/or defaults set for various parameters, do not substantially affect the results. Hence, for example, a requirement for 90% sequence identity of a nucleic acid sequence with another can be determined using any program known to the skilled artisan or manually, and that such percentage can encompass about 85% to 95% identity.

As used herein, reference to a drug refers to a chemical entity, whether in the solid, liquid, or gaseous phase that is capable of providing a desired therapeutic effect when administered to a subject. The term "drug" should be read to include synthetic compounds, natural products and marco molecular entities such as polypeptides, polynucleotides, or lipids and also small molecules, including, but are not limited to, neurotransmitters, ligands, hormones and elemental compounds. The term "drug" is meant to refer to that compound whether it is in a crude mixture or purified and isolated.

As used herein, heterologous or foreign DNA and RNA are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Examples of heterologous DNA include, but are not limited to, DNA that encodes exogenous invertase. Heterologous DNA and RNA may also encode RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, a gene containing a heterologous transcriptional or translational or processing control region(s) refers to a nucleic acid molecule or construct that includes coding portion of a gene operatively linked to a such region derived from a different gene. A homologous transcriptional or translational or processing control region(s) refers to a nucleic acid molecule or construct that includes coding portion of a gene operatively linked to a such region derived from the same gene.

As used herein, a promoter region refers to the portion of DNA of a gene that controls expression of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. A constitutive promoter is always turned on. A regulatable promoter requires specific signals to be turned on or off. A developmentally regulated promoter is one that is turned on or off as a function of development.

As used herein, regulatory sequences include, sequences of nucleotides that function, for example as transcriptional and translational control sequences. Transcriptional control sequences include the promoter and other regulatory regions, such as enhancer sequences, that modulate the activity of the promoter, or control sequences that modulate the activity or efficiency of the RNA polymerase that recognizes the promoter, or control sequences are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, transcriptional controls sequences, include sequences of nucleotides that alter translation of the resulting mRNA, thereby altering the amount of a gene product.

As used herein, a reporter gene refers to a gene that encodes a detectable product. Such genes are well known to those of skill in the art and include, but are not limited to, genes encoding fluorescent proteins, particularly the well-known green fluorescent proteins, lacZ, enzymes and other such reporters known to be expressible and detectable in nematodes. These genes are linked to a gene of interest whereby upon expression a detectable fusion protein is produced. For purposes herein, such fusions are exemplified using an aequorin GFP (see, Chalfie et al. (1994) *Science* 263:802–805; see, also U.S. Pat. No. 5,741,668), but any such protein may be used. For example, GFP from *Aequorea victoria* contains 238 amino acids, absorbs blue light and emits green light; it has been cloned and its sequence characterized; various mutants are also well known. Nematode optimized codons may be selected.

As used herein, a reporter gene construct is a nucleic acid molecule that includes a reporter gene operatively linked to transcriptional control sequences. Typically the construct will also include all or a portion of a the gene of interest, which herein is lov-1 and/or pkd-2, and the reporter gene will be under the control of the lov-1 or pkd-2 promoter and other regulatory regions. By operatively linked is meant linked whereby an in-frame fusion protein is produced upon expression of the construct and whereby the reporter gene product is active (i.e. produces a detectable signal or is active). The reporter gene may be linked to the 3' or 5' end or in any other orientation whereby it is expressed and operates as a reporter.

As used herein, isolated, substantially pure DNA refers to DNA molecules or fragments purified according to standard techniques employed by those skilled in the art, such as those described in Sambrook et al. (1989) *Molecular Cloning: A Laboratory Manual*, Cold Spring Harbor Laboratory Press, Cold Spring Harbor, N.Y.).

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, cloning vehicle or vector, which are used interchangeably, refers to a plasmid or phage DNA or other DNA molecules that replicate autonomously in a host cell, and that include one or a small number of endonuclease recognition sites at which such DNA may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, include but are not limited to, tetracycline resistance and ampicillin resistance.

Appropriate expression vectors are well known to those of skill in the art and include those that are replicable in eukaryotic cells and/or prokaryotic cells. Such expression vectors may remain episomal or may integrate into the host cell genome. Expression vectors suitable for introducing heterologous DNA into plants and into host cells in culture, such as mammalian cells and methylotrophic yeast host cells, are known to those of skill in the art. It should be noted that, because the functions of plasmids, vectors and expression vectors overlap, those of skill in the art use these terms, plasmid, vector, and expression vector, interchangeably. Those of skill in the art, however, recognize what is intended from the purpose for which the vector, plasmid or expression vector is used.

As used herein, integrated into the genome means integrated into a chromosome or chromosomes.

As used herein, a "fragment" of a protein refers to any portion of a protein that contains less than the complete amino acid sequence of the protein but that retains a biological or chemical function of interest.

As used herein, expression vector or expression vehicle refers to such vehicle or vector that capable, after transformation into a host, of expressing a gene cloned therein. The cloned gene is usually placed under the control of (i.e., operably linked to) certain control sequences such as promoter sequences. Expression control sequences will vary depending on whether the vector is designed to express the operably linked gene in a procaryotic or eukaryotic host and may additionally contain transcriptional elements such as enhancer elements, termination sequences, tissue-specificity elements, and/or translational initiation and termination sites.

As used herein, a variant of a protein refers to a protein substantially similar in structure and biological activity to either the entire protein or a fragment thereof. Thus, provided that two proteins possess a similar activity, they are considered variants as that term is used herein even if the composition or secondary, tertiary, or quaternary structure of one of the molecules is not identical to that found in the other, or if the sequence of amino acid residues is not identical.

It is also understood that any of the proteins or portions disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p.224). Such substitutions are preferably, although not exclusively, made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Comparable mutations may be made at the nucleotide sequence level.

Other substitutions are also permissible and may be determined empirically or in accord with known conservative substitutions. Any such modification of the polypeptide may be effected by any means known to those of skill in this art. Mutation may be effected by any method known to those of skill in the art, such as by chemicals or radiation, and also including site-specific or site-directed mutagenesis of DNA encoding the protein and the use of DNA amplification methods using primers to introduce and amplify alterations in the DNA template.

As understood by those skilled in the art, assay methods for identifying compounds, such as antagonists and agonists, that modulate functioning of a protein or protein or pathway, generally require comparison to a control. One type of a "control" system is one that is treated substantially the same as the system, such as a worm, exposed to the test compound except that the control is not exposed to the test compound. Another type of a control may be that is identical to the test system, except that it does not express the gene or protein of interest. In this situation, the response of test system is compared to the response (or lack of response) of the control to the test compound, when each cell is exposed to substantially the same reaction conditions in the presence of the compound being assayed.

As used herein, treatment means any manner in which the symptoms of a conditions, disorder or disease are ameliorated or otherwise beneficially altered.

As used herein, amelioration of the symptoms of a particular disorder by administration of a particular pharmaceutical composition refers to any lessening, whether permanent or temporary, lasting or transient that can be attributed to or associated with administration of the composition.

As used herein, a composition refers to any mixture of two or more components. It may be solution, suspension, or any other mixture.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

Nematodes as Disease Models

Nematodes serve as model organisms for the study of gene expression. *Caenorhabditis elegans* is representative of nematodes. It is a small, freeliving bacteriovorous soil nematode that is a member of the Rhabditidae, a large and diverse group of nematodes found in terrestrial habitats. Some rhabditids are pathogenic to or parasitic on animals. In common with other nematodes, *C. elegans* develops through four larval stages (also called juveniles) that are separated by moults. The lifecycle takes about 3 days at 20° C.

*C. elegans* is only 1 mm long and can be handled in a manner similar to microorganisms, including growth on petri plates seeded with bacteria. In the laboratory, *C. elegans* is fed on *E. coli*. It has a transparent body and all somatic cells (959 female; 1031 male) are visible with a microscope.

Although it is a primitive organism, it shares many of the essential biological characteristics, including embryogenesis, morphogenesis, development and aging that are central problems of human biology. The worm is conceived as a single cell that undergoes a complex process of development, starting with embryonic cleavage, proceeding through morphogenesis and growth to the adult. It has a nervous system with a 'brain' (the circumpharyngeal nerve ring), It exhibits definable behaviors, and is capable of rudimentary learning. It produces sperm and eggs, mates and reproduces. After reproduction it gradually ages, loses vigor and dies. Its average life span is 2–3 weeks.

Adult *C. elegans* are usually self-fertilizing protandrous hermaphrodites. As a result homozygous mutant stocks can be readily generated. The hermaphrodite gonad first produces germ cells that differentiate as sperm (about 250 sperm are produced) and then produces eggs. The fecundity is determined by the sperm supply.

Nematodes, particularly *C. elegans*, is one of the most thoroughly understood of all multicellular organisms. The biology of its nervous system, which contains 302 neurons, is well-documented. Many *C. elegans* genes used have counterparts in mammals, including humans. At least half of the *C. elegans* genes and proteins that have been characterized have structures and functions similar to mammalian genes. These include genes encode enzymes, proteins necessary for cell structure, cell surface receptors and genetic regulatory molecules.

Animals from man to worm have most of their protein families in common and humans frequently have four to five close analogs of a protein family member, where worms have only one. Essentially all genes and pathways shown to be important in cell-, developmental- and disease-biology have been found to be conserved between worm and human. This conservation applies to the number and type of protein families, gene structure, the hierarchy of genes in genetic pathways and even gene regulation.

A consequence of this conservation is that human genes can be inserted into the worm genome, to functionally replace the worm genes even in complex cell biological and signal transduction pathways. Conversely, key worm genes identified using genetics can be used to trigger specific biochemical processes in human cells and to serve as models for the human genes.

Genetics Nomenclature

*C. elegans* is diploid and has five pairs of autosomal chromosomes (designated I, II, III, IV and V) and a pair of sex chromosomes (X) that determine gender. XX is a hermaphrodite and XO is male. Males are found rarely (about 0.05% of normal lab populations). The commonest lab strain, and the designated "wild-type" strain, is called N2.

For historical reasons *C. elegans* nomenclature is different from other species. Loci have a 3-letter dash one number designation. The letters are an acronym for the phenotype and the number is consecutive. Alleles have a single or double letter followed by a number. The letter identifies the isolating laboratory. Strains have a letter(s) number designation. The letters identify the isolating laboratory (i.e. AB100 abc-1 (xy1000) Strain AB100 which carries the xy1000 allele of abc-1. The chromosomal location can be added: AB100 abc-1(xy1000) I. Multiple mutant alleles carried in one strain are organized by chromosome, and chromosomes separated by semicolons. Heterozygous nematodes are designated by a abc-1/+ notation. Hence abc-1 (+) indicates the wild-type (N2 strain) copy of the gene. Proteins are capitalised and not italicized. ABC is the protein product of abc-1.

Rearrangements, duplications and deficiencies have a letter prefix (indicating the isolating lab) a Dp (pronounced dupe, for duplication) or Df (pronounced dif for deficiency) and a number (i.e., xyDp1 is duplication number 1 from xy and xyDf1 is deficiency number 1 from xy lab). Transgenic strains carrying the transgene as a free extrachromosomal array are designated as follows: xyEx1[abc-1(+)] is a transgenic strain carrying the wt copy of abc-1.

The *C. elegans* Genome

The *C. elegans* genome, which is 97 Mb, contains six approximately equally sized chromosomes (5 autosomes, one X), it has been sequenced (see,(1998) *Science* 282:2012–2018) and is publicly available. The 97 Mb encodes a predicted 19,099 protein coding genes; although as shown herein, there remain ambiguities. Over 60,000 cDNA fragments have been tag sequenced and 101000 ESTs deposited. These "expressed sequence tags" or ESTs offer a set of snapshots of gene expression in the nematode, and have identified around half of the organism's genes. The cDNA data is used in the prediction of genes from the genome sequence along with database searches for similarities between *C. elegans* genes and those of other organisms such as humans. This estimate is based on the correspondence between genomic DNA sequence and cDNA sequences, and on the prediction of coding genes from genomic sequence. The genome data (and much else besides) is collated into an available database ACeDB, written for the *C. elegans* project. A physical map of the genome, which is publically available in the *C. elegans* genome database ACeDB, has been constructed. The map is based on 17,000 cosmid clones of genomic DNA (insert size 35–40 kb). These clones were "fingerprinted" using restriction enzymes, and the fingerprints used to order the clones in overlapping contiguous sets, or contigs. These cosmid contigs have been supplemented by a set of 3,000 yeast artificial chromosome clones (insert sizes 100 kb and above). Because the yeast host tolerates sequences that *E. coli* does not, the YAC clones can "bridge" gaps between contigs of cosmids. With these two resources, contigs covering >95% of all the chromosomes have been assembled. The clones are freely available for researchers, and the 3,000 YAC clones are available as an array on a filtermat, arranged in approximate chromosomal order, for screening purposes.

The genomes of other nematodes are in the same size range. *Brugia malayi*, a filarial parasite of humans, has a genome of 100 Mb; *Ascaris suum*, the pig roundworm, has a larger germ line genome which undergoes somatic diminution.

Identification of the Genes Associated With the Location of Vulva and Response Behaviors The Behaviors The six sub-steps of the stereotyped copulatory sequence has been correlated with the function of individual neurons, and behavioral mutants have been isolated (Liu et al. *Neuron* 14:79–89). *C. elegans* male mating behavior includes a series of steps: response to contact with the hermaphrodite, backing along the body of the hermaphrodite, turning around her head or tail, location of the vulva, insertion of the two copulatory spicules into the vulva and sperm transfer. Sensory structures and neurons that participate in each of these steps have been identified: the sensory rays mediate response to contact and turning; the hook, the postcloacal sensilla and the spicules mediate vulva location; and the spicules also mediate spicule insertion and regulate sperm transfer.

Thus, the stereotyped mating behavior of the *Caenorhabditis elegans* male comprises several substeps: response backing, turning, vulva location, spicule insertion, and sperm transfer (FIG. 1). The complexity of male mating behavior is reflected in the sexually dimorphic anatomy and nervous systems of the male and hermaphrodite (Hodgkin, J. (1988) in *The Nematode C. elegans* (ed. Wood, B.) pp. 243–279 (Cold Spring Harbor Laboratory Press, New York). Behavioral functions have been assigned to most male-specific sensory neurons via cell ablations (Liu et al. *Neuron* 14:79–89). Although the hermaphrodite is behaviorally passive, her vulva provides sensory cues to the male.

Vulva location behavior is complex. The male stops and precisely positions his tail over the vulva, coordinates his movement to the hermaphrodite's, and ultimately insert his spicules into the vulva slit and transfers sperm into the uterus. The hook sensory neurons, HOA and HOB, are specifically required for location of vulva (Lov) behavior. Ablation of either HOA or HOB results in a Lov defect whereby the ablated male circles the hermaphrodite without stopping at the vulva (FIG. 1). Eventually, the ablated male begins an alternative search by backing slowly and prodding randomly with his spicules until the vulva is located. The postcloacal sensilla are required for slow search behavior. Vulva location behavior is executed by a minimum of eight sensory neurons with overlapping and redundant functions (Liu et al. *Neuron* 14:79–89).

A genetic analysis of vulva location behavior to investigate how genes specify sensory behavior, beginning with sensory reception was performed. The mating behavior of existing mutants defective in sensory behaviors including chemotaxis to soluble and volatile odorants, mechanosensation, and osmotic avoidance was first examined. From this survey, it was found that only males with severe defects in all sensory neuron cilia (osm-4, osm-5, osm-6, and che-3) were Lov defective (Table 2). For example, osm-6(p811) males locate the vulva with an efficiency of 32% versus 96% of wild-type (Table 2). These males are also response defective, but not so severely as to prevent observation of the Lov phenotype. The only ciliated cells in *C. elegans* are chemosensory and mechanosensory neurons (White et al. (1986) *Philos. Trans. R. Soc. Lond. B Biol. Sci.* 314:1–340). The male tail possesses thirty predicted ciliated sensory neurons (Suiston et al. (1980) *Dev. Biol.* 78:542–576), consistent with the observation that ciliated neurons modulate response and Lov. osm-6::gfp is expressed exclusively in ciliated neurons, with male-specific expression in four CEM head neurons and neurons of the rays and copulatory spicules (Collet et al. (1998) *Genetics* 148: 187–200). More detailed examination revealed that osm-6::gfp expression begins at the L4 stage in neuronal cell bodies and extends to dendrites as neuronal outgrowth proceeds (data not shown). The RnA and RnB neurons of each ray (ray 1 through ray 9), the HOA and HOB hook neurons, the spicule neurons SPV and SPD, and the PCB postcloacal sensilla neurons accumulate GFP. The osm-6 expression pattern and mutant phenotypes indicate that OSM-6 might be required for the structure and function of ciliated neurons in the adult male tail. In the hermaphrodite, osm-6 function is required for nose touch (Kaplan et al. (1993) *Proc. Natl. Acad. Sci. U.S.A.* 90:2227–2231), osmotic avoidance, chemotaxis, dye-filling of sensory neurons, thermotaxis, dauer formation, and proper assembly of ciliated sensory endings (Perkins et al. (1986) *Dev. Biol.* 117:456–487). Hence, ciliated endings are important for all known sensory behaviors, including Lov.

TABLE 2

Vulva location behavior of wild-type and mutant males

| Genotype | vulva location efficiency % | Significantly different from wild-type (p value) | [1]n |
|---|---|---|---|
| him-5(wild-type) | 96 | — | — | 101 |
| osm-1(e1803) | 65 | No | (0.0738) | |
| osm-4(p821) | 48 | Yes | (0.0004) | |
| osm-5(p813); him-5 | 26 | Yes | (0.0002) | |
| osm-6(p811) | 32 | Yes | (0.0003) | |
| che-3(e1124) | 69 | Yes | (0.02666) | |
| lov-1(sy582Δ) | 11 | Yes | (<0.0001) | |
| lov-1(sy582); him-5 | 30 | Yes | (<0.0001) | |

Table 2. lov-1(sy522), him-5(e1490), lov-7(sy582Δ), and all cilia defective mutant were also response defective. Males that eventually responded were scored for Lov behavior. [1]n represents the number of males observed, each for a minimum of to vulva encounters per male. Mann-Whitney tests determined p values. The following non-cilia-defective osmotic avoidance (osm), mechanosensory defective (mec), chemosensory defective (che), odorant response abnormal (odr) and dauer formation defective (daf) mutants were also examined and found to be normal for response and Lov behavior: osm-3(e1806): him-5(e1490), osm-7(n1515), osm-8(n1518), osm-10(n1604), osm-11 (n1604), osm-12(n1606), mec-3(e1338) him-8(e1489), mec-4(e1611), mec-5(e1340), mec-7(n434), mec-7(e1343), mec-8(e398), mec-9(e1494), che-112, odr-1(n1936), odr-2(n2145), odr-3(n2150), odr-4 (n2144ts), odr-5, odr-6(kyl), odr-7(ky4, odr-10(ky32) and daf-11(m47ts).

Provided herein are mutants that are defective in location of the vulva (Lov). Lov mutant males are unable to execute this step. In addition, these males are also defective in the first sub-step, 'response'. Response and vulva location depend on two types of male sensory structure: the first is a set of nine pairs of rays, which project out of the tail on each side; and the second is a hardened cuticular structure called the hook, which contains two sensory neurons. These mutants were used to identify the genes involved in these behaviors.

Identification and Cloning of the lov-1 Gene

To elucidate the molecular basis of behavior and sensory the mutants are studied and genes associated with the behaviors are identified. A gene designated lov-1 that is required for two male sensory behaviors, response and location of vulva (Lov) is described herein. It is also associated with other sensory behaviors controlled by the CEM neurons.

This gene, lov-7, encodes a putative membrane protein with a mucin-like, serine-threonine rich amino terminus (Carraway et al. (1995) *Trends Glycoscience Glycotechnology* 7:31–44) followed by two blocks of homology to human polycystins encoded by the autosomal dominant polycystic kidney disease (ADPKD) genes (Torres et al (1998) Current Opinion in Nephrology and *Hypertension* 7:159–169). LOV-1 and human PKD1 are 26% identical in block 1. Block 2 also shows 20% identity between LOV-1, all identified polycystins (PKD1, PKD2, and PKDL), and the family of voltage-activated channels (Torres et al. (1998) Current Opinion in Nephrology and *Hypertension* 7:159–169). Overall, LOV-1 is the closest *C. elegans* homolog of PKD1. The polycystin/channel domain (block 2) of LOV-1 is required for function. Lov-1 is specially expressed in adult male sensory neurons of the rays, hook, and head, mediating response, Lov, and potentially chemotaxis to hermaphrodites, respectively (Liu et al. *Neuron* 14:79–89, Ward et al. (1975) *J. Comp. Neurol.* 160:313–337). Localization of lov-1 to neuronal cell bodies and ciliated sensory endings is consistent with a role in either chemo- and/or mechanosensory reception and signaling. Human PKD proteins might similarly be involved in sensory reception during osmoregulation, organogenesis and/or organ maintenance.

Cloned Genes and Encoded Proteins

To identify genes specifically required for male sensory behaviors, mutants defective in Lov were screened. Lov-1 (sy552) males have specific response and Lov defects. Upon encountering a hermaphrodite, a lov-1(+) male ceases forward motion, places his tail flush on the hermaphrodite, commences backing along her body, and turns at her ends until he encounters her vulva and stops. Mutant males defective in lov-1 frequently do not respond to contact with the hermaphrodite and continue blindly moving forward. When response is initiated, lov-1 mutants back and turn normally but pass the vulva at a high frequency. The response and vulva location ability of lov-1(sy552) is 30% that of lov-1(+) males (Table 2). Spicule insertion and sperm transfer behaviors are unaffected. lov-1(sy552) males exhibit high mating efficiency with severely paralyzed unc-52 hermaphrodites but sire few progeny with actively moving dpy-17 hermaphrodites. Differences between mating efficiencies is partner-dependent. A paralyzed partner is an easier target for the lov-1 mutant male who is defective in response and Lov but unimpaired in the behaviors of backing, turning, spicule insertion, and sperm transfer. The behavioral defects of sy552 are limited to male mating. Lov-1(sy552) mutants appear normal for other sensory behaviors including egg laying, nose touch, tap, mechanosensation, and osmotic avoidance.

Figure 2:
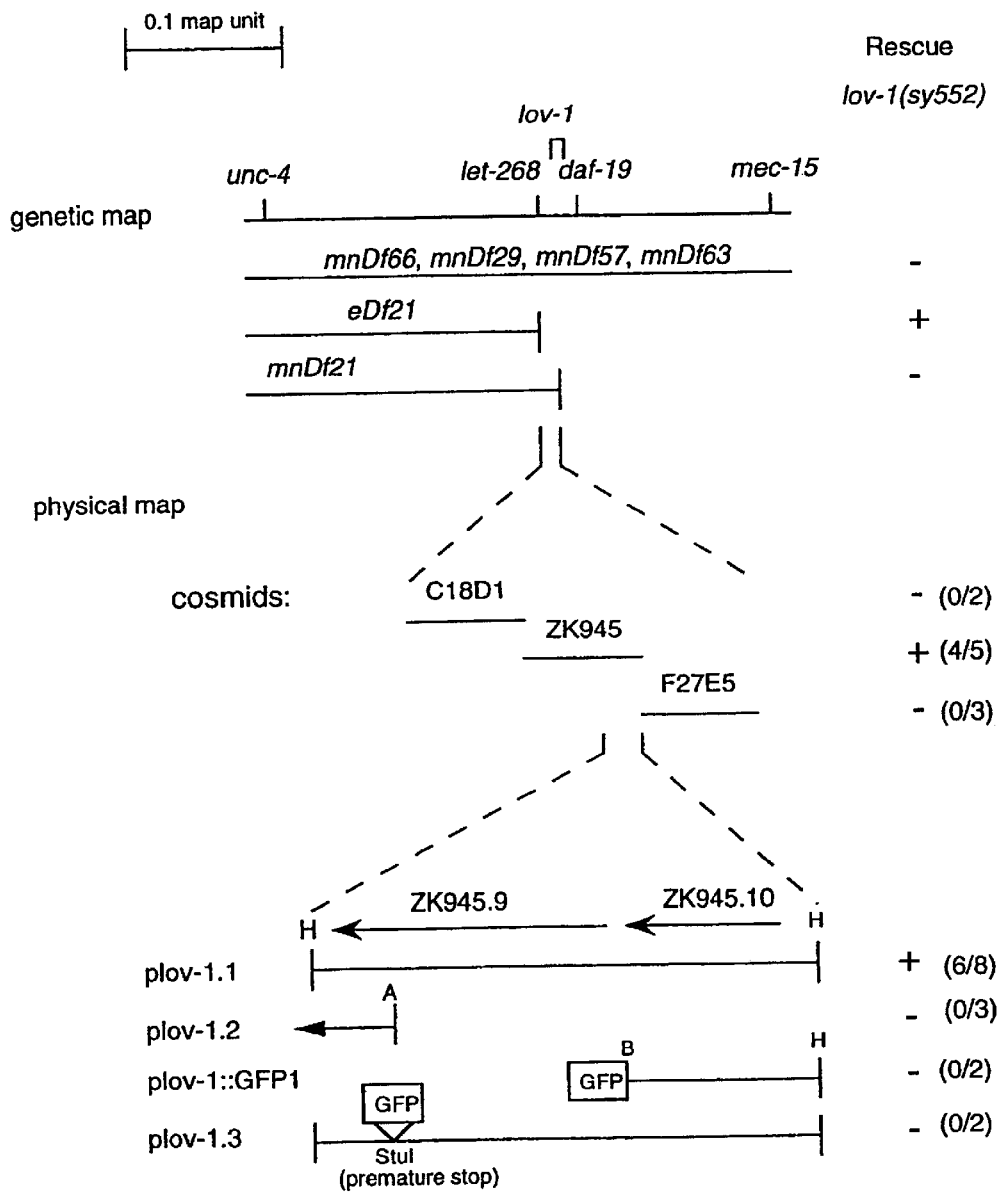
FIG. 2 depicts the molecular nature of lov-1. a, Genetic and physical maps of the lov-1 region on chromosome 2. Genetic markers are shown. Boundaries of a lov-1 deletion (mnDf21) and non-deletion (eDf21) are indicated. + designate rescue of lov-1(sy552) mutant males. Numbers in parentheses indicate the ratio of rescuing stable lines to total stable lines examined. b, lov-1 gene structure. Exons are boxed. Genefinder predicts two ORFs, ZK945.10 (9 exons) and ZK945.9 (19 exons). RT-PCR reveals lov-1 corresponds to the combination of ZK945.10 and ZK945.9. The arrow indicates the 1059 bp deletion in lov-1 (sy582Δ) c, lov-1::GFP (green fluorescent protein) expression constructs, patterns, and phenotypes in wild-type background. d, lov-1 encodes a membrane associated protein with homology to the polycystin and voltage-activated channel families. A schematic representation of LOV-1 is shown to demonstrate domains of the protein. These include the amino terminus that is serine/threonine rich with multiple potential glycosylation sites, an ATP/GTP binding domain (indicated by the asterisks), followed by two polycystin blocks of homology. Block 1 is exclusively homologous to PKD1, while Block 2 shows homology with all polycystins and also the family of voltage activated $CA^{2+}$ channels. Block 1 is a conserved domain of unknown function, that also occurs at the N-terminus of most 5-lipoxygenases. Identity (%) and number of identical amino acids (in parentheses) between LOV-1 and a particular polycystin is indicated. Although LOV-1 lacks the carboxy terminal coiled-coil domain of all known polycystins, a coiled-coil is predicted in the middle of LOV-1 using the most stringent criteria for the COILS program (data not shown). Y73F8A.B+A was identified in a Blast search of unpublished sequences available through the Sanger Center and is more similar to PKD2 (30% identity, 48% similarity, 13% gaps over 752 aa) than LOV-1 (25% identity, 44% similarity, 14% gaps over 367 aa).
Figure 2:
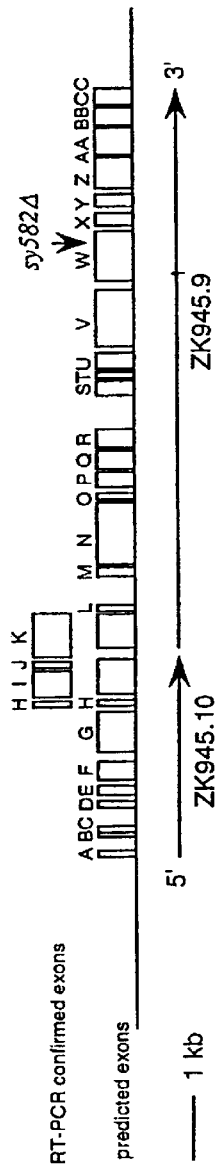
Figure 2:
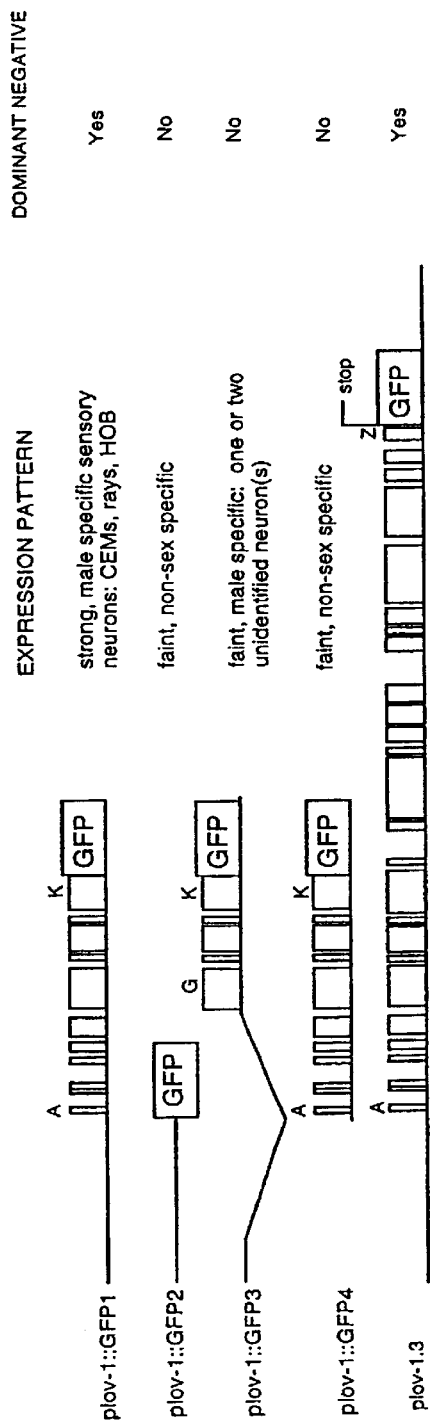
Figure 2:
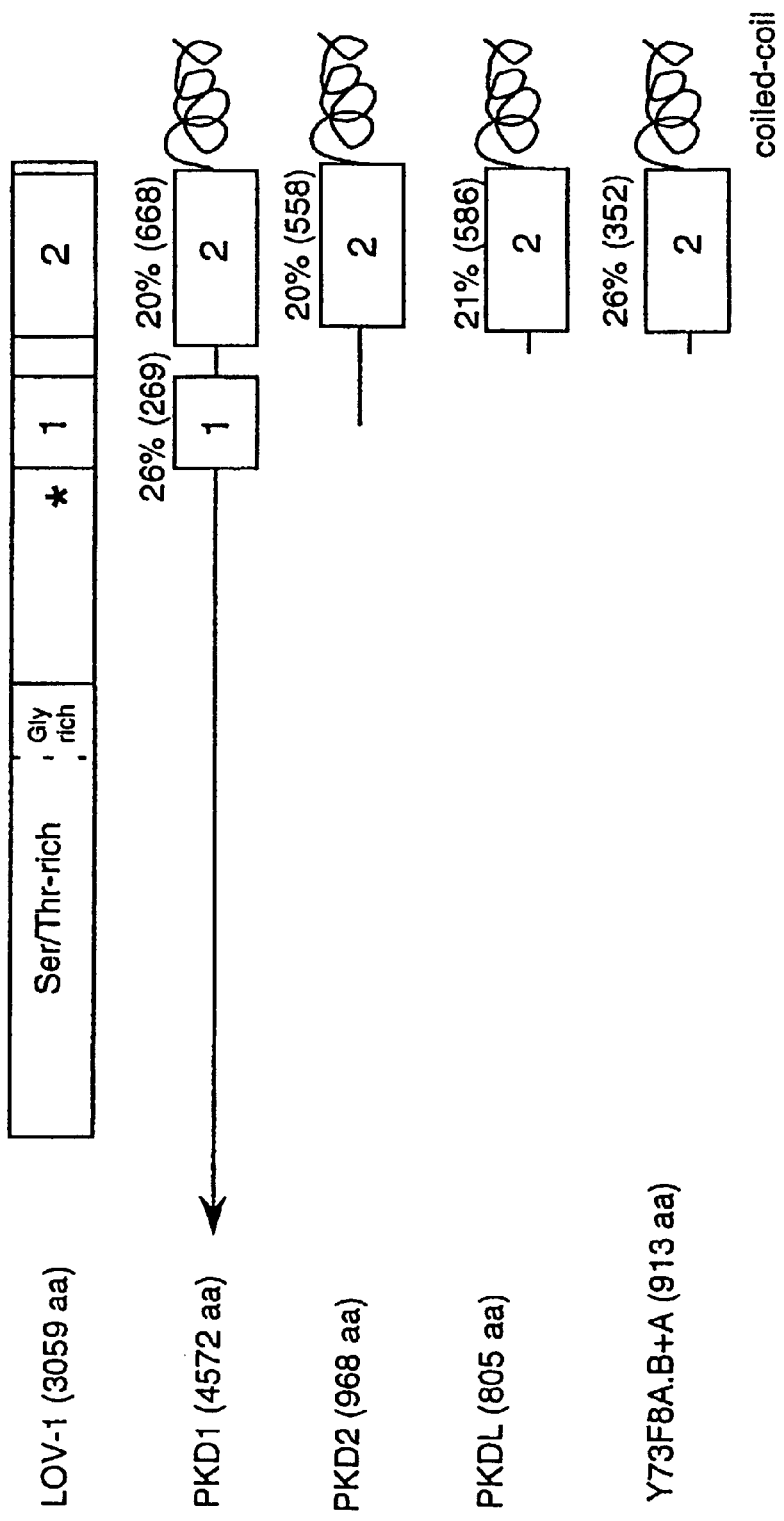

The lov-1 gene was cloned by genetic mapping and transformation rescue of the sy552 behavioral defects (FIG. 2*a*). mnDf21/sy652, mnDf83/sy552 and sy552/sy552 males are phenotypically indistinguishable; therefore, sy522 is a reduction or loss of function mutation in lov-1. This conclusion is supported by the observed recessive nature of sy552. A 16.9 kb HindIII subclone (plov-1.1) of the cosmid ZK945 rescued response and Lov defects of sy552 (FIG. 2*a*). Both a 6.7 kb HindIII-BamHI fragment from plov-1.1 (plov-1::GFP1) and a 14.1 kb HindIII-StuI frameshift in plov-1.1 (plov-1.3) fail to rescue sy552 defects (FIG. 2*b*) yet act in a dominant negative (DN) manner in wild-type males with respect to Lov behavior (FIG. 2*c*). Wild-type males expressing either plov-1::GFP or plov-1.3 are Lov defective. These transgenic males exhibit a wild-type response to hermaphrodite contact. Without being bound by a theory, the differences in sy552 and transgenic DN phenotypes might be attributed to dosage or mosaicism.

FIG. 2*b* illustrates the intron-exon boundaries of the lov-1 gene. Using RT-PCR with lov-1 specific primers and him-5 mRNA, it was found that lov-1 encodes one transcript corresponding to Genefinder-predicted ORFs, ZK945.10 and ZK945.9 (FIG. 2*b*), which had been thought to be two genes. Lov-1 encodes a predicted 3178 amino acid membrane-bound protein (see SEQ ID Nos. 3 and 4) with a serine-threonine rich extracellular domain homologous to mucins (Carraway et at (1995) *Trends Glycoscience Glycotechnology* 7:31–44), a polycystin homology block 1 (26% identity), and a carboxy terminal polycystin block 2 with 20% identity to polycystin proteins 1, 2; and 2, encoded by the PKD1, PKD2, and PKDL (polycystic kidney disease) genes, respectively (FIG. 2*d*). A Kyte-Doolittle hydropathy plot predicts multiple transmembrane domains; although no signal peptide is predicted in LOV-1. Mucins are highly glycosylated extracellular proteins thought to serve cell adhesion and/or protective functions (Carraway et al. (1995) *Trends Glycoscience Glycotechnology* 7:31–44).

Similarity between exons W (for PKD1 only), X, Y, Z, AA, BB, and CC of lov-1 and PKD1, PKD2, and the family of voltage-activated calcium and potassium channels in the six transmembrane spanning region has been observed (Mochizuki et al. (1996) *Science* 272:1339–1342). This extends to PKDL (Nomura et al. (1998) *J. BioL Chem.* 273:25967–25973). LOV-1 lacks the $Ca^{2+}$ binding EF-hand of polycystin 2 and L, and a coiled-coil domain of all three polycystins (FIG. 2*d*), which has been shown to mediate hetero- and homotypic interactions between polycystin 1 and polycystin 2 (Qian (1997) *Nature Genetics* 16:179–183; Tsiokas et al. (1997) *Proc. Natl. Acad. Sci. USA* 94:6965–6970). Block 2 also shows limited homology with the trp (transient receptor potential) family of channels (Montell et al. (1989) *Neuron* 2:1313–1323). The critical difference between voltage-gated and trp channels is the presence of a positively charged S4 transmembrane domain that acts as a voltage sensor (Montell et al. (1989) *Neuron* 2:1313–1323). LOV-1 more closely resembles voltage-gated channels in this respect. A frameshift disruption in lov-1 (plov-1.3) one residue away from a corresponding nonsense mutation in human PKD2 (Mochizuki et al. (1996) *Science* 272:1339–1342) destroys the ability to rescue lov-1(sy552), as mentioned above. The construct plov-1.3 encodes a truncated protein lacking the polycystin block 2/channel domain. These results demonstrate that the polycystin block 2/channel domain is essential for LOV-1 function, and indicate that functional as well as structural similarities might exist between LOV-1 and PKD-2. LOV-1 also possesses a nucleotide-binding domain (FIG. 2*d*) that is not present in the human polycystins. The structure of LOV-1 is also indicative of a role in signal transduction.

The lov-1 gene product appears to be a membrane spanning protein that includes an extracellular domain with a serine/threonine-rich mucin-like domain, an ATP-binding domain, and small cytoplasmic tails that mediate interaction with other members of the pathway, including a pkd-2 gene product that is also a membrane spanning protein, with six membrane domains, and a cytoplasmic EF-hand. Interaction of these proteins lead to the observed phenotypic response. In *c. elegans* this response can be detected as a clearly identifiable phenotype. Hence, c. elegans and mutants thereof can serve as a test system for identifying compounds that alter this pathway and also for identifying other gene products involved in the pathway.

lov-1 Gene

In an exemplary embodiment, the complement of the nucleic acid sequence of the lov-1 gene from C. elegans is provided. Corresponding genes from other nematodes may be identified, such as by using the nucleic acid provided herein and screening an appropriate library, genomic or cDNA library, using standard procedures. Alternatively, databases of sequence may be searched and the genes from other nematodes homologous to those provided herein identified, again using standard searching and alignment programs.

SEQ ID NO. 3 is the complement of the genomic sequence of the lov-1 gene. It includes open reading frames (ORFs) between nucleotides 15760 to 27880 of cosmid ZK945 (nucleotides 1 to 12121 of SEQ ID NO.3) and nucleotides 1–564 of cosmid F27E5 (nucleotides 12122 to 12685 of SEQ ID NO.3). It was found herein, however, that ZK945 and F27E5 overlap from nucleotides 27881 to 27981 and nucleotides 1 to 101, respectively (the overlap region includes nucleotides 12122 to 12222 in SEQ ID NO.3), thereby providing a single, rather than two, ORFs.

It been thought that the open reading frame in cosmid ZK945 (the "ZK945.9" gene; nucleotides 1 to 9164 of SEQ ID NO.3), and the open reading from in cosmid F27E5 (the "ZK945.10" gene; nucleotides 9415 to 12685 of SEQ ID NO.3) encoded two genes. DNA sequence analysis of RT-PCR generated cDNA clones from him-5(e1490) RNA revealed three exons (exons I, J and K in FIG. 2B) in the junction between ZK945.10 and ZK945.9: one from nucleotides 25195 to 25742 of the ZK945 cosmid (nucleotides 9436 to 9983 of SEQ ID NO. 3); a second from nucleotides 25071 to 25151 of the ZK945 cosmid (nucleotides 9312 to 9392 of SEQ ID NO. 3); and a third initiating at position 25021 in the ZK945 cosmid (nucleotide 9262 of SEQ ID NO. 3). This demonstrated that the lov-1 gene encodes one large transcript corresponding to ORFs in ZK945.10 and ZK945.9, spanning what had previously been thought to encode two proteins.

As noted above, FIG. 2B depicts the lov-1 genomic structure (exons shown as boxes, introns as lines). With reference to FIG. 2B, the coding sequence in the gene set forth in SEQ ID No. 3 (noting that SEQ ID 3 sets forth the non-coding strand) is as follows:

Complement (Join (12500 . . . 12685)—Exon A; (12266 . . . 12451)—Exon B; (12085 . . . 12217)—Exon C; (11683 . . . 11823)—Exon D; (11498 . . . 11637)—Exon E; (11128 . . . 11452)—Exon F; (10268 . . . 10899)—Exon G; (10138 . . . 10216)—Exon H; (9436 . . . 9983)—Exon I; (9312 . . . 9392)—Exon J; (8685 . . . 9262)—Exon K; (8557 . . . 8635)—Exon L; (7830 . . . 7997)—Exon M; (6774 . . . 7786)—Exon N; (6648 . . . 6728)—Exon O; (6305 . . . 6598)—Exon P; (6006 . . . 6255)—Exon Q; (5732 . . . 5958)—Exon R; (4849 . . . 5076)—Exon S; (4698 . . . 4799)—Exon T; (4383 . . . 4651)—Exon U; (3336 . . . 4328)—Exon V; (2229 . . . 3094)—Exon W; (1976 . . . 2181)—Exon X; (1635 . . . 1930)—Exon Y; (1043 . . . 1591)—Exon Z; (625 . . . 999)—Exon AA; (329 . . . 572)—Exon BB; (1 . . . 270)—Exon CC).

The LOV-1 amino acid sequence is set forth in SEQ ID NO. 4 The following table summarizes the above.

TABLE 3

Comparison of Sequence ID No. 3 with source Cosmids[1]

| EXON | SEQ ID 3 | ZK945 | F27E5 |
|---|---|---|---|
| A | 12500. . .12685 | | 379. . .564 |
| B | 12266. . .12451 | | 145. . .330 |
| C | 12085. . .12217 | 27844. . .27976 | |
| D | 11683. . .11823 | 27442. . .27582 | |
| E | 11498. . .11637 | 27257. . .27396 | |
| F | 11128. . .11452 | 26887. . .27211 | |
| G | 10268. . .10899 | 26027. . .26658 | |
| H | 10138. . .10216 | 25897. . .25975 | |
| *I | 9436. . .9983 | 25195. . .25742 | |
| *J | 9312. . .9392 | 25151. . .25071 | |
| *K | 8685. . .9262 | 24444. . .25021 | |
| L | 8557. . .8635 | 24316. . .24394 | |
| M | 7830. . .7997 | 23589. . .23756 | |
| N | 6774. . .7786 | 22533. . .23545 | |
| O | 6648. . .6728 | 22407. . .22487 | |
| P | 6305. . .6598 | 22064. . .22357 | |
| Q | 6006. . .6255 | 21765. . .22014 | |
| R | 5732. . .5958 | 21491. . .21717 | |
| S | 4849. . .5076 | 20608. . .20835 | |
| T | 4698. . .4799 | 20457. . .20558 | |
| U | 4383. . .4651 | 20142. . .20410 | |
| V | 3336. . .4328 | 19095. . .20087 | |
| **W | 2229. . .3094 | 17988. . .18853 | |
| X | 1976. . .2181 | 17735. . .17940 | |
| Y | 1635. . .1930 | 17394. . .17689 | |
| Z | 1043. . .1591 | 16802. . .17350 | |
| AA | 625. . .999 | 16384. . .16758 | |
| BB | 329. . .572 | 16088. . .16331 | |
| CC | 1. . .270 | 15760. . .16029 | |

*exons I, J, K at the junction of ZK946.10 and ZK945.9 (as determined by RT-PCR analysis, and not predicted by the GeneFinder program)
**the sy582 lov-1 mutant has a 1059 bp deletion beginning in exon W at position 2267 of SEQ ID NO. 3 (18026 of the ZK945 cosmid) and ending at position 1209 of SEQ ID No. 3 (16968 of the ZK945 cosmid).
[1]The GenBank accession numbers for ZK945 and F27E5 are (GenBank Accession No. Z48544) and (GenBank Accession No. Z48582), respectively.

Exemplary Knockout Mutant sy582

A genomic deletion of lov-1 in a PCR screen of EMS mutagenized worms was isolated. lov-1(sy582Δ) encodes a truncated protein lacking the polycystin/cation channel homology domain (FIG. 2d). Like sy552, lov-1(sy582Δ) males exhibit defects in response and Lov behaviors (Table 2), as well as low mating efficiency with dpy-17 but not unc-52 partners. sy582Δ is recessive and fails to complement sy552. The truncated protein produced by lov-1 (sy582Δ) does not act as a dominant negative in contrast to the truncated protein produced by plov-1.3 (see below). This difference might be due to a dosage effect of the plov-1.3 transgene. These results confirm that the polycystin block 2/cation channel domain is essential for LOV-1 activity and indicate that lov-1(sy582Δ) is completely defective in LOV-1 function.

The lov-1 (sy582) mutant is a 1059 bp deletion of nucleotides 18026 to 16968 of ZK945 (nucleotides 2267 to 1209 of SEQ ID NO. 3). The deletion, which begins in exon W, removes the majority of the PKD homology block 2 (a total of 308 amino acids, beginning at amino acid 2520 and ending at amino acid 2827 of the sequence set forth in SEQ ID NO. 4) and continues to read in-frame to the end of the sequence set forth in SEQ ID NO. 4. This results in a protein of 2870 amino acids with the amino acid sequence set forth in SEQ ID NO. 15.

Other mutants may be prepared by any method known to those of skill in the art, including directed mutagenesis of the gene in a selected nematode or random mutagenesis and selection for the altered male mating behavior in the lov and/or response, preferably both behaviors. Preferred regions for deletion include the exon A. Precise size of the deletion and or locations to delet can be determined empirically using standard routine methods based upon the disclosure herein, which identifies the gene and the resulting phenotype. Other mutations including insertions and point mutations that alter these behaviors are also contemplated and can be readily prepared.

Expression Patterns of lov-1

Figure 4:
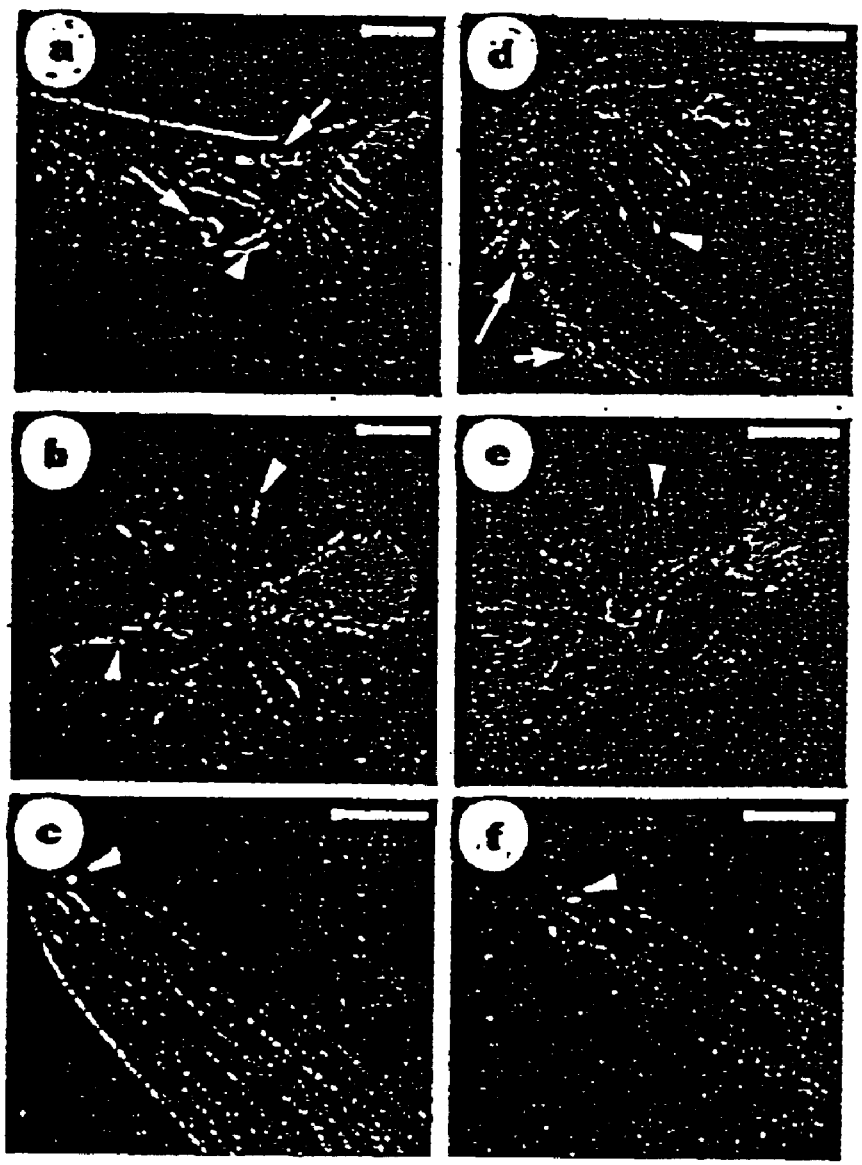
FIG. 4 shows that lov-1::GFP1 and PKD-2::GFP2 are colocalized to cell bodies and dendrites and are specifically expressed in adult male sensory neurons; the spicules, hook structure and posteriomost fan region autofluoresce; Arrows indicate neuronal cell bodies and arrowheads denote dendrites or ciliated endings. a–c lov-1::GFP1: (a) HOB and ray cell bodies (arrows), HOGB dendridic process (arrowhead); (b) HOB and ray process 5 (arrowheads); (c) Ciliated endings in nose tip from male specific cephalic CEM neurons (cell bodies not shown). d–f pkd-2::GFP2: (d) ray cell bodies (arrow) and ray process 2 (arrowhead); (e) ray process 5 (arrowhead); (f) male-specific cephalic CEM ciliated endings (arrow) Scale bar corresponds to 20 μm.

To elucidate the cells in which Mov-e acts to affect male mating behaviors, the expression pattern of lov-1-::GFP reporter genes was examined (see Example 2 and FIG. 4). These experiments reveal regulatory regions in the lov-1 gene. A partial translational fusion containing 2.8 kb of upstream sequence and 3.9 kb of lov-1 (plov-1::GFP1) directs male-specific expression in male-specific sensory neurons (FIG. 2c and FIG. 4). Conversely, shorter versions of plov-1::GFP1 are not expressed in the same set of male-specific neurons nor exclusively in male-specific sensory neurons and do not act as DNs (FIG. 2c). Similar results were observed with pkd-2 mutants (see Example 2 and FIG. 4).

Nematode pkd-2

Figure 3:
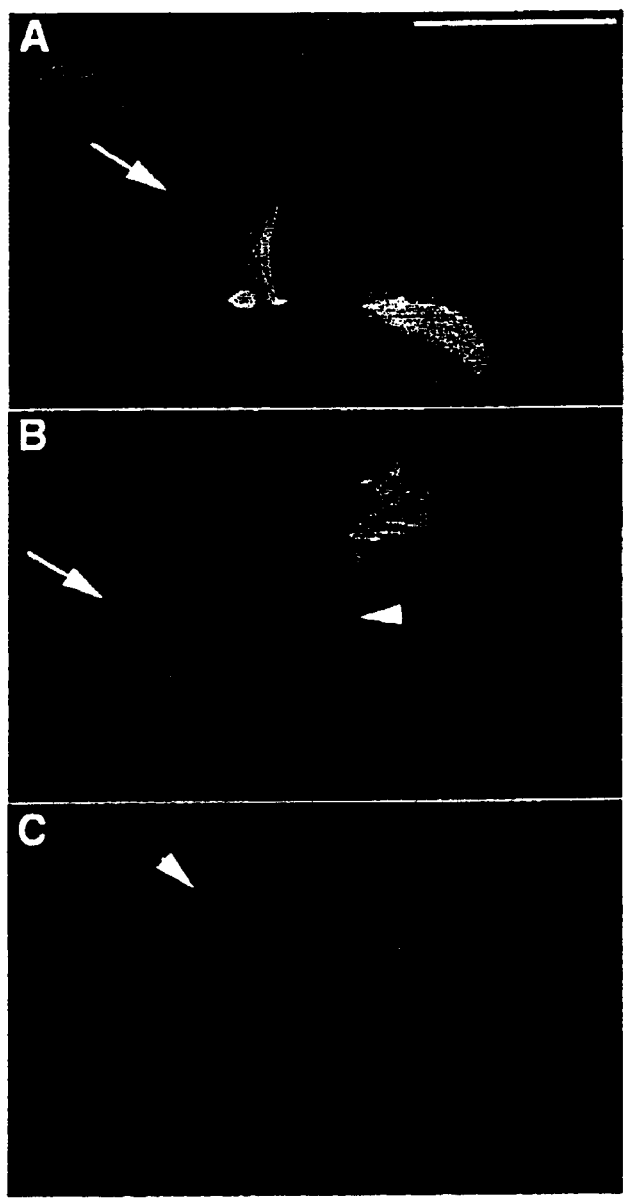
FIG. 3 shows the lov-1 and pkd-2 genomic structures, constructs, rescue date and expression patterns; the line above lov-1 indicates the 1,059 bp deletion in lov-1 (sy582Δ); numbers in parentheses indicate the ratio of rescuing stable lines to the number of stable lines examined, DN is dominant negative.

A search for a homolog of LOV-1 was performed to ascertain whether nematodes possess a PKD2 ortholog. A BLAST search of the Sanger Center C. elegans genome data base revealed a possible LOV-1 homolog, Y73F8A.B. This cosmid encodes a protein with 27% identity to PKD2 and possesses the coiled-coil domain of all polycystins. It is shown herein that Y73F8A.B and Y73F8A.A encode one transcript that is the C. elegans ortholog of human PKD2 (FIG. 2d and FIG. 3). The resulting nematode gene, designated pkd-2, cDNA and encoded protein are provided herein.

The C. elegans gene is exemplified herein. SEQ ID No. 5, which sets forth the complement of the coding strand, is provided. It contains nucleotides 1605 to 9677 of C. elegans cosmid Y73F8A (GenBank Accession No. AL132862), which correspond to nucleotides 1 to 8073 of SEQ ID No. 5. The sequence of the encoded protein is set forth in SEQ ID No. 6. FIG. 3B shows pkd-2 genomic structure (exons shown as boxes, introns as lines). The cDNA yk219e1 was sequenced and corresponds to the 3' end of pkd-2.

FIG. 3B shows the pkd-2 genomic structure (exons shown as boxes, introns as lines). The coding sequence in the gene set forth in SEQ ID No. 5 is produced as follows:

Complement (Join (7980 . . . 8073)—Exon 1; (7396 . . . 7585)—Exon 2; (6765 . . . 7045)—Exon 3; (5153 . . . 5283)—Exon 4; (4863 . . . 5104)—Exon 5; (3931 . . . 4158)—Exon 6; (2875 . . . 3424)—Exon 7; (1957 . . . 2208)—Exon 8; (1542 . . . 1795)—Exon 9; (367 . . . 505)—Exon 10; (1 . . . 87)—Exon 11.

As discussed above, the architecture of LOV-1, including a large extracellular amino terminus, Block 1, and Block 2, is similar to that of human PKD1; the architecture and sequence of PKD-2 is similar to PKD2. Taken together, LOV-1 and PKD-2 appear to be part of a multi-component complex and pathway. Further genetic analysis of Lov behavior confirms this.

Knockout Mutation of pkd-2

A knockout mutation can be prepared by any method known to those of skill in the art. A deletion mutant, designated sy606 was produced (see, Examples for primers used). A 2397 bp deletion from nucleotides 8338 to 5942, starting in intron 3 and ending in intron 5, removing exons 4 and 5 (including the partial transmembrane spanning domain S1 and the polycystin motif) with the new splice in a different reading frame resulting in a stop codon (TGA) at 5736, produced a knockout mutation. The resulting phenotype was the same as that resulting from a knockout of lov-1, thereby demonstrating that the two proteins are part of the same pathway that results in the observed phenotype.

The pkd-2 (sy606) mutant contains a 2397 bp deletion of nucleotides 8338 to 5942 of Y73F8A (nucleotides 6734 to 4338 of SEQ ID NO. 5), starting in intron 3 and ending in intron 5, removing exons 4 and 5 (including the partial transmembrane spanning domain S1 and the polycystin motif) with the new splice in a different reading frame. This results in a stop codon (TGA) at nucleotide 5728 (nucleotide 4124 in SEQ ID NO. 5). The sequence of the protein encoded by the pkd-2 deletion mutant (sy606) is set forth in SEQ ID NO. 16.

TABLE 4

Comparison of Sequence ID No. 5 with source Cosmid

| EXON | SEQ ID 5 | Y73FBA |
|---|---|---|
| 1 | 7980. . .8073 | 9584. . .9677 |
| 2 | 7396. . .7585 | 9000. . .9189 |
| 3 | 6765. . .7045 | 8369. . .8649 |
| 4 | 5153. . .5283 | 6757. . .6887 |
| 5 | 4863. . .5104 | 6467. . .6708 |
| 6 | 3931. . .4158 | 5535. . .5762 |
| 7 | 2875. . .3424 | 4479. . .5028 |
| 8 | 1957. . .2208 | 3561. . .3812 |
| 9 | 1542. . .1795 | 3146. . .3399 |
| 10 | 367. . .505 | 1971. . .2109 |
| 11 | 1. . .87 | 1605. . .1691 |

**the sv606 pkd-2 mutant has a 2397 bp deletion of nucleotides 8338 to 5942 of Y73F8A (GenBank Accession No. AL132862; nucleotides 6734 to 4338 of SEQ ID NO. 5), starting in intron 3 and ending in intron 5, removing exons 4 and 5, with the new splice being in a different reading frame and resulting in a stop codon (TGA) at nucleotide 5728 (4124 in SEQ ID NO. 5).

Other such deletions may be similarly produced by deleting any portion that eliminates at least one of the observed phenotypic behaviors associated with the lov-1 and pkd-2 pathway. Preferable targets for these deletions are those that destroy reading frame resulting in non-functional truncated proteins, deletions that eliminate transcriptional or translational control regions, deletions in the first exon or exon such that the deletion (or insertion or point mutation) eliminates or substantially attenuates activity of the encoded protein as evidenced by altered phenotype.

The lov-1 and pkd-2 Genes Encode Homologs of the Polycystins

It is shown herein that the lov-1 and pkd-2 genes and gene products are homologs of mammalian polycystins, particularly PKD1 and PKD2, respectively. As such nematodes that express these genes, and/or mutants of the genes can serve as models to study the expression of the genes, the function of these genes, to identify additional genes in the pathway, and for screening for compounds that will serve as lead compounds for treatment of PKD in mammals, particularly humans.

Neither the precise functions of the polycystins nor the molecular basis of kidney cystogenesis is known. The results provided herein show that the homologs of the polycysins act together in a pathway, that appears to be a signal transduction pathway, in sensory neurons. It has been postulated that human polycystin 1 and polycystin 2 function as an ion channel (Torres et al. (1998) Current Opinion in Nephrology and *Hypertension* 7:159–169). Further supporting this conlusion, are the results of others that have indicated that human PKD2 is associated with the activity of a cation channel. These results were obtained using cell-expression and electrophysiological approaches to examine the potential channel function of a protein called PCL (polycystin-like) that had been identified in the human expressed sequence-tag database by its sequence similarity with PKD2 (Chen et al. (1999) *Nature* 401:383–386). PCL was expressed in *Xenopus oöcytes* by microinjecting synthetic mRNA and the channel properties were studied using the two micro-electrrode voltage clamp and patch-clamp techniques. It was found that PCL is a non-selective cation channel that is permable to sodium, potassium and calcium. It is more permeable to calcium. Thus, PCL and PKD2 may be cation-channel subunits.

Hence, as shown herein, PKD1-related proteins act as receptors that regulate the activity PKD2-related proteins. The two proteins are part of a conserved pathway that appears to be a signalling mechanism in which the translocation of ions acts as a second messenger.

Exemplary Strains

Strains that exhibit one or more of the behaviors are provided. The strains may be prepared by mutagenizing wild-type or other strains with other desirable characteristics and selecting for those with the behavioral phenotype.

Strain PS3152 is an N2 strain with a deletion in lov-1 (lov-1(sy582)).

Strain PS2816 has the lov-1(sy552) deletion in a background with a him-5 (high incidence of males) and plg-1, which is a mutation that causes the male to use a gelatinous mating plug (which can be used to visualize mating).

Strain PS2817 is a paralyzed (unc-52) version of PS2816.

Strain PS3150 has the same deletion in a background with a him-5 (high incidence of males) and ts lethal marker (pha-1). A strain with a ts marker is a good recipient for transformation. strain recipient for transformation—pha-1 marker—, any marker can be PS3151 is the same as PS2815 without the plg-1

PS3149 has a pha-1 marker, in a him-5 bacground and and transforemed with an extrachromosomal element containing a lov-1::GFP1 construct and pha-1 (+) DNA.

Anbother strain is an him-5 strain with the lov-1(sy582) deletion.

PS3400 has a deletion mutation in pkd-2, it is pkd-2 (sy606).

PS3401 is a him-5 strain with the lov-1(sy582) deletion

PS3377 is pkd02(sy606) in a him-5 background.

These and other strains may be used in the assay methods described herein or in any assay that assesses the pathways and sensory functions which lov-1 and/or pkd-2 are involved or that can be used for identifying compounds that affect this pathway(s).

Assays for Screening Compounds and for Identifying Mutants With Observable Lov and/or Response Defective Behavior Assays for identifying additional genes in the pathway, to assess the activities of proteins in the pathway, to identify regulators of gene expressions and factors involved in gene expression of genes in this pathway, and for screening for compounds that affect polycystin function are provided. Compounds that affect polycystin function in a nematode are candidates for further investigation and serve as leads for compounds that may be therapeutically useful for treating mammalian PKDs.

Identification of components of the PKD pathway will aid in understanding the etiology of the disease and permit identication of disease markers and defective genes, thereby permitting development of reagents for diagnostic tests and identification of therapeutic targets and therapeutic agents.

The assays may be adapted for high throughput methods, particularly by using multiwell plates, such as 24, 96, 384 wells or higher densities, and automating many of the steps. By using multiple wells, for example, many compounds can be screened. The results can be automated by using video or other recording means to record the behavior in each well. Viewing using such means is facilitated by visually labeling the animals, such as by introduction of reporter gene constructs that will be expressed in areas of interest, such as the vulval and tail region of the hermaphrodite, to render the animal visible to a camera. If a GFP is used, for example, the camera will be equipped with an appropriate filter to screen out all but the green glow. Other ways of making the animals visible, include, for example, use of plg-1 animals, which leave a visible gelatinous trail as they move through the agar.

Precise protocols for culturing and nematodes, producing mutants and transgenics, and for observing behaviors are well known to those of skill in the art.

Assays Using Wild-type Males

Behavioral Screens

In these assays males will be identified that exhibit abnormal behavior, particularly abnormal Lov and/or response behaviors, thereby detecting components of PKD function, signaling or regulators, or identifying compounds that are candidates for affecting function, signaling or regulation. A behavioral assay is depicted in FIG. 1, and described herein.

The tests are performed by placing male nematodes on an agar surface, such as a petri dish or microtiter plate with an agar surface, that is seeded with anything, including bacteria or chemoattractants, such as NaCl, that will keep the males in a field of view. One or more mating partners, such as a hermaphrodite, is placed on the plate and the behavior is recorded, such as by direct observation, review of a video tape, or any method whereby the behavior can be recorded.

For example, observations of the behaviors can be observed using young adult hermaphrodites, such as unc-31(e169) hermaphrodites, on a lawn of bacteria, such as *E. coli*. The use of unc-31 hermaphrodites, which are sluggish, makes it easier for males to keep pace with them.

For drug screening assays, the effects of a test compound are examined. The males are treated with a compound, such as by culturing them in the presence of the compound, or including the compound in the mating dish, or pretreating the males with the compound. For analysis of mutants, males from parents or grandparents that had been mutagenized with chemical and/or radiation are tested.

In either embodiment, the behavior of the males is observed by looking for one or both, preferably both, of the Lov and 'response' behaviors compared to controls, untreated males for the drug screening assays or wild-type for the mutant assays. If behavior of the treated males differs from controls, then the compound has some activity and is selected for further analysis.

For the assays of mutants, if the behavior of the males differs from the controls, the mutation(s) are identified, such as by mapping. The mutant gene is then identified, genetically analyzed and its role in the pathway elucidated.

These methods as well as the others provided herein can be adapted for high throughput analysis, including automation, such by videotaping and image processing. For image processing the animals can be visually labeled, such as by expressing, a reporter gene, like GFP, to produce stable transgenic strain of some construct of GFP with any by promoter that would direct expression with sufficient intensity or in a sufficient number of cells to visualize the behavior. For example, a glowing vulva and tail would permit-visualization of the Lov and response behaviors. Suitable genes for linkage to a reporter are any that are expressed in the animal to permit such visualization. Such markers include, but are not limited to, autofluorescence of the male spicule, egl-5-gfp, and of the hermaphrodite vulval region lin-11-gfp.

Measurements can be performed by any method known to those of skill in the art (see, e.g., Liu et al. (1995) *Neuron* 14:79–89). Briefly, measurements can be are obtained as follows: time is kept with a stopwatch or key stroke recorder on a computer to record an 'ethogram', and distances estimated by eye and confirmed from micrographs taken of the behavior. Mating behavior is sensitive to a number of variables, including the moisture level of the plates, which are not used if they are more than a week old, hermaphrodite age. Hence controls and test animals are carefully matched. At least three hermaphrodites are used per male to control for hermaphrodite specific behaviors.

Mating Efficiency Assays

As noted above, deletion of lov-1 compromises but does not abolish the ability to mate. The mutant male can mate with paralyzed or moving impaired partners. To perform these assays, wild-type males are treated with a test compound or mutagenized, and males that sire fewer cross-progeny compared to wild-type or cannot sire cross-progeny with moving partners are identified.

To detect whether the progeny are those of the males rather than the hermaphrodites, sperm.defective hermaphrodites can be used. Preferably the hermaphrodites are temperature-sensitive (ts) sperm defective. Alternatively, the mating can be detected by using a visual marker, such as using short and fat (Dpy;Dumpy) hermaphrodites, or males that express a visually or otherwise detectable transgene, such as fluroescent proteins (FPs), including, but not limited to blue fluorescent proteins and green fluorescent proteins (GFPs), and looking for the transgene in progeny could have a transgene transferred into the progeny by the mating and detectable. If a FP is used as a marker, glowing offspring are detected.

Progeny can also be detected by measuring the density of the resulting culture and a ts sperm defective hermaphrodite. If there are lot of progeny, it can be inferred that the males have mated, since the hermaphrodite is sperm defective.

Assays Using Mutant Males

Suppressor and enhancer genetics can be used to assign functions to genes, to assign genes to pathways, to identify the key switches in these pathways and to provide a sensitive assay to identify new genes in a pathway and lead compounds that modulate the activity of genes and/or gene products in the pathway.

Suppressor screen

In these assays, the process starts with a lov-1 mutant and restoration of one or both behaviors is assessed, thereby identifying compounds or mutations that restore the defect. Restoration can occur, for example, by by-passing the defective gene, such as constitutive expression of a gene further down the pathway that had previously required lov-1 or pkd-2 activity. Alternatively, a mutation could knock-out the activity of another gene that suppresses the activity of lov-1 or pkd-2, thereby restoring the pathway. These assays will identify other genes in the pathway. These assays can also identify a compound that corrects defect in the pathway, thereby providing a promising therapeutic lead for treatment of APKD.

Enhancer screen

In these assays, the defect is exacerbated by looking for mutations or compounds that increase the penetrance of the phenotype caused by the lov-1 or pkd-2 mutations for either or both of the 'response' and Lov defect. This is achieved by screening for males that cannot sire cross progeny with paralyzed hermaphrodite mating partners or by observing the behavior directly. The genes with mutations responsible for the increased penetrance that differ are identified and those that are not lov-1 or pkd-2 are selected. Mammalian, particularly human, homologs of the selected genes are identified, and tested to assess their role in PKD diseases, such as, for example, by screening PKD patients for alterations in the homologous (or orthologous) gene, analysis of mouse model knockout mutations, or other methods known to those of skill in the art.

Assays for Identifying the Role of PKD Proteins in Sensory Function

As shown herein, lov-1 and pkd-2 are expressed in CEM neurons, indicating that they have activity in other sensory functions, such as finding a mating partner at a distance, i.e. sexual chemotaxis or kinesis, where the male randomly finds a hermaphrodite and then stays nearby. Hence sexual or chemoattraction assays can be used to study PKD function. To perform this assay, for example, put males that are mutagenized or treated with a test compound on a surface containing at particular locations hermaphrodites and a control (i.e, males, or other hermaphrodites, or buffer). The proportion of fraction of males that choose the hemnaphrodites compared to the control is scored. If the male is defective in this sensory function, it will not distinguish between males and hermaphrodites.

Other sensory functions can be assessed to identify the role, if any, of PKD genes in the functions.

Assays that Use Dominant Negative Forms of PKD in Nematodes or in Other Cells to Identify Mutations and/or Compounds That Inhibit or Otherwise Alter PKD Function Transgenic nematodes that express a version of the LOV-1 or PK2D protein that inhibits the activity of LOV-1 and/or PKD-2 as assessed by manifestation of the altered LOV and/or response phenotypic behavior(s) are used in these assays.

As described above, a dominant negative mutation is a mutation that encodes a polypeptide that when expressed disrupts that activity of the protein encoded by the wild-type gene (see, Herskowitz (1987) *Nature* 329:219–222). A cloned gene is altered so that it encodes a mutant product that upon expression in an organism or cell containing the wild-type gene, expression of the wild-type product is inhibited or eliminated. As a result, the cell or organism is deficient in the product. The mutation is "dominant" because its phenotype is manifested in the presence of the wild-type gene, and it is "negative" in the sense that it inactivates the wild-type gene function. It is possible to do this because proteins have multiple functional sites. Hence an assay that identifies a dominant negative mutation can identify functional activities of a protein.

In this instance, the assays use transgenic nematodes that contain such a dominant negative lov-1 or pkd-2 transgene. In certain assays, the transgenic mutants are mutagenized, and mutants that lose a remaining activity are selected. The mutuations and genes responsible for the loss are identified. Corresponding mammalian, particularly human, genes, such as by searching databases for homologs or by probing libraries with the nematode genes, are identified.

In the compounds screening assays that employ these transgenic nematodes, compounds that interfere with a remaining activity of the lov-1 or pkd-2 gene are identified. For example, as shown herein, plov-1.3 (plov-1.3 encodes a truncated protein lacking the polycystin block 2/channel domain) has a dominant negative effect in transgenic nematodes affecting only the Lov behavior, not Response. Compounds that rescue this dominant negative effect include those that interfere with the synthesis, binding or function of the amino-terminal region of the LOV-1 protein.

Since the dominant negative effect only affects the Lov response, a stable transgenic nematode strain that expresses a dominant negative of lov-1, can be used to screen for compounds and mutations that further affect Response well.

Assays Based on Localization and Trafficking of LOV-1 and/or PKD-2 Within a Cell or Cells To identify regulators and factors necessary for synthesis and transport of LOV-1 and/or PKD-2 proteins, strains in which LOV-1 and PKD-2 are expressed linked to a detectable label, such as a fluorescent protein, can be and have been produced. It has been shown that these proteins are expressed in the ciliated endings and in the baso-dendritic compartment of HOB, ray neurons or CEM neurons.

These strains, such as PS3149, described above, can be used to study the trafficking patterns of LOV-1 and PKD-2 and cellular location(s) of the proteins in the animal by looking for mutants thereof that have altered trafficking and/or altered localization of one or both of these proteins. The mutations can be mapped, genetically analyzed and the genes identified. Such genes could serve as therapeutic or diagnostic targets.

Assays for Identification of Transcriptional Regulators of Expression of lov-1 and/or pkd-2

To identify transcriptional regulators of lov-1 or pkd-2, a screen for loss or alteration of expression of either gene is provided. Transgenic nematodes with a reporter gene, such as a gene encoding a FP or lacZ or other detectable product, linked to the nucleic acid encoding lov-1 or pkd-2 is used. The animal is mutagenized or treated with a test compound and loss of expression or reduction in expression of either gene is assessed by detecting, such as by observing under a dissecting or compound microscope or other means, including whole animal sorting, the number of cells that express the detectable marker, such as a FP.

As a control, to avoid detection or identification of non-specific effects, an unrelated gene, such as lin-3, linked to a reporter, is expressed in other cells in these animals. Only mutants that exhibit changes in expression of lov-1 or pkd-2, but not expression of the other gene, are selected for identification and mapping of the mutation. If expression of the other gene is affected also, then mutation is likely affecting a general process and would not be of interest.

These assays will identify regulators of and factors that affect lov-1 and pkd-2 expression, which regulators and factors could serve as therapeutic or diagnostic targets, or which can aid in developing an understanding of the development and progression of PKD in mammals.

Visual Screen Based on Clumping Behavior

Wild type adult males isolated from hermaphrodites will clump together on a plate with a lawn of bacteria. In contrast, lov-1 and pkd-2 mutant males do not exhibit this clumping behavior. Rather, lov-1 and pkd-2 mutant males are randomly dispersed in the bacterial lawn. This assay may be used for a variety of purposes, including, but not limited to, the identification of compounds that inhibit wild type male clumping behavior, compounds that restore clumping behavior to lov-1 or pkd-2 mutants, and the identification of genetic supressors of lov-1 or pkd-2 mutants.

Kits and Diagnostic Systems for Performing the Assays

Kits for use in screening for use in any of the assays are provided.

The kits include transgenic or wild-type nematodes or both that express either wild-type or a mutant or a transgenic form of lov-1 and/or pkd-2. The nematodes may be on plates, in wells or in any form suitable for the assays. Kits containing nucleic acid encoding either of the two genes, portions thereof or vectors or plasmid containing the nucleic acids or probes based upon these sequences or reporter gene constructs containing all or portions of either or both genes and a reporter molecule are also provided. The nucleic acids may be in solution, in lyophilized or other concentrated form, or may be bound to a suitable substrate. The kits can include additional reagents for performing the assays, such reagents include any for performing any of the steps of the methods. The kits include instructions for performing the assays.

The kits may also include suitable ancillary reagents, such as the appropriate buffers and reagents. The kits may also include suitable ancillary supplies, such as microtiter plates, vials, calibrator solutions, controls, wash solutions and solid-phase supports.

The kits are typically provided in packages customarily utilized in diagnostic assays. Such packages include glass and plastic, such as polyethylene, polypropylene and polycarbonate, bottles and vials, plastic and plastic-foil laminated envelopes and the like. The packages may also include containers appropriate for use in auto analyzers. The packages a typically include instructions for performing the assays.

The following examples are included for illustrative purposes only and are not intended to limit the scope of the invention.

EXAMPLE 1

Identification of *C. elegans* Orthologs of Human Polycystins

Mating behavior and mating efficiency assays. Males were generated by use of him-5(e1490) (high incidence of male) strains or by heatshock of L4 hermaphrodites (Brenner (1974) *Genetics* 77:71–94). Mating efficiency (ME) tests were performed by pairing six tester L4 males with six paralyzed unc-52 or four actively moving dpy-17 or N2 L4 hermaphrodites. ME is the percentage of cross progeny to total progeny (Hodgkin (1983) *Genetics* 103:43–64). Behavioral observations were done on a 0.5 cm diameter lawn of OP50 (Liu et al. *Neuron* 14:79–89). Hermaphrodites (N2 or unc-31(e169)) were placed on a lawn with the tester male. Behavioral phenotypes were determined by keeping time with a stopwatch and manually recording the behavioral series. In one trial, a male is observed for a minimum of 10 vulva encounters or for 10 minutes, whichever comes first. A male who does not respond to hermaphrodite contact within 10 minutes is considered response defective. Response ability reflects the percentage of males successfully responding to hermaphrodite contact. An individual male's vulva location ability was calculated as: Number of positive vulva locations/Total number of vulva encounters. Ability can vary from 100% (always locate) to 0% (never locate). Vulva location efficiency indicates the average behavior of a genotypic population. Pairwise comparisons were made using Mann-Whitney nonparametric and two-sided t tests (Instat for Macintosh).

Genetic screen for location of vulva (Lov mutants). PS1395 hermaphrodites of genotype plg-1(e2001d); him-5 (e1490) were mutagenized with EMS (Brenner (1974) *Genetics* 77:71–94). plg-1(e2001d); him-5(e1490) males deposit a gelatinous plug over the hermaphrodite vulva post coitum. A decrease in plugging efficiency might reflect a decrease in mating ability. An F1 clonal screen was performed by picking individual F1 progeny of mutagenized hermaphrodites to individual plates and directly observing F2 males for behavioral defects. An F2 clonal screen was performed such that 10 F1 progeny per P0 hermaphrodite were picked to the same plate, 10 F2 hermaphrodites per F1 pool were picked to individual plates, and F3 males were observed for decreased plugging efficiency and/or location of vulva (Lov) defects. lov-1(sy552); plg-1(e2001d); him-5 is a recessive mutation isolated in the F2 clonal screen. lov-1(sy552) males are response and Lov defective and also have a very low ME with dpy-17 hermaphrodites (ME-Dpy).

Genetic mapping of lov-1. Chromosomal linkage of lov-1(sy552) was determined by scoring the loss of genetic markers relative to response, Lov, and ME-Dpy phenotypes, which revealed linkage between dpy-10 and sy552. Further mapping was achieved via three factor crosses. From sy552/unc-4(e120) let-25(mn25) heterozygotes, Unc non-Let (Unc for uncoordinated, Let for lethal) recombinants were picked. As Unc males cannot mate, a test cross with sy552 males and Unc hermaphrodites was performed to generate non-Unc sy552/(sy552Δ)unc-25(mn25) males. Males were scored for response, Lov, and ME-Dpy defects. 2/12 Unc non-Let recombinants segregate the lov-1 mutant phenotype. These data placed lov-1 between unc-4 and let-25, closer to unc-4. Deficiency mapping indicated that mnDf21 uncovers sy552 whereas eDf21 does not.

Transformation rescue of lov-1(sy552) mutants. Cosmids and plasmids (15–100 ng/μl) in the region from the right breakpoint of eDf21 to the right breakpoint of mnDf21 and PHA-1 (pBX, 100 ng/μl were injected into lov-1(sy552); pha-1(e2123ts); htm-5(e14901. Stable lines were selected at either 19° or 25° C. (Schnabel et al. (1990) *Science* 250:686–688). Cosmid ZK945 rescued sy552 response and vulva location defects in four of five stable lines. A 16.9 kb HindIII fragment of ZK945 cloned into pBS(SK+) (plov1.1) containing ORFs ZK945.10 and ZK945.9 rescued sy552 behavioral defects in 4 of 6 stable lines. A 6.7 kb HindIII-BamHI fragment of ZK945 (plov-1::GFP1) containing ORF ZK945.10 did not rescue sy552 defects. plov-1.3 creates a frameshift at nucleotide 17724 in ZK945 inserting a BssHII GFP fragment from plasmid pPD95.02 out of frame into the StuI site of plov-1.1 plov-1.3 fails to rescue sy552.

PCR screen for genomic deletion of lov-1. Approximately 315,000 haploid genomes were screened using primers designed to delete the PKD/channel domain. Primer set 1 (SEQ ID Nos. 7 and 8, respectively), the outside primers were:

JC32 5'-CTCTATTTGTGGTTCGTTGGCG-3' and

JC36 5'-GGGAGTTTCCGTTTTCATGGGG-3'; and internal nested primer set (SEQ ID Nos. 9 and 10, respectively) were:

JC33 5'-CTAGGACCGATGCAACAGCGAG-3' and

JC35 5'-AACGCTGATTGGTTCAAGTGTG-3')

are approximately 2.5 and 2.4 kb apart, respectively. One deletion allele, lov-1(sy582Δ) was isolated. DNA sequence analysis indicated a deletion of nucleotides 16972 to 18027 of ZK945.

DNA-sequence analysis. RT-PCR from him-5(e1490) RNA using a combination of lov-1 primers generated overlapping cDNA clones bridging the junction between ZK945.10 and ZK945.9. Genefinder had predicted boundaries of the last exon of ZK945.10 (from position 25742 to 25174 of ZK945) and first exon of ZK945.9 (24923 to 24444). DNA sequence analysis of RT-PCR generated cDNA clones revealed three exons in the junction: one from 25742 to 25195, a second from 25151 to 25071, and a third initiating a position 25021, corresponding to exons 1, J, and K, in FIG. 2b, respectively.

PCR Screen for Genomic Deletion of pkd-2

For pkd-2 the used primers (SEQ ID Nos. 11–14, respectively) were as follows:

Outside Primers

LOV2.9 (Y73F8A nt 8546–8569) 5' CCCCTCGTTTGACCATTCTATGG 3'

LOV2.10 (Y73F8A nt 8438–8457) 5' ACGTGATCCTCT-GTCGATCCAG 3'

Nested Primers

LOV2.9A(Y73F8A nt 5599–5615) 5' AGATCAAGCT-GACTGCCCGTTC 3'

LOV2.10A(Y73F8A nt 5609–5631) 5' GATCCAGC-GATTAGCCTTTAA CG3'/One deletion allele, pkd-2 (sy606) was isolated, which has a 2397 bp deletion from nucleotides 8338 to 5942 of Y73F8A (GenBank Accession No. AL132862; corresponding to nucleotides 6734 to 4338 of SEQ ID NO. 5). The deletion starts in intron 3 and ends in intron 5, removing exons 4 and 5 (including the partial transmembrane spanning domain S1 and the polycystin motif) with the new splice in a different reading frame resulting in a stop codon (TGA) at 5736, produced a knockout mutation. The resulting phenotype was the same as that resulting from a knockout of lov-1, thereby demonstrating that the two proteins are part of the same pathway that results in the observed phenotype.

EXAMPLE 2

Expression Analyses of LOV-1 and PKD-2

Methods

GFP (see, Chalfie et al. (1994) *Science* 263:802–805) expression was used a marker for lov-1 and pkd-2 gene expression (see FIGS. 3a and 4A) plov-1::GFP1 was constructed by cloning a 6.7 kb HindIII-BamHI fragment of plov-1.1 into the vector pPD95.81, plov-1::GFP2 by cloning a HindIII-HpaI fragment. plov-1::GFP3 and plov-1::GFP4 are SacI and HindIII-HpaI (Klenow filled-in and religated) deletions of plov-1::GFP1, respectively, plov-1::GFP5 was constructed by cloning a 15.4 kb HindIII-AfeI fragment of plov-1.1 into the HindIII-SmaI site of pPD95.79. ppkd-2.1, ppkd-2::gfp1 and ppkd-2::gfp2 were constructed by cloning PCR-amplified 8.9 kb, 2.0 kb and 5.9 kb fragments into the vectors pPD95.97, pPD95.75 and pPD95.77, respectively. Transgenic animals were observed by fluorescence microscopy Cells were identified by comparing Nomarski and fluorescent or confocal images of the same animals to determine cell-body position (Sulston et al. (1980) *Dev. Biol.* 78:542–576). HOB assignment was confirmed by laser ablation of precursor cells.

lov-1 Expression lov-1::GFP1 is specifically expressed in male-sensory neurons, including four putative chemosensory CEM cephalic neurons, the hook neuron HOB (FIG. 4a), and the sensory ray neurons (FIG. 4b). lov-1::GFP1 expression was first observed in a few cells during late L4 lethargus (data not shown) while strong expression peaks in the adult male. In neuronal cell bodies, GFP expression is cytoplasmic (non-nuclear) and punctate (FIG. 4a and FIG. 4b). lov-1::GFP1 is localized at high levels in the cell body and ciliated endings of CEM (FIG. 4c), HOB, and ray neurons (FIG. 4b) but is not observed in axons. Localization of lov-1::GFP1 to sensory endings is consistent with plasma membrane localization and strengthens the argument that lov-1 mediates sensory perception required for mating behaviors. The temporal and spatial regulation of lov-1 is concordant with its role in adult male mating behavior. Rays mediate response to contact with a hermaphrodite (Liu et al. *Neuron* 14:79–89), the hook mediates vulva location (Liu et al. *Neuron* 14:79–89), and the CEMs are postulated to play a role in chemosensation (Ward et al. (1975) *J. Comp. Neurol.* 160:313–337).

lov-1::GFP1 expression was unaltered in lov-1(sy552) mutants. Expression of this fusion gene did not rescue lov-1(sy552) defects (FIG. 2a) and is therefore not functional. Sensory neurons and structures are normal in lov-1 (sy552) mutants as determined by osm-6::gfp expression, dye filling of sensory neurons, Nomarski observation, and SEM imaging (data not shown). The defects of lov-1(sy552) mutants therefore cannot be attributed to abnormal development or differentiation of the response and vulva location neurons. This indicates hat lov-1 (sy552) defects are due to defects in the function of the cells required for response and vulva location.

The Lov defect of mutations in lov-1 is not identical to ablation of HOB, the chemosensory neuron in which lov-1 expressed. The lov-1 mutant and HOB-ablated males pass the vulva (FIG. 1). The lov-1 males, however, are capable of precisely locating the vulva, whereas HOB-ablated males resort to slow search. Therefore, the HOB neuron of lov-1 functions, albeit in an attenuated capacity. If lov-1(sy552) and lov-1(sy582Δ) are loss of function alleles as the data suggests, then additional components are involved in Lov sensation.

Chemosensation and mechanosensation are likely involved in Lov *C elegans* sensory neurons can be polymodal: for example, by ultrastructural assignment, the ASH neuron appears to be chemosensory yet functions in both mechanosensory (nose touch) and chemosensory (osmotic avoidance) modalities (Kaplan et al. (1993) *Proc. Natl. Acad. Sci. U.S.A.* 90:2227–2231). HOB might similarly be a polymodal sensory neuron. Ablation of either HOA or HOB produces identical phenotypes (Liu et al. *Neuron* 14:79–89) and HOA and HOB form multiple chemical synapses and electrical junctions (Sulston et al. (1980) *Dev. Biol.* 78:542–576), indicating extensive cross talk between the two hook sensory neurons. Since LOV-1 has an extensive extracellular mucin-like domain that could be involved in cell-cell or cell-matrix interaction, binding of vulva cell ligand(s) might potentially gate the LOV-1 polycystin-related channel. Another possibility is that LOV-1 could physically link the HOB sensory endings to the scherotized hook structure and couple hook deflection by the hermaphrodite vulva to intracellular voltage-activated signaling similar to hair cell mechanosensation (Hudspeth (1989) *Nature* 341:397–404) or touch response in *C. elegans* (Driscoll et a/. in *C. elegans II* (ed. Riddle, D. I., Blumenthal, T., Meyer, B. J., and Priess, J. R.) 645–677 (Cold Spring Harbor Laboratory Press, New York, 1997).

pkd-2 Expression

As shown herein, *C. elegans* genome contains a human PKD-2 homolog. PKD-2 possesses six membrane-spanning domains, a positively charged foruth membrane-spanning segment, a pore region, and the coiled coil domain of all polysystins. PKD-2 is localized to the same male-specific sensory neurons as LOV-1 (see, FIG. 3 and FIG. 4).

Since modifications will be apparent to those of skill in this art, it is intended that this invention be limited only by the scope of the appended claims.

SEQUENCE LISTING SUMMARY

SEQ ID No. 1 cDNA encoding human PKD1
SEQ ID No. 2 encoded human PKD1 protein
SEQ ID No. 3 sequence of a gene encoding nematode LOV-1 protein
SEQ ID No. 4 encoded nematode LOV-1 protein
SEQ ID No. 5 sequence of a gene encoding a nematode PKD-2 protein
SEQ ID No. 6 encoded nematode PKD-2 protein
SEQ ID No. 7 primer for lov-1 deletion mutant construction
SEQ ID No 8 primer for lov-1 deletion mutant construction
SEQ ID No. 9 internal primer for lov-1 deletion mutant construction
SEQ ID No. 10 internal primer for lov-1 deletion mutant construction
SEQ ID No. 11 primer for pk2-1 deletion mutant construction
SEQ ID No. 12 primer for pk2-1 deletion mutant construction
SEQ ID No. 13 internal primer for pk2-1 deletion mutant construction
SEQ ID No. 14 internal primer for pk2–1 deletion mutant construction
SEQ ID No. 15 sets forth the a LOV-1 mutant protein from sy582
SEQ ID No. 16 sets a PKD-2 mutant protein from sy606

What is claimed is:

1. A construct comprising an isolated nucleic acid molecule operatively linked to a reporter gene, wherein the nucleic acid molecule comprises a sequence of nucleotides selected from the group consisting of:
   a) a sequence of nucleotides that encodes a Caenorhabditis LOV-1 protein and that encodes the sequence of amino acids encoded by the full length complement of the sequence of nucleotides set forth in SEQ ID No. 3; and
   b) a sequence of nucleotides that is the full length complement of a sequence of nucleotides set forth in SEQ ID No. 3 and that encodes a Caenorhabditis LOV-1 protein, or full length complement thereof.

2. The construct of claim 1, wherein the reporter gene encodes a fluorescent protein.

3. A plasmid comprising an isolated nucleic acid molecule comprising a sequence of nucleotides selected from the group consisting of:
   a) a sequence of nucleotides that encodes a Caenorhabditis LOV-1 protein and that encodes the sequence of amino acids encoded by the full length complement of the sequence of nucleotides set forth in SEQ ID No. 3; and
   b) a sequence of nucleotides that is the full length complement of a sequence of nucleotides set forth in SEQ ID No. 3 and that encodes a Caenorhabditis LOV-1 protein, or full length complement thereof.

4. The plasmid of claim 3 that is an expression vector.

5. An isolated nucleic acid molecule that encodes a mutant Caenorhabditis LOV-1 protein comprising a sequence of nucleotides, or full length complement thereof, that encodes the sequence of amino acids set forth in SEQ ID NO. 15, wherein:

a *Caenorhabditis elegans* nematode expressing the mutant protein exhibits defective mating behavior; and a nematode that expresses such defect exhibits one or both of an altered location of vulva (Lov) and response phenotype.

6. An isolated nucleic acid molecule comprising the nucleotide sequence set forth in SEQ ID NO: 3.

* * * * *

SEQUENCE LISTING

```
<160> NUMBER OF SEQ ID NOS:    16

<210> SEQ ID NO 1
<211> LENGTH: 12912
<212> TYPE: DNA
<213> ORGANISM: Homo sapiens PKD-1 gene
<220> FEATURE:
<221> NAME/KEY: CDS
<222> LOCATION: (1)..(12912)

<400> SEQUENCE: 1 atg ccg ccc gcc gcg ccc gcc cgc ctg gcg ctg gcc ctg ggc ctg ggc      48
Met Pro Pro Ala Ala Pro Ala Arg Leu Ala Leu Ala Leu Gly Leu Gly
  1               5                  10                  15
```

```
ctg tgg ctc ggg gcg ctg gcg ggg ggg ccc ggg cgc ggc tgc ggg ccc      96
Leu Trp Leu Gly Ala Leu Ala Gly Gly Pro Gly Arg Gly Cys Gly Pro
         20                  25                  30 tgc gag ccc ccc tgc ctc tgc ggg cca gcg ccc ggc gcc gcc tgc cgc     144
Cys Glu Pro Pro Cys Leu Cys Gly Pro Ala Pro Gly Ala Ala Cys Arg
     35                  40                  45 gtc aac tgc tcg ggc cgc ggg ctg cgg acg ctc ggt ccc gcg ctg cgc     192
Val Asn Cys Ser Gly Arg Gly Leu Arg Thr Leu Gly Pro Ala Leu Arg
 50                  55                  60 atc ccc gcg gac gcc aca gag cta gac gtc tcc cac aac ctg ctc cgg     240
Ile Pro Ala Asp Ala Thr Glu Leu Asp Val Ser His Asn Leu Leu Arg
 65                  70                  75                  80 gcg ctg gac gtt ggg ctc ctg gcg aac ctc tcg gcg ctg gca gag ctg     288
Ala Leu Asp Val Gly Leu Leu Ala Asn Leu Ser Ala Leu Ala Glu Leu
             85                  90                  95 gat ata agc aac aac aag att tct acg tta gaa gaa gga ata ttt gct     336
Asp Ile Ser Asn Asn Lys Ile Ser Thr Leu Glu Glu Gly Ile Phe Ala
            100                 105                 110 aat tta ttt aat tta agt gaa ata aac ctg agt ggg aac ccg ttt gag     384
Asn Leu Phe Asn Leu Ser Glu Ile Asn Leu Ser Gly Asn Pro Phe Glu
        115                 120                 125 tgt gac tgt ggc ctg gcg tgg ctg ccg caa tgg gcg gag gag cag cag     432
Cys Asp Cys Gly Leu Ala Trp Leu Pro Gln Trp Ala Glu Glu Gln Gln
130                 135                 140 gtg cgg gtg gtg cag ccc gag gca gcc acg tgt gct ggg cct ggc tcc     480
Val Arg Val Val Gln Pro Glu Ala Ala Thr Cys Ala Gly Pro Gly Ser
145                 150                 155                 160 ctg gct ggc cag cct ctg ctt ggc atc ccc ttg ctg gac agt ggc tgt     528
Leu Ala Gly Gln Pro Leu Leu Gly Ile Pro Leu Leu Asp Ser Gly Cys
                165                 170                 175 ggt gag gag tat gtc gcc tgc ctc cct gac aac agc tca ggc acc gtg     576
Gly Glu Glu Tyr Val Ala Cys Leu Pro Asp Asn Ser Ser Gly Thr Val
            180                 185                 190 gca gca gtg tcc ttt tca gct gcc cac gaa ggc ctg ctt cag cca gag     624
Ala Ala Val Ser Phe Ser Ala Ala His Glu Gly Leu Leu Gln Pro Glu
        195                 200                 205 gcc tgc agc gcc ttc tgc ttc tcc acc ggc cag ggc ctc gca gcc ctc     672
Ala Cys Ser Ala Phe Cys Phe Ser Thr Gly Gln Gly Leu Ala Ala Leu
    210                 215                 220 tcg gag cag ggc tgg tgc ctg tgt ggg gcg gcc cag ccc tcc agt gcc     720
Ser Glu Gln Gly Trp Cys Leu Cys Gly Ala Ala Gln Pro Ser Ser Ala
225                 230                 235                 240 tcc ttt gcc tgc ctg tcc ctc tgc tcc ggg ccc ccg gca cct cct gcc     768
Ser Phe Ala Cys Leu Ser Leu Cys Ser Gly Pro Pro Ala Pro Pro Ala
                245                 250                 255 ccc acc tgt agg ggc ccc acc ctc ctc cag cac gtc ttc cct gcc tcc     816
Pro Thr Cys Arg Gly Pro Thr Leu Leu Gln His Val Phe Pro Ala Ser
            260                 265                 270 cca ggg gcc acc ctg gtg ggg ccc cac gga cct ctg gcc tct ggc cag     864
Pro Gly Ala Thr Leu Val Gly Pro His Gly Pro Leu Ala Ser Gly Gln
        275                 280                 285 cta gca gcc ttc cac atc gct gcc ccg ctc cct gtc act gac aca cgc     912
Leu Ala Ala Phe His Ile Ala Ala Pro Leu Pro Val Thr Asp Thr Arg
    290                 295                 300 tgg gac ttc gga gac ggc tcc gcc gag gtg gat gcc gct ggg ccg gct     960
Trp Asp Phe Gly Asp Gly Ser Ala Glu Val Asp Ala Ala Gly Pro Ala
305                 310                 315                 320 gcc tcg cat cgc tat gtg ctg cct ggg cgc tat cac gtg acg gcc gtg    1008
Ala Ser His Arg Tyr Val Leu Pro Gly Arg Tyr His Val Thr Ala Val
                325                 330                 335
```

```
ctg gcc ctg ggg gcc ggc tca gcc ctg ctg ggg aca gac gtg cag gtg      1056
Leu Ala Leu Gly Ala Gly Ser Ala Leu Leu Gly Thr Asp Val Gln Val
            340                 345                 350 gaa gcg gca cct gcc gcc ctg gag ctc gtg tgc ccg tcc tcg gtg cag      1104
Glu Ala Ala Pro Ala Ala Leu Glu Leu Val Cys Pro Ser Ser Val Gln
            355                 360                 365 agt gac gag agc ctc gac ctc agc atc cag aac cgc ggt ggt tca ggc      1152
Ser Asp Glu Ser Leu Asp Leu Ser Ile Gln Asn Arg Gly Gly Ser Gly
    370                 375                 380 ctg gag gcc gcc tac agc atc gtg gcc ctg ggc gag gag ccg gcc cga      1200
Leu Glu Ala Ala Tyr Ser Ile Val Ala Leu Gly Glu Glu Pro Ala Arg
385                 390                 395                 400 gcg gtg cac ccg ctc tgc ccc tcg gac acg gag atc ttc cct ggc aac      1248
Ala Val His Pro Leu Cys Pro Ser Asp Thr Glu Ile Phe Pro Gly Asn
                405                 410                 415 ggg cac tgc tac cgc ctg gtg gtg gag aag gcg gcc tgg ctg cag gcg      1296
Gly His Cys Tyr Arg Leu Val Val Glu Lys Ala Ala Trp Leu Gln Ala
            420                 425                 430 cag gag cag tgt cag gcc tgg gcc ggg gcc gcc ctg gca atg gtg gac      1344
Gln Glu Gln Cys Gln Ala Trp Ala Gly Ala Ala Leu Ala Met Val Asp
            435                 440                 445 agt ccc gcc gtg cag cgc ttc ctg gtc tcc cgg gtc acc agg agc cta      1392
Ser Pro Ala Val Gln Arg Phe Leu Val Ser Arg Val Thr Arg Ser Leu
    450                 455                 460 gac gtg tgg atc ggc ttc tcg act gtg cag ggg gtg gag gtg ggc cca      1440
Asp Val Trp Ile Gly Phe Ser Thr Val Gln Gly Val Glu Val Gly Pro
465                 470                 475                 480 gcg ccg cag ggc gag gcc ttc agc ctg gag agc tgc cag aac tgg ctg      1488
Ala Pro Gln Gly Glu Ala Phe Ser Leu Glu Ser Cys Gln Asn Trp Leu
                485                 490                 495 ccc ggg gag cca cac cca gcc aca gcc gag cac tgc gtc cgg ctc ggg      1536
Pro Gly Glu Pro His Pro Ala Thr Ala Glu His Cys Val Arg Leu Gly
            500                 505                 510 ccc acc ggg tgg tgt aac acc gac ctg tgc tca gcg ccg cac agc tac      1584
Pro Thr Gly Trp Cys Asn Thr Asp Leu Cys Ser Ala Pro His Ser Tyr
            515                 520                 525 gtc tgc gag ctg cag ccc gga ggc cca gtg cag gat gcc gag aac ctc      1632
Val Cys Glu Leu Gln Pro Gly Gly Pro Val Gln Asp Ala Glu Asn Leu
            530                 535                 540 ctc gtg gga gcg ccc agt ggg gac ctg cag gga ccc ctg acg cct ctg      1680
Leu Val Gly Ala Pro Ser Gly Asp Leu Gln Gly Pro Leu Thr Pro Leu
545                 550                 555                 560 gca cag cag gac ggc ctc tca gcc ccg cac gag ccc gtg gag gtc atg      1728
Ala Gln Gln Asp Gly Leu Ser Ala Pro His Glu Pro Val Glu Val Met
                565                 570                 575 gta ttc ccg ggc ctg cgt ctg agc cgt gaa gcc ttc ctc acc acg gcc      1776
Val Phe Pro Gly Leu Arg Leu Ser Arg Glu Ala Phe Leu Thr Thr Ala
            580                 585                 590 gaa ttt ggg acc cag gag ctc cgg cgg ccc gcc cag ctg cgg ctg cag      1824
Glu Phe Gly Thr Gln Glu Leu Arg Arg Pro Ala Gln Leu Arg Leu Gln
            595                 600                 605 gtg tac cgg ctc ctc agc aca gca ggg acc ccg gag aac ggc agc gag      1872
Val Tyr Arg Leu Leu Ser Thr Ala Gly Thr Pro Glu Asn Gly Ser Glu
            610                 615                 620 cct gag agc agg tcc ccg gac aac agg acc cag ctg gcc ccc gcg tgc      1920
Pro Glu Ser Arg Ser Pro Asp Asn Arg Thr Gln Leu Ala Pro Ala Cys
625                 630                 635                 640 atg cca ggg gga cgc tgg tgc cct gga gcc aac atc tgc ttg ccg ctg      1968
Met Pro Gly Gly Arg Trp Cys Pro Gly Ala Asn Ile Cys Leu Pro Leu
```

```
                    645                 650                 655
gac gcc tcc tgc cac ccc cag gcc tgc gcc aat ggc tgc acg tca ggg      2016
Asp Ala Ser Cys His Pro Gln Ala Cys Ala Asn Gly Cys Thr Ser Gly
            660                 665                 670 cca ggg cta ccc ggg gcc ccc tat gcg cta tgg aga gag ttc ctc ttc      2064
Pro Gly Leu Pro Gly Ala Pro Tyr Ala Leu Trp Arg Glu Phe Leu Phe
        675                 680                 685 tcc gtt ccc gcg ggg ccc ccc gcg cag tac tcg gtc acc ctc cac ggc      2112
Ser Val Pro Ala Gly Pro Pro Ala Gln Tyr Ser Val Thr Leu His Gly
    690                 695                 700 cag gat gtc ctc atg ctc cct ggt gac ctc gtt ggc ttg cag cac gac      2160
Gln Asp Val Leu Met Leu Pro Gly Asp Leu Val Gly Leu Gln His Asp
705                 710                 715                 720 gct ggc cct ggc gcc ctc ctg cac tgc tcg ccg gct ccc ggc cac cct      2208
Ala Gly Pro Gly Ala Leu Leu His Cys Ser Pro Ala Pro Gly His Pro
            725                 730                 735 ggt ccc cgg gcc ccg tac ctc tcc gcc aac gcc tcg tca tgg ctg ccc      2256
Gly Pro Arg Ala Pro Tyr Leu Ser Ala Asn Ala Ser Ser Trp Leu Pro
        740                 745                 750 cac ttg cca gcc cag ctg gag ggc act tgg ggc tgc cct gcc tgt gcc      2304
His Leu Pro Ala Gln Leu Glu Gly Thr Trp Gly Cys Pro Ala Cys Ala
    755                 760                 765 ctg cgg ctg ctt gca caa cgg gaa cag ctc acc gtg ctg ctg ggc ttg      2352
Leu Arg Leu Leu Ala Gln Arg Glu Gln Leu Thr Val Leu Leu Gly Leu
770                 775                 780 agg ccc aac cct gga ctg cgg ctg cct ggg cgc tat gag gtc cgg gca      2400
Arg Pro Asn Pro Gly Leu Arg Leu Pro Gly Arg Tyr Glu Val Arg Ala
785                 790                 795                 800 gag gtg ggc aat ggc gtg tcc agg cac aac ctc tcc tgc agc ttt gac      2448
Glu Val Gly Asn Gly Val Ser Arg His Asn Leu Ser Cys Ser Phe Asp
            805                 810                 815 gtg gtc tcc cca gtg gct ggg ctg cgg gtc atc tac cct gcc ccc cgc      2496
Val Val Ser Pro Val Ala Gly Leu Arg Val Ile Tyr Pro Ala Pro Arg
        820                 825                 830 gac ggc cgc ctc tac gtg ccc acc aac ggc tca gcc ttg gtg ctc cag      2544
Asp Gly Arg Leu Tyr Val Pro Thr Asn Gly Ser Ala Leu Val Leu Gln
    835                 840                 845 gtg gac tct ggt gcc aac gcc acg gcc acg gct cgc tgg cct ggg ggc      2592
Val Asp Ser Gly Ala Asn Ala Thr Ala Thr Ala Arg Trp Pro Gly Gly
850                 855                 860 agt ctc agc gcc cgc ttt gag aat gtc tgc cct gcc ctg gtg gcc acc      2640
Ser Leu Ser Ala Arg Phe Glu Asn Val Cys Pro Ala Leu Val Ala Thr
865                 870                 875                 880 ttc gtg ccc gcc tgc ccc tgg gag acc aac gat acc ctg ttc tca gtg      2688
Phe Val Pro Ala Cys Pro Trp Glu Thr Asn Asp Thr Leu Phe Ser Val
            885                 890                 895 gta gca ctg ccg tgg ctc agt gag ggg gag cac gtg gtg gac gtg gtg      2736
Val Ala Leu Pro Trp Leu Ser Glu Gly Glu His Val Val Asp Val Val
        900                 905                 910 gtg gaa aac agc gcc agc cgg gcc aac ctc agc ctg cgg gtg acg gcg      2784
Val Glu Asn Ser Ala Ser Arg Ala Asn Leu Ser Leu Arg Val Thr Ala
    915                 920                 925 gag gag ccc atc tgt ggc ctc cgc gcc acg ccc agc ccc gag gcc cgt      2832
Glu Glu Pro Ile Cys Gly Leu Arg Ala Thr Pro Ser Pro Glu Ala Arg
930                 935                 940 gta ctg cag gga gtc cta gtg agg tac agc ccc gtg gtg gag gcc ggc      2880
Val Leu Gln Gly Val Leu Val Arg Tyr Ser Pro Val Val Glu Ala Gly
945                 950                 955                 960 tcg gac atg gtc ttc cgg tgg acc atc aac gac aag cag tcc ctg acc      2928
```

-continued

```
Ser Asp Met Val Phe Arg Trp Thr Ile Asn Asp Lys Gln Ser Leu Thr
                965                 970                 975 ttc cag aac gtg gtc ttc aat gtc att tat cag agc gcg gcg gtc ttc      2976
Phe Gln Asn Val Val Phe Asn Val Ile Tyr Gln Ser Ala Ala Val Phe
                980                 985                 990 aag ctc tca ctg acg gcc tcc aac cac gtg agc aac gtc acc gtg aac      3024
Lys Leu Ser Leu Thr Ala Ser Asn His Val Ser Asn Val Thr Val Asn
                995                 1000                1005 tac aac gta acc gtg gag cgg atg aac agg atg cag ggt ctg cag gtc      3072
Tyr Asn Val Thr Val Glu Arg Met Asn Arg Met Gln Gly Leu Gln Val
    1010                1015                1020 tcc aca gtg ccg gcc gtg ctg tcc ccc aat gcc acg cta gca ctg acg      3120
Ser Thr Val Pro Ala Val Leu Ser Pro Asn Ala Thr Leu Ala Leu Thr
1025                1030                1035                1040 gcg ggc gtg ctg gtg gac tcg gcc gtg gag gtg gcc ttc ctg tgg acc      3168
Ala Gly Val Leu Val Asp Ser Ala Val Glu Val Ala Phe Leu Trp Thr
                1045                1050                1055 ttt ggg gat ggg gag cag gcc ctc cac cag ttc cag cct ccg tac aac      3216
Phe Gly Asp Gly Glu Gln Ala Leu His Gln Phe Gln Pro Pro Tyr Asn
                1060                1065                1070 gag tcc ttc cca gtt cca gac ccc tcg gtg gcc cag gtg ctg gtg gag      3264
Glu Ser Phe Pro Val Pro Asp Pro Ser Val Ala Gln Val Leu Val Glu
                1075                1080                1085 cac aat gtc acg cac acc tac gct gcc cca ggt gag tac ctc ctg acc      3312
His Asn Val Thr His Thr Tyr Ala Ala Pro Gly Glu Tyr Leu Leu Thr
                1090                1095                1100 gtg ctg gca tct aat gcc ttc gag aac ctg acg cag cag gtg cct gtg      3360
Val Leu Ala Ser Asn Ala Phe Glu Asn Leu Thr Gln Gln Val Pro Val
1105                1110                1115                1120 agc gtg cgc gcc tcc ctg ccc tcc gtg gct gtg ggt gtg agt gac ggc      3408
Ser Val Arg Ala Ser Leu Pro Ser Val Ala Val Gly Val Ser Asp Gly
                1125                1130                1135 gtc ctg gtg gcc ggc cgg ccc gtc acc ttc tac ccg cac ccg ctg ccc      3456
Val Leu Val Ala Gly Arg Pro Val Thr Phe Tyr Pro His Pro Leu Pro
                1140                1145                1150 tcg cct ggg ggt gtt ctt tac acg tgg gac ttc ggg gac ggc tcc cct      3504
Ser Pro Gly Gly Val Leu Tyr Thr Trp Asp Phe Gly Asp Gly Ser Pro
                1155                1160                1165 gtc ctg acc cag agc cag ccg gct gcc aac cac acc tat gcc tcg agg      3552
Val Leu Thr Gln Ser Gln Pro Ala Ala Asn His Thr Tyr Ala Ser Arg
    1170                1175                1180 ggc acc tac cac gtg cgc ctg gag gtc aac aac acg gtg agc ggt gcg      3600
Gly Thr Tyr His Val Arg Leu Glu Val Asn Asn Thr Val Ser Gly Ala
1185                1190                1195                1200 gcg gcc cag gcg gat gtg cgc gtc ttt gag gag ctc cgc gga ctc agc      3648
Ala Ala Gln Ala Asp Val Arg Val Phe Glu Glu Leu Arg Gly Leu Ser
                1205                1210                1215 gtg gac atg agc ctg gcc gtg gag cag ggc gcc ccc gtg gtg gtc agc      3696
Val Asp Met Ser Leu Ala Val Glu Gln Gly Ala Pro Val Val Val Ser
                1220                1225                1230 gcc gcg gtg cag acg ggc gac aac atc acg tgg acc ttc gac atg ggg      3744
Ala Ala Val Gln Thr Gly Asp Asn Ile Thr Trp Thr Phe Asp Met Gly
1235                1240                1245 gac ggc acc gtg ctg tcg ggc ccg gag gca aca gtg gag cat gtg tac      3792
Asp Gly Thr Val Leu Ser Gly Pro Glu Ala Thr Val Glu His Val Tyr
                1250                1255                1260 ctg cgg gca cag aac tgc aca gtg acc gtg ggt gcg ggc agc ccc gcc      3840
Leu Arg Ala Gln Asn Cys Thr Val Thr Val Gly Ala Gly Ser Pro Ala
1265                1270                1275                1280
```

```
ggc cac ctg gcc cgg agc ctg cac gtg ctg gtc ttc gtc ctg gag gtg       3888
Gly His Leu Ala Arg Ser Leu His Val Leu Val Phe Val Leu Glu Val
            1285                1290                1295 ctg cgt gtt gaa ccc gcc gcc tgc atc ccc acg cag cct gac gcg cgg       3936
Leu Arg Val Glu Pro Ala Ala Cys Ile Pro Thr Gln Pro Asp Ala Arg
        1300                1305                1310 ctc acg gcc tac gtc acc ggg aac ccg gcc cac tac ctc ttc gac tgg       3984
Leu Thr Ala Tyr Val Thr Gly Asn Pro Ala His Tyr Leu Phe Asp Trp
    1315                1320                1325 acc ttc ggg gat ggc tcc tcc aac acg acc gtg cgg ggg tgc ccg acg       4032
Thr Phe Gly Asp Gly Ser Ser Asn Thr Thr Val Arg Gly Cys Pro Thr
1330                1335                1340 gtg aca cac aac ttc acg cgg agc ggc acg ttc ccc ctg gcg ctg gtg       4080
Val Thr His Asn Phe Thr Arg Ser Gly Thr Phe Pro Leu Ala Leu Val
1345                1350                1355                1360 ctg tcc agc cgc gtg aac agg gcg cat tac ttc acc agc atc tgc gtg       4128
Leu Ser Ser Arg Val Asn Arg Ala His Tyr Phe Thr Ser Ile Cys Val
            1365                1370                1375 gag cca gag gtg ggc aac gtc acc ctg cag cca gag agg cag ttt gtg       4176
Glu Pro Glu Val Gly Asn Val Thr Leu Gln Pro Glu Arg Gln Phe Val
        1380                1385                1390 cag ctc ggg gac gag gcc tgg ctg gtg gca tgt gcc tgg ccc ccg ttc       4224
Gln Leu Gly Asp Glu Ala Trp Leu Val Ala Cys Ala Trp Pro Pro Phe
    1395                1400                1405 ccc tac cgc tac acc tgg gac ttt ggc acc gag gaa gcc gcc ccc acc       4272
Pro Tyr Arg Tyr Thr Trp Asp Phe Gly Thr Glu Glu Ala Ala Pro Thr
1410                1415                1420 cgt gcc agg ggc cct gag gtg acg ttc atc tac cga gac cca ggc tcc       4320
Arg Ala Arg Gly Pro Glu Val Thr Phe Ile Tyr Arg Asp Pro Gly Ser
1425                1430                1435                1440 tat ctt gtg aca gtc acc gcg tcc aac aac atc tct gct gcc aat gac       4368
Tyr Leu Val Thr Val Thr Ala Ser Asn Asn Ile Ser Ala Ala Asn Asp
            1445                1450                1455 tca gcc ctg gtg gag gtg cag gag ccc gtg ctg gtc acc agc atc aag       4416
Ser Ala Leu Val Glu Val Gln Glu Pro Val Leu Val Thr Ser Ile Lys
        1460                1465                1470 gtc aat ggc tcc ctt ggg ctg gag ctg cag cag ccg tac ctg ttc tct       4464
Val Asn Gly Ser Leu Gly Leu Glu Leu Gln Gln Pro Tyr Leu Phe Ser
    1475                1480                1485 gct gtg ggc cgt ggg cgc ccc gcc agc tac ctg tgg gat ctg ggg gac       4512
Ala Val Gly Arg Gly Arg Pro Ala Ser Tyr Leu Trp Asp Leu Gly Asp
1490                1495                1500 ggt ggg tgg ctc gag ggt ccg gag gtc acc cac gct tac aac agc aca       4560
Gly Gly Trp Leu Glu Gly Pro Glu Val Thr His Ala Tyr Asn Ser Thr
1505                1510                1515                1520 ggt gac ttc acc gtt agg gtg gcc ggc tgg aat gag gtg agc cgc agc       4608
Gly Asp Phe Thr Val Arg Val Ala Gly Trp Asn Glu Val Ser Arg Ser
            1525                1530                1535 gag gcc tgg ctc aat gtg acg gtg aag cgg cgc gtg cgg ggg ctc gtc       4656
Glu Ala Trp Leu Asn Val Thr Val Lys Arg Arg Val Arg Gly Leu Val
        1540                1545                1550 gtc aat gca agc cgc acg gtg gtg ccc ctg aat ggg agc gtg agc ttc       4704
Val Asn Ala Ser Arg Thr Val Val Pro Leu Asn Gly Ser Val Ser Phe
    1555                1560                1565 agc acg tcg ctg gag gcc ggc agt gat gtg cgc tat ccc tgg gtg ctc       4752
Ser Thr Ser Leu Glu Ala Gly Ser Asp Val Arg Tyr Ser Trp Val Leu
1570                1575                1580 tgt gac cgc tgc acg ccc atc cct ggg ggt cct acc atc tct tac acc       4800
Cys Asp Arg Cys Thr Pro Ile Pro Gly Gly Pro Thr Ile Ser Tyr Thr
1585                1590                1595                1600
```

```
ttc cgc tcc gtg ggc acc ttc aat atc atc gtc acg gct gag aac gag      4848
Phe Arg Ser Val Gly Thr Phe Asn Ile Ile Val Thr Ala Glu Asn Glu
             1605                1610                1615 gtg ggc tcc gcc cag gac agc atc ttc gtc tat gtc ctg cag ctc ata      4896
Val Gly Ser Ala Gln Asp Ser Ile Phe Val Tyr Val Leu Gln Leu Ile
         1620                1625                1630 gag ggg ctg cag gtg gtg ggc ggt ggc cgc tac ttc ccc acc aac cac      4944
Glu Gly Leu Gln Val Val Gly Gly Gly Arg Tyr Phe Pro Thr Asn His
     1635                1640                1645 acg gta cag ctg cag gcc gtg gtt agg gat ggc acc aac gtc tcc tac      4992
Thr Val Gln Leu Gln Ala Val Val Arg Asp Gly Thr Asn Val Ser Tyr
 1650                1655                1660 agc tgg act gcc tgg agg gac agg ggc ccg gcc ctg gcc ggc agc ggc      5040
Ser Trp Thr Ala Trp Arg Asp Arg Gly Pro Ala Leu Ala Gly Ser Gly
1665                1670                1675                1680 aaa ggc ttc tcg ctc acc gtg ctc gag gcc ggc acc tac cat gtg cag      5088
Lys Gly Phe Ser Leu Thr Val Leu Glu Ala Gly Thr Tyr His Val Gln
             1685                1690                1695 ctg cgg gcc acc aac atg ctg ggc agc gcc tgg gcc gac tgc acc atg      5136
Leu Arg Ala Thr Asn Met Leu Gly Ser Ala Trp Ala Asp Cys Thr Met
         1700                1705                1710 gac ttc gtg gag cct gtg ggg tgg ctg atg gtg gcc gcc tcc ccg aac      5184
Asp Phe Val Glu Pro Val Gly Trp Leu Met Val Ala Ala Ser Pro Asn
     1715                1720                1725 cca gct gcc gtc aac aca agc gtc acc ctc agt gcc gag ctg gct ggt      5232
Pro Ala Ala Val Asn Thr Ser Val Thr Leu Ser Ala Glu Leu Ala Gly
 1730                1735                1740 ggc agt ggt gtc gta tac act tgg tcc ttg gag gag ggg ctg agc tgg      5280
Gly Ser Gly Val Val Tyr Thr Trp Ser Leu Glu Glu Gly Leu Ser Trp
1745                1750                1755                1760 gag acc tcc gag cca ttt acc acc cat agc ttc ccc aca ccc ggc ctg      5328
Glu Thr Ser Glu Pro Phe Thr Thr His Ser Phe Pro Thr Pro Gly Leu
             1765                1770                1775 cac ttg gtc acc atg acg gca ggg aac ccg ctg ggc tca gcc aac gcc      5376
His Leu Val Thr Met Thr Ala Gly Asn Pro Leu Gly Ser Ala Asn Ala
         1780                1785                1790 acc gtg gaa gtg gat gtg cag gtg cct gtg agt ggc ctc agc atc agg      5424
Thr Val Glu Val Asp Val Gln Val Pro Val Ser Gly Leu Ser Ile Arg
     1795                1800                1805 gcc agc gag ccc gga ggc agc ttc gtg gcg gcc ggg tcc tct gtg ccc      5472
Ala Ser Glu Pro Gly Gly Ser Phe Val Ala Ala Gly Ser Ser Val Pro
 1810                1815                1820 ttt tgg ggg cag ctg gcc acg ggc acc aat gtg agc tgg tgc tgg gct      5520
Phe Trp Gly Gln Leu Ala Thr Gly Thr Asn Val Ser Trp Cys Trp Ala
1825                1830                1835                1840 gtg ccc ggc ggc agc agc aag cgt ggc cct cat gtc acc atg gtc ttc      5568
Val Pro Gly Gly Ser Ser Lys Arg Gly Pro His Val Thr Met Val Phe
             1845                1850                1855 ccg gat gct ggc acc ttc tcc atc cgg ctc aat gcc tcc aac gca gtc      5616
Pro Asp Ala Gly Thr Phe Ser Ile Arg Leu Asn Ala Ser Asn Ala Val
         1860                1865                1870 agc tgg gtc tca gcc acg tac aac ctc acg gcg gag gag ccc atc gtg      5664
Ser Trp Val Ser Ala Thr Tyr Asn Leu Thr Ala Glu Glu Pro Ile Val
     1875                1880                1885 ggc ctg gtg ctg tgg gcc agc agc aag gtg gtg gcg ccc ggg cag ctg      5712
Gly Leu Val Leu Trp Ala Ser Ser Lys Val Val Ala Pro Gly Gln Leu
 1890                1895                1900 gtc cat ttt cag atc ctg ctg gct gcc ggc tca gct gtc acc ttc cgc      5760
Val His Phe Gln Ile Leu Leu Ala Ala Gly Ser Ala Val Thr Phe Arg
```

-continued

| | | | | | | | | | | | | | | |
|---|---|---|---|---|---|---|---|---|---|---|---|---|---|---|
| 1905 | | | | 1910 | | | | 1915 | | | | 1920 | | |

```
cta cag gtc ggc ggg gcc aac ccc gag gtg ctc ccc ggg ccc cgt ttc    5808
Leu Gln Val Gly Gly Ala Asn Pro Glu Val Leu Pro Gly Pro Arg Phe
            1925                1930                1935 tcc cac agc ttc ccc cgc gtc gga gac cac gtg gtg agc gtg cgg ggc    5856
Ser His Ser Phe Pro Arg Val Gly Asp His Val Val Ser Val Arg Gly
        1940                1945                1950 aaa aac cac gtg agc tgg gcc cag gcg cag gtg cgc atc gtg gtg ctg    5904
Lys Asn His Val Ser Trp Ala Gln Ala Gln Val Arg Ile Val Val Leu
    1955                1960                1965 gag gcc gtg agt ggg ctg cag gtg ccc aac tgc tgc gag cct ggc atc    5952
Glu Ala Val Ser Gly Leu Gln Val Pro Asn Cys Cys Glu Pro Gly Ile
1970                1975                1980 gcc acg ggc act gag agg aac ttc aca gcc cgc gtg cag cgc ggc tct    6000
Ala Thr Gly Thr Glu Arg Asn Phe Thr Ala Arg Val Gln Arg Gly Ser
1985                1990                1995                2000 cgg gtc gcc tac gcc tgg tac ttc tcg ctg cag aag gtc cag ggc gac    6048
Arg Val Ala Tyr Ala Trp Tyr Phe Ser Leu Gln Lys Val Gln Gly Asp
                2005                2010                2015 tcg ctg gtc atc ctg tcg ggc cgc gac gtc acc tac acg ccc gtg gcc    6096
Ser Leu Val Ile Leu Ser Gly Arg Asp Val Thr Tyr Thr Pro Val Ala
            2020                2025                2030 gcg ggg ctg ttg gag atc cag gtg cgc gcc ttc aac gcc ctg ggc agt    6144
Ala Gly Leu Leu Glu Ile Gln Val Arg Ala Phe Asn Ala Leu Gly Ser
        2035                2040                2045 gag aac cgc acg ctg gtg ctg gag gtt cag gac gcc gtc cag tat gtg    6192
Glu Asn Arg Thr Leu Val Leu Glu Val Gln Asp Ala Val Gln Tyr Val
    2050                2055                2060 gcc ctg cag agc ggc ccc tgc ttc acc aac cgc tcg gcg cag ttt gag    6240
Ala Leu Gln Ser Gly Pro Cys Phe Thr Asn Arg Ser Ala Gln Phe Glu
2065                2070                2075                2080 gcc gcc acc agc ccc agc ccc cgg cgt gtg gcc tac cac tgg gac ttt    6288
Ala Ala Thr Ser Pro Ser Pro Arg Arg Val Ala Tyr His Trp Asp Phe
                2085                2090                2095 ggg gat ggg tcg cca ggg cag gac aca gat gag ccc agg gcc gag cac    6336
Gly Asp Gly Ser Pro Gly Gln Asp Thr Asp Glu Pro Arg Ala Glu His
            2100                2105                2110 tcc tac ctg agg cct ggg gac tac cgc gtg cag gtg aac gcc tcc aac    6384
Ser Tyr Leu Arg Pro Gly Asp Tyr Arg Val Gln Val Asn Ala Ser Asn
        2115                2120                2125 ctg gtg agc ttc ttc gtg gcg cag gcc acg gtg acc gtc cag gtg ctg    6432
Leu Val Ser Phe Phe Val Ala Gln Ala Thr Val Thr Val Gln Val Leu
    2130                2135                2140 gcc tgc cgg gag ccg gag gtg gac gtg gtc ctg ccc ctg cag gtg ctg    6480
Ala Cys Arg Glu Pro Glu Val Asp Val Val Leu Pro Leu Gln Val Leu
2145                2150                2155                2160 atg cgg cga tca cag cgc aac tac ttg gag gcc cac gtt gac ctg cgc    6528
Met Arg Arg Ser Gln Arg Asn Tyr Leu Glu Ala His Val Asp Leu Arg
                2165                2170                2175 gac tgc gtc acc tac cag act gag tac cgc tgg gag gtg tat cgc acc    6576
Asp Cys Val Thr Tyr Gln Thr Glu Tyr Arg Trp Glu Val Tyr Arg Thr
            2180                2185                2190 gcc agc tgc cag cgg ccg ggg cgc cca gcg cgt gtg gcc ctg ccc ggc    6624
Ala Ser Cys Gln Arg Pro Gly Arg Pro Ala Arg Val Ala Leu Pro Gly
        2195                2200                2205 gtg gac gtg agc cgg cct cgg ctg gtg ctg ccg cgg ctg gcg ctg cct    6672
Val Asp Val Ser Arg Pro Arg Leu Val Leu Pro Arg Leu Ala Leu Pro
    2210                2215                2220 gtg ggg cac tac tgc ttt gtg ttt gtc gtg tca ttt ggg gac acg cca    6720
```

```
                                              -continued

Val Gly His Tyr Cys Phe Val Phe Val Val Ser Phe Gly Asp Thr Pro
2225                2230                2235                2240 ctg aca cag agc atc cag gcc aat gtg acg gtg gcc ccc gag cgc ctg         6768
Leu Thr Gln Ser Ile Gln Ala Asn Val Thr Val Ala Pro Glu Arg Leu
            2245                2250                2255 gtg ccc atc att gag ggt ggc tca tac cgc gtg tgg tca gac aca cgg         6816
Val Pro Ile Ile Glu Gly Gly Ser Tyr Arg Val Trp Ser Asp Thr Arg
2260                2265                2270 gac ctg gtg ctg gat ggg agc gag tcc tac gac ccc aac ctg gag gac         6864
Asp Leu Val Leu Asp Gly Ser Glu Ser Tyr Asp Pro Asn Leu Glu Asp
    2275                2280                2285 ggc gac cag acg ccg ctc agt ttc cac tgg gcc tgt gtg gct tcg aca         6912
Gly Asp Gln Thr Pro Leu Ser Phe His Trp Ala Cys Val Ala Ser Thr
        2290                2295                2300 cag agg gag gct ggc ggg tgt gcg ctg aac ttt ggg ccc cgc ggg agc         6960
Gln Arg Glu Ala Gly Gly Cys Ala Leu Asn Phe Gly Pro Arg Gly Ser
2305                2310                2315                2320 agc acg gtc acc att cca cgg gag cgg ctg gcg gct ggc gtg gag tac         7008
Ser Thr Val Thr Ile Pro Arg Glu Arg Leu Ala Ala Gly Val Glu Tyr
            2325                2330                2335 acc ttc agc ctg acc gtg tgg aag gcc ggc cgc aag gag gag gcc acc         7056
Thr Phe Ser Leu Thr Val Trp Lys Ala Gly Arg Lys Glu Glu Ala Thr
2340                2345                2350 aac cag acg gtg ctg atc cgg agt ggc cgg gtg ccc att gtg tcc ttg         7104
Asn Gln Thr Val Leu Ile Arg Ser Gly Arg Val Pro Ile Val Ser Leu
    2355                2360                2365 gag tgt gtg tcc tgc aag gca cag gcc gtg tac gaa gtg agc cgc agc         7152
Glu Cys Val Ser Cys Lys Ala Gln Ala Val Tyr Glu Val Ser Arg Ser
        2370                2375                2380 tcc tac gtg tac ttg gag ggc cgc tgc ctc aat tgc agc agc ggc tcc         7200
Ser Tyr Val Tyr Leu Glu Gly Arg Cys Leu Asn Cys Ser Ser Gly Ser
2385                2390                2395                2400 aag cga ggg cgg tgg gct gca cgt acg ttc agc aac aag acg ctg gtg         7248
Lys Arg Gly Arg Trp Ala Ala Arg Thr Phe Ser Asn Lys Thr Leu Val
            2405                2410                2415 ctg gat gag acc acc aca tcc acg ggc agt gca ggc atg cga ctg gtg         7296
Leu Asp Glu Thr Thr Thr Ser Thr Gly Ser Ala Gly Met Arg Leu Val
2420                2425                2430 ctg cgg cgg ggc gtg ctg cgg gac ggc gag gga tac acc ttc acg ctc         7344
Leu Arg Arg Gly Val Leu Arg Asp Gly Glu Gly Tyr Thr Phe Thr Leu
    2435                2440                2445 acg gtg ctg ggc cgc tct ggc gag gag gag ggc tgc gcc tcc atc cgc         7392
Thr Val Leu Gly Arg Ser Gly Glu Glu Glu Gly Cys Ala Ser Ile Arg
        2450                2455                2460 ctg tcc ccc aac cgc ccg ccg ctg ggg ggc tct tgc cgc ctc ttc cca         7440
Leu Ser Pro Asn Arg Pro Pro Leu Gly Gly Ser Cys Arg Leu Phe Pro
2465                2470                2475                2480 ctg ggc gct gtg cac gcc ctc acc acc aag gtg cac ttc gaa tgc acg         7488
Leu Gly Ala Val His Ala Leu Thr Thr Lys Val His Phe Glu Cys Thr
            2485                2490                2495 ggc tgg cat gac gcg gag gat gct ggc gcc ccg ctg gtg tac gcc ctg         7536
Gly Trp His Asp Ala Glu Asp Ala Gly Ala Pro Leu Val Tyr Ala Leu
2500                2505                2510 ctg ctg cgg cgc tgt cgc cag ggc cac tgc gag gag ttc tgt gtc tac         7584
Leu Leu Arg Arg Cys Arg Gln Gly His Cys Glu Glu Phe Cys Val Tyr
    2515                2520                2525 aag ggc agc ctc tcc agc tac gga gcc gtg ctg ccc ccg ggt ttc agg         7632
Lys Gly Ser Leu Ser Ser Tyr Gly Ala Val Leu Pro Pro Gly Phe Arg
        2530                2535                2540
```

```
cca cac ttc gag gtg ggc ctg gcc gtg gtg gtg cag gac cag ctg gga      7680
Pro His Phe Glu Val Gly Leu Ala Val Val Val Gln Asp Gln Leu Gly
2545                2550                2555                2560 gcc gct gtg gtc gcc ctc aac agg tct ttg gcc atc acc ctc cca gag      7728
Ala Ala Val Val Ala Leu Asn Arg Ser Leu Ala Ile Thr Leu Pro Glu
            2565                2570                2575 ccc aac ggc agc gca acg ggg ctc aca gtc tgg ctg cac ggg ctc acc      7776
Pro Asn Gly Ser Ala Thr Gly Leu Thr Val Trp Leu His Gly Leu Thr
        2580                2585                2590 gct agt gtg ctc cca ggg ctg ctg cgg cag gcc gat ccc cag cac gtc      7824
Ala Ser Val Leu Pro Gly Leu Leu Arg Gln Ala Asp Pro Gln His Val
    2595                2600                2605 atc gag tac tcg ttg gcc ctg gtc acc gtg ctg aac gag tac gag cgg      7872
Ile Glu Tyr Ser Leu Ala Leu Val Thr Val Leu Asn Glu Tyr Glu Arg
2610                2615                2620 gcc ctg gac gtg gcg gca gag ccc aag cac gag cgg cag cac cga gcc      7920
Ala Leu Asp Val Ala Ala Glu Pro Lys His Glu Arg Gln His Arg Ala
2625                2630                2635                2640 cag ata cgc aag aac atc acg gag act ctg gtg tcc ctg agg gtc cac      7968
Gln Ile Arg Lys Asn Ile Thr Glu Thr Leu Val Ser Leu Arg Val His
            2645                2650                2655 act gtg gat gac atc cag cag atc gct gct gcg ctg gcc cag tgc atg      8016
Thr Val Asp Asp Ile Gln Gln Ile Ala Ala Ala Leu Ala Gln Cys Met
        2660                2665                2670 ggg ccc agc agg gag ctc gta tgc cgc tcg tgc ctg aag cag acg ctg      8064
Gly Pro Ser Arg Glu Leu Val Cys Arg Ser Cys Leu Lys Gln Thr Leu
    2675                2680                2685 cac aag ctg gag gcc atg atg ctc atc ctg cag gca gag acc acc gcg      8112
His Lys Leu Glu Ala Met Met Leu Ile Leu Gln Ala Glu Thr Thr Ala
2690                2695                2700 ggc acc gtg acg ccc acc gcc atc gga gac agc atc ctc aac atc aca      8160
Gly Thr Val Thr Pro Thr Ala Ile Gly Asp Ser Ile Leu Asn Ile Thr
2705                2710                2715                2720 gga gac ctc atc cac ctg gcc agc tcg gac gtg cgg gca cca cag ccc      8208
Gly Asp Leu Ile His Leu Ala Ser Ser Asp Val Arg Ala Pro Gln Pro
            2725                2730                2735 tca gag ctg gga gcc gag tca cca tct cgg atg gtg gcg tcc cag gcc      8256
Ser Glu Leu Gly Ala Glu Ser Pro Ser Arg Met Val Ala Ser Gln Ala
        2740                2745                2750 tac aac ctg acc tct gcc ctc atg cgc atc ctc atg cgc tcc cgc gtg      8304
Tyr Asn Leu Thr Ser Ala Leu Met Arg Ile Leu Met Arg Ser Arg Val
    2755                2760                2765 ctc aac gag gag ccc ctg acg ctg gcg ggc gag gag atc gtg gcc cag      8352
Leu Asn Glu Glu Pro Leu Thr Leu Ala Gly Glu Glu Ile Val Ala Gln
2770                2775                2780 ggc aag cgc tcg gac ccg cgg agc ctg ctg tgc tat ggc ggc gcc cca      8400
Gly Lys Arg Ser Asp Pro Arg Ser Leu Leu Cys Tyr Gly Gly Ala Pro
2785                2790                2795                2800 ggg cct ggc tgc cac ttc tcc atc ccc gag gct ttc agc ggg gcc ctg      8448
Gly Pro Gly Cys His Phe Ser Ile Pro Glu Ala Phe Ser Gly Ala Leu
            2805                2810                2815 gcc aac ctc agt gac gtg gtg cag ctc atc ttt ctg gtg gac tcc aat      8496
Ala Asn Leu Ser Asp Val Val Gln Leu Ile Phe Leu Val Asp Ser Asn
        2820                2825                2830 ccc ttt ccc ttt ggc tat atc agc aac tac acc gtc tcc acc aag gtg      8544
Pro Phe Pro Phe Gly Tyr Ile Ser Asn Tyr Thr Val Ser Thr Lys Val
    2835                2840                2845 gcc tcg atg gca ttc cag aca cag gcc ggc gcc cag atc ccc atc gag      8592
Ala Ser Met Ala Phe Gln Thr Gln Ala Gly Ala Gln Ile Pro Ile Glu
2850                2855                2860
```

```
                                                                        -continued cgg ctg gcc tca gag cgc gcc atc acc gtg aag gtg ccc aac aac tcg         8640
Arg Leu Ala Ser Glu Arg Ala Ile Thr Val Lys Val Pro Asn Asn Ser
2865                2870                2875                2880 gac tgg gct gcc cgg ggc cac cgc agc tcc gcc aac tcc gcc aac tcc         8688
Asp Trp Ala Ala Arg Gly His Arg Ser Ser Ala Asn Ser Ala Asn Ser
            2885                2890                2895 gtt gtg gtc cag ccc cag gcc tcc gtc ggt gct gtg gtc acc ctg gac         8736
Val Val Val Gln Pro Gln Ala Ser Val Gly Ala Val Val Thr Leu Asp
    2900                2905                2910 agc agc aac cct gcg gcc ggg ctg cat ctg cag ctc aac tat acg ctg         8784
Ser Ser Asn Pro Ala Ala Gly Leu His Leu Gln Leu Asn Tyr Thr Leu
2915                2920                2925 ctg gac ggc cac tac ctg tct gag gaa cct gag ccc tac ctg gca gtc         8832
Leu Asp Gly His Tyr Leu Ser Glu Glu Pro Glu Pro Tyr Leu Ala Val
            2930                2935                2940 tac cta cac tcg gag ccc cgg ccc aat gag cac aac tgc tcg gct agc         8880
Tyr Leu His Ser Glu Pro Arg Pro Asn Glu His Asn Cys Ser Ala Ser
2945                2950                2955                2960 agg agg atc cgc cca gag tca ctc cag ggt gct gac cac cgg ccc tac         8928
Arg Arg Ile Arg Pro Glu Ser Leu Gln Gly Ala Asp His Arg Pro Tyr
            2965                2970                2975 acc ttc ttc att tcc ccg ggg agc aga gac cca gcg ggg agt tac cat         8976
Thr Phe Phe Ile Ser Pro Gly Ser Arg Asp Pro Ala Gly Ser Tyr His
    2980                2985                2990 ctg aac ctc tcc agc cac ttc cgc tgg tcg gcg ctg cag gtg tcc gtg         9024
Leu Asn Leu Ser Ser His Phe Arg Trp Ser Ala Leu Gln Val Ser Val
2995                3000                3005 ggc ctg tac acg tcc ctg tgc cag tac ttc agc gag gag gac atg gtg         9072
Gly Leu Tyr Thr Ser Leu Cys Gln Tyr Phe Ser Glu Glu Asp Met Val
    3010                3015                3020 tgg cgg aca gag ggg ctg ctg ccc ctg gag gag acc tcg ccc cgc cag         9120
Trp Arg Thr Glu Gly Leu Leu Pro Leu Glu Glu Thr Ser Pro Arg Gln
3025                3030                3035                3040 gcc gtc tgc ctc acc cgc cac ctc acc gcc ttc ggc gcc agc ctc ttc         9168
Ala Val Cys Leu Thr Arg His Leu Thr Ala Phe Gly Ala Ser Leu Phe
            3045                3050                3055 gtg ccc cca agc cat gtc cgc ttt gtg ttt cct gag ccg aca gcg gat         9216
Val Pro Pro Ser His Val Arg Phe Val Phe Pro Glu Pro Thr Ala Asp
    3060                3065                3070 gta aac tac atc gtc atg ctg aca tgt gct gtg tgc ctg gtg acc tac         9264
Val Asn Tyr Ile Val Met Leu Thr Cys Ala Val Cys Leu Val Thr Tyr
3075                3080                3085 atg gtc atg gcc gcc atc ctg cac aag ctg gac cag ttg gat gcc agc         9312
Met Val Met Ala Ala Ile Leu His Lys Leu Asp Gln Leu Asp Ala Ser
    3090                3095                3100 cgg ggc cgc gcc atc cct ttc tgt ggg cag cgg ggc cgc ttc aag tac         9360
Arg Gly Arg Ala Ile Pro Phe Cys Gly Gln Arg Gly Arg Phe Lys Tyr
3105                3110                3115                3120 gag atc ctc gtc aag aca ggc tgg ggc cgg ggc tca ggt acc acg gcc         9408
Glu Ile Leu Val Lys Thr Gly Trp Gly Arg Gly Ser Gly Thr Thr Ala
            3125                3130                3135 cac gtg ggc atc atg ctg tat ggg gtg gac agc cgg agc ggc cac cgg         9456
His Val Gly Ile Met Leu Tyr Gly Val Asp Ser Arg Ser Gly His Arg
    3140                3145                3150 cac ctg gac ggc gac aga gcc ttc cac cgc aac agc ctg gac atc ttc         9504
His Leu Asp Gly Asp Arg Ala Phe His Arg Asn Ser Leu Asp Ile Phe
3155                3160                3165 cgg atc gcc acc ccg cac agc ctg ggt agc gtg tgg aag atc cga gtg         9552
Arg Ile Ala Thr Pro His Ser Leu Gly Ser Val Trp Lys Ile Arg Val
```

```
      3170                3175                3180
tgg cac gac aac aaa ggg ctc agc cct gcc tgg ttc ctg cag cac gtc    9600
Trp His Asp Asn Lys Gly Leu Ser Pro Ala Trp Phe Leu Gln His Val
3185                3190                3195                3200 atc gtc agg gac ctg cag acg gca cgc agc gcc ttc ttc ctg gtc aat    9648
Ile Val Arg Asp Leu Gln Thr Ala Arg Ser Ala Phe Phe Leu Val Asn
            3205                3210                3215 gac tgg ctt tcg gtg gag acg gag gcc aac ggg ggc ctg gtg gag aag    9696
Asp Trp Leu Ser Val Glu Thr Glu Ala Asn Gly Gly Leu Val Glu Lys
        3220                3225                3230 gag gtg ctg gcc gcg agc gac gca gcc ctt ttg cgc ttc cgg cgc ctg    9744
Glu Val Leu Ala Ala Ser Asp Ala Ala Leu Leu Arg Phe Arg Arg Leu
    3235                3240                3245 ctg gtg gct gag ctg cag cgt ggc ttc ttt gac aag cac atc tgg ctc    9792
Leu Val Ala Glu Leu Gln Arg Gly Phe Phe Asp Lys His Ile Trp Leu
  3250                3255                3260 tcc ata tgg gac cgg ccg cct cgt agc cgt ttc act cgc atc cag agg    9840
Ser Ile Trp Asp Arg Pro Pro Arg Ser Arg Phe Thr Arg Ile Gln Arg
3265                3270                3275                3280 gcc acc tgc tgc gtt ctc ctc atc tgc ctc ttc ctg ggc gcc aac gcc    9888
Ala Thr Cys Cys Val Leu Leu Ile Cys Leu Phe Leu Gly Ala Asn Ala
            3285                3290                3295 gtg tgg tac ggg gct gtt ggc gac tct gcc tac agc acg ggg cat gtg    9936
Val Trp Tyr Gly Ala Val Gly Asp Ser Ala Tyr Ser Thr Gly His Val
        3300                3305                3310 tcc agg ctg agc ccg ctg agc gtc gac aca gtc gct gtt ggc ctg gtg    9984
Ser Arg Leu Ser Pro Leu Ser Val Asp Thr Val Ala Val Gly Leu Val
    3315                3320                3325 tcc agc gtg gtt gtc tat ccc gtc tac ctg gcc atc ctt ttt ctc ttc   10032
Ser Ser Val Val Val Tyr Pro Val Tyr Leu Ala Ile Leu Phe Leu Phe
  3330                3335                3340 cgg atg tcc cgg agc aag gtg gct ggg agc ccg agc ccc aca cct gcc   10080
Arg Met Ser Arg Ser Lys Val Ala Gly Ser Pro Ser Pro Thr Pro Ala
3345                3350                3355                3360 ggg cag cag gtg ctg gac atc gac agc tgc ctg gac tcg tcc gtg ctg   10128
Gly Gln Gln Val Leu Asp Ile Asp Ser Cys Leu Asp Ser Ser Val Leu
            3365                3370                3375 gac agc tcc ttc ctc acg ttc tca ggc ctc cac gct gag cag gcc ttt   10176
Asp Ser Ser Phe Leu Thr Phe Ser Gly Leu His Ala Glu Gln Ala Phe
        3380                3385                3390 gtt gga cag atg aag agt gac ttg ttt ctg gat gat tct aag agt ctg   10224
Val Gly Gln Met Lys Ser Asp Leu Phe Leu Asp Asp Ser Lys Ser Leu
    3395                3400                3405 gtg tgc tgg ccc tcc ggc gag gga acg ctc agt tgg ccg gac ctg ctc   10272
Val Cys Trp Pro Ser Gly Glu Gly Thr Leu Ser Trp Pro Asp Leu Leu
  3410                3415                3420 agt gac ccg tcc att gtg ggt agc aat ctg cgg cag ctg gca cgg ggc   10320
Ser Asp Pro Ser Ile Val Gly Ser Asn Leu Arg Gln Leu Ala Arg Gly
3425                3430                3435                3440 cag gcg ggc cat ggg ctg ggc cca gag gag gac ggc ttc tcc ctg gcc   10368
Gln Ala Gly His Gly Leu Gly Pro Glu Glu Asp Gly Phe Ser Leu Ala
            3445                3450                3455 agc ccc tac tcg cct gcc aaa tcc ttc tca gca tca gat gaa gac ctg   10416
Ser Pro Tyr Ser Pro Ala Lys Ser Phe Ser Ala Ser Asp Glu Asp Leu
        3460                3465                3470 atc cag cag gtc ctt gcc gag ggg gtc agc agc cca gcc cct acc caa   10464
Ile Gln Gln Val Leu Ala Glu Gly Val Ser Ser Pro Ala Pro Thr Gln
    3475                3480                3485 gac acc cac atg gaa acg gac ctg ctc agc agc ctg tcc agc act cct   10512
```

```
                                                          -continued

Asp Thr His Met Glu Thr Asp Leu Leu Ser Ser Leu Ser Ser Thr Pro
    3490                3495                3500 ggg gag aag aca gag acg ctg gcg ctg cag agg ctg ggg gag ctg ggg          10560
Gly Glu Lys Thr Glu Thr Leu Ala Leu Gln Arg Leu Gly Glu Leu Gly
3505                3510                3515                3520 cca ccc agc cca ggc ctg aac tgg gaa cag ccc cag gca gcg agg ctg          10608
Pro Pro Ser Pro Gly Leu Asn Trp Glu Gln Pro Gln Ala Ala Arg Leu
                3525                3530                3535 tcc agg aca gga ctg gtg gag ggt ctg cgg aag cgc ctg ctg ccg gcc          10656
Ser Arg Thr Gly Leu Val Glu Gly Leu Arg Lys Arg Leu Leu Pro Ala
        3540                3545                3550 tgg tgt gcc tcc ctg gcc cac ggg ctc agc ctg ctc ctg gtg gct gtg          10704
Trp Cys Ala Ser Leu Ala His Gly Leu Ser Leu Leu Leu Val Ala Val
            3555                3560                3565 gct gtg gct gtc tca ggg tgg gtg ggt gcg agc ttc ccc ccg ggc gtg          10752
Ala Val Ala Val Ser Gly Trp Val Gly Ala Ser Phe Pro Pro Gly Val
    3570                3575                3580 agt gtt gcg tgg ctc ctg tcc agc agc gcc agc ttc ctg gcc tca ttc          10800
Ser Val Ala Trp Leu Leu Ser Ser Ser Ala Ser Phe Leu Ala Ser Phe
3585                3590                3595                3600 ctc ggc tgg gag cca ctg aag gtc ttg ctg gaa gcc ctg tac ttc tca          10848
Leu Gly Trp Glu Pro Leu Lys Val Leu Leu Glu Ala Leu Tyr Phe Ser
                3605                3610                3615 ctg gtg gcc aag cgg ctg cac ccg gat gaa gat gac acc ctg gta gag          10896
Leu Val Ala Lys Arg Leu His Pro Asp Glu Asp Asp Thr Leu Val Glu
        3620                3625                3630 agc ccg gct gtg acg cct gtg agc gca cgt gtg ccc cgc gta cgg cca          10944
Ser Pro Ala Val Thr Pro Val Ser Ala Arg Val Pro Arg Val Arg Pro
            3635                3640                3645 ccc cac ggc ttt gca ctc ttc ctg gcc aag gaa gaa gcc cgc aag gtc          10992
Pro His Gly Phe Ala Leu Phe Leu Ala Lys Glu Glu Ala Arg Lys Val
    3650                3655                3660 aag agg cta cat ggc atg ctg cgg agc ctc ctg gtg tac atg ctt ttt          11040
Lys Arg Leu His Gly Met Leu Arg Ser Leu Leu Val Tyr Met Leu Phe
3665                3670                3675                3680 ctg ctg gtg acc ctg ctg gcc agc tat ggg gat gcc tca tgc cat ggg          11088
Leu Leu Val Thr Leu Leu Ala Ser Tyr Gly Asp Ala Ser Cys His Gly
                3685                3690                3695 cac gcc tac cgt ctg caa agc gcc atc aag cag gag ctg cac agc cgg          11136
His Ala Tyr Arg Leu Gln Ser Ala Ile Lys Gln Glu Leu His Ser Arg
        3700                3705                3710 gcc ttc ctg gcc atc acg cgg tct gag gag ctc tgg cca tgg atg gcc          11184
Ala Phe Leu Ala Ile Thr Arg Ser Glu Glu Leu Trp Pro Trp Met Ala
            3715                3720                3725 cac gtg ctg ctg ccc tac gtc cac ggg aac cag tcc agc cca gag ctg          11232
His Val Leu Leu Pro Tyr Val His Gly Asn Gln Ser Ser Pro Glu Leu
    3730                3735                3740 ggg ccc cca cgg ctg cgg cag gtg cgg ctg cag gaa gca ctc tac cca          11280
Gly Pro Pro Arg Leu Arg Gln Val Arg Leu Gln Glu Ala Leu Tyr Pro
3745                3750                3755                3760 gac cct ccc ggc ccc agg gtc cac acg tgc tcg gcc gca gga ggc ttc          11328
Asp Pro Pro Gly Pro Arg Val His Thr Cys Ser Ala Ala Gly Gly Phe
                3765                3770                3775 agc acc agc gat tac gac gtt ggc tgg gag agt cct cac aat ggc tcg          11376
Ser Thr Ser Asp Tyr Asp Val Gly Trp Glu Ser Pro His Asn Gly Ser
        3780                3785                3790 ggg acg tgg gcc tat tca gcg ccg gat ctg ctg ggg gca tgg tcc tgg          11424
Gly Thr Trp Ala Tyr Ser Ala Pro Asp Leu Leu Gly Ala Trp Ser Trp
            3795                3800                3805
```

```
ggc tcc tgt gcc gtg tat gac agc ggg ggc tac gtg cag gag ctg ggc      11472
Gly Ser Cys Ala Val Tyr Asp Ser Gly Gly Tyr Val Gln Glu Leu Gly
    3810                3815                3820 ctg agc ctg gag gag agc cgc gac cgg ctg cgc ttc ctg cag ctg cac      11520
Leu Ser Leu Glu Glu Ser Arg Asp Arg Leu Arg Phe Leu Gln Leu His
3825                3830                3835                3840 aac tgg ctg gac aac agg agc cgc gct gtg ttc ctg gag ctc acg cgc      11568
Asn Trp Leu Asp Asn Arg Ser Arg Ala Val Phe Leu Glu Leu Thr Arg
            3845                3850                3855 tac agc ccg gcc gtg ggg ctg cac gcc gcc gtc acg ctg cgc ctc gag      11616
Tyr Ser Pro Ala Val Gly Leu His Ala Ala Val Thr Leu Arg Leu Glu
        3860                3865                3870 ttc ccg gcg gcc ggc cgc gcc ctg gcc gcc ctc agc gtc cgc ccc ttt      11664
Phe Pro Ala Ala Gly Arg Ala Leu Ala Ala Leu Ser Val Arg Pro Phe
    3875                3880                3885 gcg ctg cgc cgc ctc agc gcg ggc ctc tcg ctg cct ctg ctc acc tcg      11712
Ala Leu Arg Arg Leu Ser Ala Gly Leu Ser Leu Pro Leu Leu Thr Ser
3890                3895                3900 gtg tgc ctg ctg ctg ttc gcc gtg cac ttc gcc gtg gcc gag gcc cgt      11760
Val Cys Leu Leu Leu Phe Ala Val His Phe Ala Val Ala Glu Ala Arg
3905                3910                3915                3920 act tgg cac agg gaa ggg cgc tgg cgc gtg ctg cgg ctc gga gcc tgg      11808
Thr Trp His Arg Glu Gly Arg Trp Arg Val Leu Arg Leu Gly Ala Trp
            3925                3930                3935 gcg cgg tgg ctg ctg gtg gcg ctg acg gcg gcc acg gca ctg gta cgc      11856
Ala Arg Trp Leu Leu Val Ala Leu Thr Ala Ala Thr Ala Leu Val Arg
        3940                3945                3950 ctc gcc cag ctg ggt gcc gct gac cgc cag tgg acc cgt ttc gtg cgc      11904
Leu Ala Gln Leu Gly Ala Ala Asp Arg Gln Trp Thr Arg Phe Val Arg
    3955                3960                3965 ggc cgc ccg cgc cgc ttc act agc ttc gac cag gtg gcg cac gtg agc      11952
Gly Arg Pro Arg Arg Phe Thr Ser Phe Asp Gln Val Ala His Val Ser
3970                3975                3980 tcc gca gcc cgt ggc ctg gcg gcc tcg ctg ctc ttc ctg ctt ttg gtc      12000
Ser Ala Ala Arg Gly Leu Ala Ala Ser Leu Leu Phe Leu Leu Leu Val
3985                3990                3995                4000 aag gct gcc cag cac gta cgc ttc gtg cgc cag tgg tcc gtc ttt ggc      12048
Lys Ala Ala Gln His Val Arg Phe Val Arg Gln Trp Ser Val Phe Gly
            4005                4010                4015 aag aca tta tgc cga gct ctg cca gag ctc ctg ggg gtc acc ttg ggc      12096
Lys Thr Leu Cys Arg Ala Leu Pro Glu Leu Leu Gly Val Thr Leu Gly
        4020                4025                4030 ctg gtg gtg ctc ggg gta gcc tac gcc cag ctg gcc atc ctg ctc gtg      12144
Leu Val Val Leu Gly Val Ala Tyr Ala Gln Leu Ala Ile Leu Leu Val
    4035                4040                4045 tct tcc tgt gtg gac tcc ctc tgg agc gtg gcc cag gcc ctg ttg gtg      12192
Ser Ser Cys Val Asp Ser Leu Trp Ser Val Ala Gln Ala Leu Leu Val
4050                4055                4060 ctg tgc cct ggg act ggg ctc tct acc ctg tgt cct gcc gag tcc tgg      12240
Leu Cys Pro Gly Thr Gly Leu Ser Thr Leu Cys Pro Ala Glu Ser Trp
4065                4070                4075                4080 cac ctg tca ccc ctg ctg tgt gtg ggg ctc tgg gca ctg cgg ctg tgg      12288
His Leu Ser Pro Leu Leu Cys Val Gly Leu Trp Ala Leu Arg Leu Trp
            4085                4090                4095 ggc gcc cta cgg ctg ggg gct gtt att ctc cgc tgg cgc tac cac gcc      12336
Gly Ala Leu Arg Leu Gly Ala Val Ile Leu Arg Trp Arg Tyr His Ala
        4100                4105                4110 ttg cgt gga gag ctg tac cgg ccg gcc tgg gag ccc cag gac tac gag      12384
Leu Arg Gly Glu Leu Tyr Arg Pro Ala Trp Glu Pro Gln Asp Tyr Glu
    4115                4120                4125
```

-continued

```
atg gtg gag ttg ttc ctg cgc agg ctg cgc ctc tgg atg ggc ctc agc    12432
Met Val Glu Leu Phe Leu Arg Arg Leu Arg Leu Trp Met Gly Leu Ser
    4130                4135                4140 aag gtc aag gag ttc cgc cac aaa gtc cgc ttt gaa ggg atg gag ccg    12480
Lys Val Lys Glu Phe Arg His Lys Val Arg Phe Glu Gly Met Glu Pro
4145                4150                4155                4160 ctg ccc tct cgc tcc tcc agg ggc tcc aag gta tcc ccg gat gtg ccc    12528
Leu Pro Ser Arg Ser Ser Arg Gly Ser Lys Val Ser Pro Asp Val Pro
            4165                4170                4175 cca ccc agc gct ggc tcc gat gcc tcg cac ccc tcc acc tcc tcc agc    12576
Pro Pro Ser Ala Gly Ser Asp Ala Ser His Pro Ser Thr Ser Ser Ser
        4180                4185                4190 cag ctg gat ggg ctg agc gtg agc ctg ggc cgg ctg ggg aca agg tgt    12624
Gln Leu Asp Gly Leu Ser Val Ser Leu Gly Arg Leu Gly Thr Arg Cys
    4195                4200                4205 gag cct gag ccc tcc cgc ctc caa gcc gtg ttc gag gcc ctg ctc acc    12672
Glu Pro Glu Pro Ser Arg Leu Gln Ala Val Phe Glu Ala Leu Leu Thr
    4210                4215                4220 cag ttt gac cga ctc aac cag gcc aca gag gac gtc tac cag ctg gag    12720
Gln Phe Asp Arg Leu Asn Gln Ala Thr Glu Asp Val Tyr Gln Leu Glu
4225                4230                4235                4240 cag cag ctg cac agc ctg caa ggc cgc agg agc agc cgg gcg ccc gcc    12768
Gln Gln Leu His Ser Leu Gln Gly Arg Arg Ser Ser Arg Ala Pro Ala
            4245                4250                4255 gga tct tcc cgt ggc cca tcc ccg ggc ctg cgg cca gca ctg ccc agc    12816
Gly Ser Ser Arg Gly Pro Ser Pro Gly Leu Arg Pro Ala Leu Pro Ser
        4260                4265                4270 cgc ctt gcc cgg gcc agt cgg ggt gtg gac ctg gcc act ggc ccc agc    12864
Arg Leu Ala Arg Ala Ser Arg Gly Val Asp Leu Ala Thr Gly Pro Ser
    4275                4280                4285 agg aca ccc ctt cgg gcc aag aac aag gtc cac ccc agc agc act tag    12912
Arg Thr Pro Leu Arg Ala Lys Asn Lys Val His Pro Ser Ser Thr
    4290                4295                4300

<210> SEQ ID NO 2
<211> LENGTH: 4303
<212> TYPE: PRT
<213> ORGANISM: Homo sapiens PKD-1 protein

<400> SEQUENCE: 2

Met Pro Pro Ala Ala Pro Ala Arg Leu Ala Leu Ala Leu Gly Leu Gly
 1               5                   10                  15

Leu Trp Leu Gly Ala Leu Ala Gly Gly Pro Gly Arg Gly Cys Gly Pro
                20                  25                  30

Cys Glu Pro Pro Cys Leu Cys Gly Pro Ala Pro Gly Ala Ala Cys Arg
            35                  40                  45

Val Asn Cys Ser Gly Arg Gly Leu Arg Thr Leu Gly Pro Ala Leu Arg
        50                  55                  60

Ile Pro Ala Asp Ala Thr Glu Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Gln Trp Ala Glu Glu Gln Gln
    130                 135                 140
```

-continued

```
Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Ala Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Asp Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
        435                 440                 445

Ser Pro Ala Val Gln Arg Phe Leu Val Ser Arg Val Thr Arg Ser Leu
450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
        515                 520                 525

Val Cys Glu Leu Gln Pro Gly Gly Pro Val Gln Asp Ala Glu Asn Leu
    530                 535                 540

Leu Val Gly Ala Pro Ser Gly Asp Leu Gln Gly Pro Leu Thr Pro Leu
545                 550                 555                 560
```

```
Ala Gln Gln Asp Gly Leu Ser Ala Pro His Glu Pro Val Glu Val Met
            565                 570                 575

Val Phe Pro Gly Leu Arg Leu Ser Arg Glu Ala Phe Leu Thr Thr Ala
            580                 585                 590

Glu Phe Gly Thr Gln Glu Leu Arg Arg Pro Ala Gln Leu Arg Leu Gln
            595                 600                 605

Val Tyr Arg Leu Leu Ser Thr Ala Gly Thr Pro Glu Asn Gly Ser Glu
            610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
            645                 650                 655

Asp Ala Ser Cys His Pro Gln Ala Cys Ala Asn Gly Cys Thr Ser Gly
            660                 665                 670

Pro Gly Leu Pro Gly Ala Pro Tyr Ala Leu Trp Arg Glu Phe Leu Phe
            675                 680                 685

Ser Val Pro Ala Gly Pro Pro Ala Gln Tyr Ser Val Thr Leu His Gly
            690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
            725                 730                 735

Gly Pro Arg Ala Pro Tyr Leu Ser Ala Asn Ala Ser Ser Trp Leu Pro
            740                 745                 750

His Leu Pro Ala Gln Leu Glu Gly Thr Trp Gly Cys Pro Ala Cys Ala
            755                 760                 765

Leu Arg Leu Leu Ala Gln Arg Glu Gln Leu Thr Val Leu Leu Gly Leu
            770                 775                 780

Arg Pro Asn Pro Gly Leu Arg Leu Pro Gly Arg Tyr Glu Val Arg Ala
785                 790                 795                 800

Glu Val Gly Asn Gly Val Ser Arg His Asn Leu Ser Cys Ser Phe Asp
            805                 810                 815

Val Val Ser Pro Val Ala Gly Leu Arg Val Ile Tyr Pro Ala Pro Arg
            820                 825                 830

Asp Gly Arg Leu Tyr Val Pro Thr Asn Gly Ser Ala Leu Val Leu Gln
            835                 840                 845

Val Asp Ser Gly Ala Asn Ala Thr Ala Thr Ala Arg Trp Pro Gly Gly
            850                 855                 860

Ser Leu Ser Ala Arg Phe Glu Asn Val Cys Pro Ala Leu Val Ala Thr
865                 870                 875                 880

Phe Val Pro Ala Cys Pro Trp Glu Thr Asn Asp Thr Leu Phe Ser Val
            885                 890                 895

Val Ala Leu Pro Trp Leu Ser Glu Gly Glu His Val Val Asp Val Val
            900                 905                 910

Val Glu Asn Ser Ala Ser Arg Ala Asn Leu Ser Leu Arg Val Thr Ala
            915                 920                 925

Glu Glu Pro Ile Cys Gly Leu Arg Ala Thr Pro Ser Pro Glu Ala Arg
            930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
            965                 970                 975

Phe Gln Asn Val Val Phe Asn Val Ile Tyr Gln Ser Ala Ala Val Phe
```

-continued

```
                  980              985              990
Lys Leu Ser Leu Thr Ala Ser Asn His Val Ser Asn Val Thr Val Asn
            995              1000             1005

Tyr Asn Val Thr Val Glu Arg Met Asn Arg Met Gln Gly Leu Gln Val
    1010             1015             1020

Ser Thr Val Pro Ala Val Leu Ser Pro Asn Ala Thr Leu Ala Leu Thr
1025             1030             1035             1040

Ala Gly Val Leu Val Asp Ser Ala Val Glu Val Ala Phe Leu Trp Thr
            1045             1050             1055

Phe Gly Asp Gly Glu Gln Ala Leu His Gln Phe Gln Pro Pro Tyr Asn
            1060             1065             1070

Glu Ser Phe Pro Val Pro Asp Pro Ser Val Ala Gln Val Leu Val Glu
    1075             1080             1085

His Asn Val Thr His Thr Tyr Ala Ala Pro Gly Glu Tyr Leu Leu Thr
    1090             1095             1100

Val Leu Ala Ser Asn Ala Phe Glu Asn Leu Thr Gln Gln Val Pro Val
1105             1110             1115             1120

Ser Val Arg Ala Ser Leu Pro Ser Val Ala Val Gly Val Ser Asp Gly
            1125             1130             1135

Val Leu Val Ala Gly Arg Pro Val Thr Phe Tyr Pro His Pro Leu Pro
            1140             1145             1150

Ser Pro Gly Gly Val Leu Tyr Thr Trp Asp Phe Gly Asp Gly Ser Pro
            1155             1160             1165

Val Leu Thr Gln Ser Gln Pro Ala Ala Asn His Thr Tyr Ala Ser Arg
    1170             1175             1180

Gly Thr Tyr His Val Arg Leu Glu Val Asn Asn Thr Val Ser Gly Ala
1185             1190             1195             1200

Ala Ala Gln Ala Asp Val Arg Val Phe Glu Glu Leu Arg Gly Leu Ser
            1205             1210             1215

Val Asp Met Ser Leu Ala Val Glu Gln Gly Ala Pro Val Val Val Ser
            1220             1225             1230

Ala Ala Val Gln Thr Gly Asp Asn Ile Thr Trp Thr Phe Asp Met Gly
            1235             1240             1245

Asp Gly Thr Val Leu Ser Gly Pro Glu Ala Thr Val Glu His Val Tyr
    1250             1255             1260

Leu Arg Ala Gln Asn Cys Thr Val Thr Val Gly Ala Gly Ser Pro Ala
1265             1270             1275             1280

Gly His Leu Ala Arg Ser Leu His Val Leu Phe Val Leu Glu Val
            1285             1290             1295

Leu Arg Val Glu Pro Ala Ala Cys Ile Pro Thr Gln Pro Asp Ala Arg
            1300             1305             1310

Leu Thr Ala Tyr Val Thr Gly Asn Pro Ala His Tyr Leu Phe Asp Trp
            1315             1320             1325

Thr Phe Gly Asp Gly Ser Ser Asn Thr Thr Val Arg Gly Cys Pro Thr
    1330             1335             1340

Val Thr His Asn Phe Thr Arg Ser Gly Thr Phe Pro Leu Ala Leu Val
1345             1350             1355             1360

Leu Ser Ser Arg Val Asn Arg Ala His Tyr Phe Thr Ser Ile Cys Val
            1365             1370             1375

Glu Pro Glu Val Gly Asn Val Thr Leu Gln Pro Glu Arg Gln Phe Val
        1380             1385             1390

Gln Leu Gly Asp Glu Ala Trp Leu Val Ala Cys Ala Trp Pro Pro Phe
            1395             1400             1405
```

-continued

```
Pro Tyr Arg Tyr Thr Trp Asp Phe Gly Thr Glu Glu Ala Ala Pro Thr
    1410                1415                1420
Arg Ala Arg Gly Pro Glu Val Thr Phe Ile Tyr Arg Asp Pro Gly Ser
1425            1430                1435                1440
Tyr Leu Val Thr Val Thr Ala Ser Asn Asn Ile Ser Ala Ala Asn Asp
            1445                1450                1455
Ser Ala Leu Val Glu Val Gln Glu Pro Val Leu Val Thr Ser Ile Lys
        1460                1465                1470
Val Asn Gly Ser Leu Gly Leu Glu Leu Gln Gln Pro Tyr Leu Phe Ser
        1475                1480                1485
Ala Val Gly Arg Gly Arg Pro Ala Ser Tyr Leu Trp Asp Leu Gly Asp
        1490                1495                1500
Gly Gly Trp Leu Glu Gly Pro Glu Val Thr His Ala Tyr Asn Ser Thr
1505            1510                1515                1520
Gly Asp Phe Thr Val Arg Val Ala Gly Trp Asn Glu Val Ser Arg Ser
            1525                1530                1535
Glu Ala Trp Leu Asn Val Thr Val Lys Arg Arg Val Arg Gly Leu Val
        1540                1545                1550
Val Asn Ala Ser Arg Thr Val Val Pro Leu Asn Gly Ser Val Ser Phe
        1555                1560                1565
Ser Thr Ser Leu Glu Ala Gly Ser Asp Val Arg Tyr Ser Trp Val Leu
    1570                1575                1580
Cys Asp Arg Cys Thr Pro Ile Pro Gly Gly Pro Thr Ile Ser Tyr Thr
1585            1590                1595                1600
Phe Arg Ser Val Gly Thr Phe Asn Ile Ile Val Thr Ala Glu Asn Glu
            1605                1610                1615
Val Gly Ser Ala Gln Asp Ser Ile Phe Val Tyr Val Leu Gln Leu Ile
        1620                1625                1630
Glu Gly Leu Gln Val Val Gly Gly Arg Tyr Phe Pro Thr Asn His
        1635                1640                1645
Thr Val Gln Leu Gln Ala Val Val Arg Asp Gly Thr Asn Val Ser Tyr
    1650                1655                1660
Ser Trp Thr Ala Trp Arg Asp Arg Gly Pro Ala Leu Ala Gly Ser Gly
1665            1670                1675                1680
Lys Gly Phe Ser Leu Thr Val Leu Glu Ala Gly Thr Tyr His Val Gln
            1685                1690                1695
Leu Arg Ala Thr Asn Met Leu Gly Ser Ala Trp Ala Asp Cys Thr Met
        1700                1705                1710
Asp Phe Val Glu Pro Val Gly Trp Leu Met Val Ala Ala Ser Pro Asn
        1715                1720                1725
Pro Ala Ala Val Asn Thr Ser Val Thr Leu Ser Ala Glu Leu Ala Gly
        1730                1735                1740
Gly Ser Gly Val Val Tyr Thr Trp Ser Leu Glu Gly Leu Ser Trp
1745            1750                1755                1760
Glu Thr Ser Glu Pro Phe Thr Thr His Ser Phe Pro Thr Pro Gly Leu
            1765                1770                1775
His Leu Val Thr Met Thr Ala Gly Asn Pro Leu Gly Ser Ala Asn Ala
            1780                1785                1790
Thr Val Glu Val Asp Val Gln Val Pro Val Ser Gly Leu Ser Ile Arg
        1795                1800                1805
Ala Ser Glu Pro Gly Gly Ser Phe Val Ala Ala Gly Ser Ser Val Pro
        1810                1815                1820
```

-continued

```
Phe Trp Gly Gln Leu Ala Thr Gly Thr Asn Val Ser Trp Cys Trp Ala
1825                1830                1835                1840

Val Pro Gly Gly Ser Ser Lys Arg Gly Pro His Val Thr Met Val Phe
                1845                1850                1855

Pro Asp Ala Gly Thr Phe Ser Ile Arg Leu Asn Ala Ser Asn Ala Val
            1860                1865                1870

Ser Trp Val Ser Ala Thr Tyr Asn Leu Thr Ala Glu Glu Pro Ile Val
        1875                1880                1885

Gly Leu Val Leu Trp Ala Ser Ser Lys Val Val Ala Pro Gly Gln Leu
    1890                1895                1900

Val His Phe Gln Ile Leu Leu Ala Ala Gly Ser Ala Val Thr Phe Arg
905                1910                1915                1920

Leu Gln Val Gly Gly Ala Asn Pro Glu Val Leu Pro Gly Pro Arg Phe
                1925                1930                1935

Ser His Ser Phe Pro Arg Val Gly Asp His Val Val Ser Val Arg Gly
            1940                1945                1950

Lys Asn His Val Ser Trp Ala Gln Ala Gln Val Arg Ile Val Val Leu
        1955                1960                1965

Glu Ala Val Ser Gly Leu Gln Val Pro Asn Cys Cys Glu Pro Gly Ile
    1970                1975                1980

Ala Thr Gly Thr Glu Arg Asn Phe Thr Ala Arg Val Gln Arg Gly Ser
1985                1990                1995                2000

Arg Val Ala Tyr Ala Trp Tyr Phe Ser Leu Gln Lys Val Gln Gly Asp
                2005                2010                2015

Ser Leu Val Ile Leu Ser Gly Arg Asp Val Thr Tyr Thr Pro Val Ala
            2020                2025                2030

Ala Gly Leu Leu Glu Ile Gln Val Arg Ala Phe Asn Ala Leu Gly Ser
        2035                2040                2045

Glu Asn Arg Thr Leu Val Leu Glu Val Gln Asp Ala Val Gln Tyr Val
    2050                2055                2060

Ala Leu Gln Ser Gly Pro Cys Phe Thr Asn Arg Ser Ala Gln Phe Glu
2065                2070                2075                2080

Ala Ala Thr Ser Pro Ser Pro Arg Arg Val Ala Tyr His Trp Asp Phe
                2085                2090                2095

Gly Asp Gly Ser Pro Gly Gln Asp Thr Asp Glu Pro Arg Ala Glu His
            2100                2105                2110

Ser Tyr Leu Arg Pro Gly Asp Tyr Arg Val Gln Val Asn Ala Ser Asn
        2115                2120                2125

Leu Val Ser Phe Phe Val Ala Gln Ala Thr Val Thr Val Gln Val Leu
    2130                2135                2140

Ala Cys Arg Glu Pro Glu Val Asp Val Val Leu Pro Leu Gln Val Leu
2145                2150                2155                2160

Met Arg Arg Ser Gln Arg Asn Tyr Leu Glu Ala His Val Asp Leu Arg
                2165                2170                2175

Asp Cys Val Thr Tyr Gln Thr Glu Tyr Arg Trp Glu Val Tyr Arg Thr
            2180                2185                2190

Ala Ser Cys Gln Arg Pro Gly Arg Pro Ala Arg Val Ala Leu Pro Gly
        2195                2200                2205

Val Asp Val Ser Arg Pro Arg Leu Val Leu Pro Arg Leu Ala Leu Pro
    2210                2215                2220

Val Gly His Tyr Cys Phe Val Phe Val Val Ser Phe Gly Asp Thr Pro
2225                2230                2235                2240

Leu Thr Gln Ser Ile Gln Ala Asn Val Thr Val Ala Pro Glu Arg Leu
```

-continued

```
                2245                2250                 2255
Val Pro Ile Ile Glu Gly Gly Ser Tyr Arg Val Trp Ser Asp Thr Arg
            2260                2265                2270
Asp Leu Val Leu Asp Gly Ser Glu Ser Tyr Asp Pro Asn Leu Glu Asp
            2275                2280                2285
Gly Asp Gln Thr Pro Leu Ser Phe His Trp Ala Cys Val Ala Ser Thr
            2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Glu Arg Leu Ala Ala Gly Val Glu Tyr
            2325                2330                2335
Thr Phe Ser Leu Thr Val Trp Lys Ala Gly Arg Lys Glu Glu Ala Thr
            2340                2345                2350
Asn Gln Thr Val Leu Ile Arg Ser Gly Arg Val Pro Ile Val Ser Leu
            2355                2360                2365
Glu Cys Val Ser Cys Lys Ala Gln Ala Val Tyr Glu Val Ser Arg Ser
            2370                2375                2380
Ser Tyr Val Tyr Leu Glu Gly Arg Cys Leu Asn Cys Ser Ser Gly Ser
2385                2390                2395                2400
Lys Arg Gly Arg Trp Ala Ala Arg Thr Phe Ser Asn Lys Thr Leu Val
            2405                2410                2415
Leu Asp Glu Thr Thr Thr Ser Thr Gly Ser Ala Gly Met Arg Leu Val
            2420                2425                2430
Leu Arg Arg Gly Val Leu Arg Asp Gly Glu Gly Tyr Thr Phe Thr Leu
            2435                2440                2445
Thr Val Leu Gly Arg Ser Gly Glu Glu Glu Gly Cys Ala Ser Ile Arg
            2450                2455                2460
Leu Ser Pro Asn Arg Pro Pro Leu Gly Gly Ser Cys Arg Leu Phe Pro
2465                2470                2475                2480
Leu Gly Ala Val His Ala Leu Thr Thr Lys Val His Phe Glu Cys Thr
            2485                2490                2495
Gly Trp His Asp Ala Glu Asp Ala Gly Ala Pro Leu Val Tyr Ala Leu
            2500                2505                2510
Leu Leu Arg Arg Cys Arg Gln Gly His Cys Glu Glu Phe Cys Val Tyr
            2515                2520                2525
Lys Gly Ser Leu Ser Ser Tyr Gly Ala Val Leu Pro Pro Gly Phe Arg
            2530                2535                2540
Pro His Phe Glu Val Gly Leu Ala Val Val Gln Asp Gln Leu Gly
2545                2550                2555                2560
Ala Ala Val Val Ala Leu Asn Arg Ser Leu Ala Ile Thr Leu Pro Glu
            2565                2570                2575
Pro Asn Gly Ser Ala Thr Gly Leu Thr Val Trp Leu His Gly Leu Thr
            2580                2585                2590
Ala Ser Val Leu Pro Gly Leu Leu Arg Gln Ala Asp Pro Gln His Val
            2595                2600                2605
Ile Glu Tyr Ser Leu Ala Leu Val Thr Val Leu Asn Glu Tyr Glu Arg
            2610                2615                2620
Ala Leu Asp Val Ala Ala Glu Pro Lys His Glu Arg Gln His Arg Ala
2625                2630                2635                2640
Gln Ile Arg Lys Asn Ile Thr Glu Thr Leu Val Ser Leu Arg Val His
            2645                2650                2655
Thr Val Asp Asp Ile Gln Gln Ile Ala Ala Ala Leu Ala Gln Cys Met
            2660                2665                2670
```

-continued

```
Gly Pro Ser Arg Glu Leu Val Cys Arg Ser Cys Leu Lys Gln Thr Leu
        2675            2680            2685
His Lys Leu Glu Ala Met Met Leu Ile Leu Gln Ala Glu Thr Thr Ala
    2690            2695            2700
Gly Thr Val Thr Pro Thr Ala Ile Gly Asp Ser Ile Leu Asn Ile Thr
2705            2710            2715            2720
Gly Asp Leu Ile His Leu Ala Ser Ser Asp Val Arg Ala Pro Gln Pro
            2725            2730            2735
Ser Glu Leu Gly Ala Glu Ser Pro Ser Arg Met Val Ala Ser Gln Ala
        2740            2745            2750
Tyr Asn Leu Thr Ser Ala Leu Met Arg Ile Leu Met Arg Ser Arg Val
    2755            2760            2765
Leu Asn Glu Glu Pro Leu Thr Leu Ala Gly Glu Glu Ile Val Ala Gln
    2770            2775            2780
Gly Lys Arg Ser Asp Pro Arg Ser Leu Leu Cys Tyr Gly Gly Ala Pro
2785            2790            2795            2800
Gly Pro Gly Cys His Phe Ser Ile Pro Glu Ala Phe Ser Gly Ala Leu
            2805            2810            2815
Ala Asn Leu Ser Asp Val Val Gln Leu Ile Phe Leu Val Asp Ser Asn
            2820            2825            2830
Pro Phe Pro Phe Gly Tyr Ile Ser Asn Tyr Thr Val Ser Thr Lys Val
        2835            2840            2845
Ala Ser Met Ala Phe Gln Thr Gln Ala Gly Ala Gln Ile Pro Ile Glu
    2850            2855            2860
Arg Leu Ala Ser Glu Arg Ala Ile Thr Val Lys Val Pro Asn Asn Ser
2865            2870            2875            2880
Asp Trp Ala Ala Arg Gly His Arg Ser Ser Ala Asn Ser Ala Asn Ser
            2885            2890            2895
Val Val Val Gln Pro Gln Ala Ser Val Gly Ala Val Val Thr Leu Asp
            2900            2905            2910
Ser Ser Asn Pro Ala Ala Gly Leu His Leu Gln Leu Asn Tyr Thr Leu
        2915            2920            2925
Leu Asp Gly His Tyr Leu Ser Glu Glu Pro Glu Pro Tyr Leu Ala Val
    2930            2935            2940
Tyr Leu His Ser Glu Pro Arg Pro Asn Glu His Asn Cys Ser Ala Ser
2945            2950            2955            2960
Arg Arg Ile Arg Pro Glu Ser Leu Gln Gly Ala Asp His Arg Pro Tyr
            2965            2970            2975
Thr Phe Phe Ile Ser Pro Gly Ser Arg Asp Pro Ala Gly Ser Tyr His
            2980            2985            2990
Leu Asn Leu Ser Ser His Phe Arg Trp Ser Ala Leu Gln Val Ser Val
        2995            3000            3005
Gly Leu Tyr Thr Ser Leu Cys Gln Tyr Phe Ser Glu Glu Asp Met Val
    3010            3015            3020
Trp Arg Thr Glu Gly Leu Leu Pro Leu Glu Glu Thr Ser Pro Arg Gln
3025            3030            3035            3040
Ala Val Cys Leu Thr Arg His Leu Thr Ala Phe Gly Ala Ser Leu Phe
            3045            3050            3055
Val Pro Pro Ser His Val Arg Phe Val Phe Pro Glu Pro Thr Ala Asp
            3060            3065            3070
Val Asn Tyr Ile Val Met Leu Thr Cys Ala Val Cys Leu Val Thr Tyr
        3075            3080            3085
```

-continued

```
Met Val Met Ala Ala Ile Leu His Lys Leu Asp Gln Leu Asp Ala Ser
    3090                3095                3100

Arg Gly Arg Ala Ile Pro Phe Cys Gly Gln Arg Gly Arg Phe Lys Tyr
3105                3110                3115                3120

Glu Ile Leu Val Lys Thr Gly Trp Gly Arg Gly Ser Gly Thr Thr Ala
                3125                3130                3135

His Val Gly Ile Met Leu Tyr Gly Val Asp Ser Arg Ser Gly His Arg
            3140                3145                3150

His Leu Asp Gly Asp Arg Ala Phe His Arg Asn Ser Leu Asp Ile Phe
        3155                3160                3165

Arg Ile Ala Thr Pro His Ser Leu Gly Ser Val Trp Lys Ile Arg Val
    3170                3175                3180

Trp His Asp Asn Lys Gly Leu Ser Pro Ala Trp Phe Leu Gln His Val
3185                3190                3195                3200

Ile Val Arg Asp Leu Gln Thr Ala Arg Ser Ala Phe Phe Leu Val Asn
                3205                3210                3215

Asp Trp Leu Ser Val Glu Thr Glu Ala Asn Gly Gly Leu Val Glu Lys
            3220                3225                3230

Glu Val Leu Ala Ala Ser Asp Ala Ala Leu Leu Arg Phe Arg Arg Leu
        3235                3240                3245

Leu Val Ala Glu Leu Gln Arg Gly Phe Phe Asp Lys His Ile Trp Leu
    3250                3255                3260

Ser Ile Trp Asp Arg Pro Pro Arg Ser Arg Phe Thr Arg Ile Gln Arg
3265                3270                3275                3280

Ala Thr Cys Cys Val Leu Leu Ile Cys Leu Phe Leu Gly Ala Asn Ala
                3285                3290                3295

Val Trp Tyr Gly Ala Val Gly Asp Ser Ala Tyr Ser Thr Gly His Val
            3300                3305                3310

Ser Arg Leu Ser Pro Leu Ser Val Asp Thr Val Ala Val Gly Leu Val
        3315                3320                3325

Ser Ser Val Val Val Tyr Pro Val Tyr Leu Ala Ile Leu Phe Leu Phe
    3330                3335                3340

Arg Met Ser Arg Ser Lys Val Ala Gly Ser Pro Ser Pro Thr Pro Ala
3345                3350                3355                3360

Gly Gln Gln Val Leu Asp Ile Asp Ser Cys Leu Asp Ser Ser Val Leu
            3365                3370                3375

Asp Ser Ser Phe Leu Thr Phe Ser Gly Leu His Ala Glu Gln Ala Phe
        3380                3385                3390

Val Gly Gln Met Lys Ser Asp Leu Phe Leu Asp Asp Ser Lys Ser Leu
    3395                3400                3405

Val Cys Trp Pro Ser Gly Glu Gly Thr Leu Ser Trp Pro Asp Leu Leu
    3410                3415                3420

Ser Asp Pro Ser Ile Val Gly Ser Asn Leu Arg Gln Leu Ala Arg Gly
3425                3430                3435                3440

Gln Ala Gly His Gly Leu Gly Pro Glu Glu Asp Gly Phe Ser Leu Ala
                3445                3450                3455

Ser Pro Tyr Ser Pro Ala Lys Ser Phe Ser Ala Ser Asp Glu Asp Leu
            3460                3465                3470

Ile Gln Gln Val Leu Ala Glu Gly Val Ser Ser Pro Ala Pro Thr Gln
        3475                3480                3485

Asp Thr His Met Glu Thr Asp Leu Leu Ser Ser Leu Ser Ser Thr Pro
    3490                3495                3500

Gly Glu Lys Thr Glu Thr Leu Ala Leu Gln Arg Leu Gly Glu Leu Gly
```

-continued

```
3505                3510                3515                3520

Pro Pro Ser Pro Gly Leu Asn Trp Glu Gln Pro Gln Ala Ala Arg Leu
            3525                3530                3535

Ser Arg Thr Gly Leu Val Glu Gly Leu Arg Lys Arg Leu Leu Pro Ala
            3540                3545                3550

Trp Cys Ala Ser Leu Ala His Gly Leu Ser Leu Leu Val Ala Val
            3555                3560                3565

Ala Val Ala Val Ser Gly Trp Val Gly Ala Ser Phe Pro Pro Gly Val
            3570                3575                3580

Ser Val Ala Trp Leu Leu Ser Ser Ser Ala Ser Phe Leu Ala Ser Phe
3585                3590                3595                3600

Leu Gly Trp Glu Pro Leu Lys Val Leu Leu Glu Ala Leu Tyr Phe Ser
            3605                3610                3615

Leu Val Ala Lys Arg Leu His Pro Asp Glu Asp Asp Thr Leu Val Glu
            3620                3625                3630

Ser Pro Ala Val Thr Pro Val Ser Ala Arg Val Pro Arg Val Arg Pro
            3635                3640                3645

Pro His Gly Phe Ala Leu Phe Leu Ala Lys Glu Glu Ala Arg Lys Val
            3650                3655                3660

Lys Arg Leu His Gly Met Leu Arg Ser Leu Leu Val Tyr Met Leu Phe
3665                3670                3675                3680

Leu Leu Val Thr Leu Leu Ala Ser Tyr Gly Asp Ala Ser Cys His Gly
            3685                3690                3695

His Ala Tyr Arg Leu Gln Ser Ala Ile Lys Gln Glu Leu His Ser Arg
            3700                3705                3710

Ala Phe Leu Ala Ile Thr Arg Ser Glu Glu Leu Trp Pro Trp Met Ala
            3715                3720                3725

His Val Leu Leu Pro Tyr Val His Gly Asn Gln Ser Ser Pro Glu Leu
            3730                3735                3740

Gly Pro Pro Arg Leu Arg Gln Val Arg Leu Gln Glu Ala Leu Tyr Pro
3745                3750                3755                3760

Asp Pro Pro Gly Pro Arg Val His Thr Cys Ser Ala Ala Gly Gly Phe
            3765                3770                3775

Ser Thr Ser Asp Tyr Asp Val Gly Trp Glu Ser Pro His Asn Gly Ser
            3780                3785                3790

Gly Thr Trp Ala Tyr Ser Ala Pro Asp Leu Leu Gly Ala Trp Ser Trp
            3795                3800                3805

Gly Ser Cys Ala Val Tyr Asp Ser Gly Gly Tyr Val Gln Glu Leu Gly
            3810                3815                3820

Leu Ser Leu Glu Glu Ser Arg Asp Arg Leu Arg Phe Leu Gln Leu His
3825                3830                3835                3840

Asn Trp Leu Asp Asn Arg Ser Arg Ala Val Phe Leu Glu Leu Thr Arg
            3845                3850                3855

Tyr Ser Pro Ala Val Gly Leu His Ala Ala Val Thr Leu Arg Leu Glu
            3860                3865                3870

Phe Pro Ala Ala Gly Arg Ala Leu Ala Ala Leu Ser Val Arg Pro Phe
            3875                3880                3885

Ala Leu Arg Arg Leu Ser Ala Gly Leu Ser Leu Pro Leu Leu Thr Ser
            3890                3895                3900

Val Cys Leu Leu Leu Phe Ala Val His Phe Ala Val Ala Glu Ala Arg
3905                3910                3915                3920

Thr Trp His Arg Glu Gly Arg Trp Arg Val Leu Arg Leu Gly Ala Trp
            3925                3930                3935
```

```
Ala Arg Trp Leu Leu Val Ala Leu Thr Ala Thr Ala Leu Val Arg
        3940                3945                3950

Leu Ala Gln Leu Gly Ala Ala Asp Arg Gln Trp Thr Arg Phe Val Arg
        3955                3960                3965

Gly Arg Pro Arg Arg Phe Thr Ser Phe Asp Gln Val Ala His Val Ser
        3970                3975                3980

Ser Ala Ala Arg Gly Leu Ala Ala Ser Leu Leu Phe Leu Leu Leu Val
3985                3990                3995                4000

Lys Ala Ala Gln His Val Arg Phe Val Arg Gln Trp Ser Val Phe Gly
        4005                4010                4015

Lys Thr Leu Cys Arg Ala Leu Pro Glu Leu Leu Gly Val Thr Leu Gly
        4020                4025                4030

Leu Val Val Leu Gly Val Ala Tyr Ala Gln Leu Ala Ile Leu Leu Val
        4035                4040                4045

Ser Ser Cys Val Asp Ser Leu Trp Ser Val Ala Gln Ala Leu Leu Val
        4050                4055                4060

Leu Cys Pro Gly Thr Gly Leu Ser Thr Leu Cys Pro Ala Glu Ser Trp
4065                4070                4075                4080

His Leu Ser Pro Leu Leu Cys Val Gly Leu Trp Ala Leu Arg Leu Trp
        4085                4090                4095

Gly Ala Leu Arg Leu Gly Ala Val Ile Leu Arg Trp Arg Tyr His Ala
        4100                4105                4110

Leu Arg Gly Glu Leu Tyr Arg Pro Ala Trp Glu Pro Gln Asp Tyr Glu
        4115                4120                4125

Met Val Glu Leu Phe Leu Arg Arg Leu Arg Leu Trp Met Gly Leu Ser
        4130                4135                4140

Lys Val Lys Glu Phe Arg His Lys Val Arg Phe Glu Gly Met Glu Pro
4145                4150                4155                4160

Leu Pro Ser Arg Ser Ser Arg Gly Ser Lys Val Ser Pro Asp Val Pro
        4165                4170                4175

Pro Pro Ser Ala Gly Ser Asp Ala Ser His Pro Ser Thr Ser Ser Ser
        4180                4185                4190

Gln Leu Asp Gly Leu Ser Val Ser Leu Gly Arg Leu Gly Thr Arg Cys
        4195                4200                4205

Glu Pro Glu Pro Ser Arg Leu Gln Ala Val Phe Glu Ala Leu Leu Thr
        4210                4215                4220

Gln Phe Asp Arg Leu Asn Gln Ala Thr Glu Asp Val Tyr Gln Leu Glu
4225                4230                4235                4240

Gln Gln Leu His Ser Leu Gln Gly Arg Arg Ser Ser Arg Ala Pro Ala
        4245                4250                4255

Gly Ser Ser Arg Gly Pro Ser Pro Gly Leu Arg Pro Ala Leu Pro Ser
        4260                4265                4270

Arg Leu Ala Arg Ala Ser Arg Gly Val Asp Leu Ala Thr Gly Pro Ser
        4275                4280                4285

Arg Thr Pro Leu Arg Ala Lys Asn Lys Val His Pro Ser Ser Thr
        4290                4295                4300

<210> SEQ ID NO 3
<211> LENGTH: 12685
<212> TYPE: DNA
<213> ORGANISM: C. Elegans lov-1 gene

<400> SEQUENCE: 3
tcaatctttc tccacatcgt ttagccgcca cttctggaat ctctttggtc cagtttcgtg      60
```

-continued

```
aatagcagag acaggatcat aggagagtgt gtagttgatg actgtttggt tttggtattg    120
accttgagtt tggagcattc tggtggcacg atgatgaagc agattgactt tggcaacagc    180
gctgtggaat agacggaagt cttttgagt gtcagcaatt gaaactggag caaaatcttt     240
tggttcaaga agacccaagc gacgttttgt ctgaaattaa ataacagaaa ttaaagaaca    300
tctaatagtg agcttgaaaa ataaatacct tgtattttat gtgatcgatt atttcgtaat    360
cattggtctg cttctcactg tcattacgaa tttcctcgaa ctcgaacata attatagtga    420
cgtaaagttg caggacgagc tttgatccgg caatcatata aagcatgatc acaacaaacg    480
caaattgaga atcggttga atagaggtaa catcaagttt tccaagcatt ccagccaatg     540
ctgtttgaaa ggtagccatt aagctccgat atctggaacc aattttaaa aattgatttc     600
tttcaattaa gttttcatcc tcaccctccc attttatttc ctaaaactgc gtacaataca    660
gagttgaatg tcatgctgaa gaacaggaaa gcaattccaa atgacacaat agctccgaga    720
gcgttatcca gtgtagccgc taatactcca attcttctgt tgaatctcaa gattcgaatc    780
attttacaag aagtgaagaa tacggctccg gcaagacaat aactgaatac aatctcccaa    840
tttctctgtt cagtcaaatt aatgtacgaa tttccattgt ttgcattgaa atcttccatt    900
gctctatttg tggttcgttg gcggatggtg taggctagga ccgatgcaac agcgagagct    960
ccaactatca agtccatgaa gttccatggt gagaagtttc tataaaatgt cttttgaaa    1020
ctgaagttct cattagaccc accccagtgc cagctgatac acaattttga atggatttct   1080
cgttggtttc attgttgtta tcaccttgta ccgcccatac aagtagaaca caatctcttt   1140
tacaaatatg agaactgaga aaagatgta aagcatctca taatacttga ccacagttcc    1200
atcgcttccc tctgatttga taagtcttac tgattcaacc caactattag gaagataaat   1260
tcctgacttt ggaatctcca ccaacaactg taccaccgaa aagtagttga tttgagcatt   1320
gtatgcagag aactcaatga tgactgctcg agtatgatca tcgatccatc gttccgaatc   1380
aagtttattg aagagagtga tgatttccgc ttgggtacca gacatactga tagtatatcc   1440
acctcctgaa tagctataca gtaggcctga aactgtttca gtggataatt cttcagaagt   1500
cttgtaggtg tattcatctg aagcatctgt tccattctcg gattccagtt cggtccaacc   1560
agcttgcatg tacaaagttt tttcttcgtt tctgaaacct ctctattagt tggaaattga   1620
agatttttac tcacttgctt gtcaactcct ctccacaatc attgatgtat ccttgaaact   1680
gcttgaacat cgtacactct gcactttct ttgtccgaac ctgccgtatc gtacctattc    1740
ccatacttct tgaaactta tcattcatgt aggctctcat cccgtatgca ggatttccgt    1800
cgtaccaaga agccaaaaga gcagtggcca gagattcacg agcccaatcc cagaaatcgt   1860
cagcatgttg gattgacatg aaagtattgt caccgtagtt cttttgattg atgttcaaga   1920
ttgtgctcat ctgaaaataa taagttcatc taaatctatg tgcattaaag tctacctcca   1980
actgatacca atatccatgc cggtctttgc aatagtatgt cagcataacc ataatataca   2040
aagaagcaaa gaaacaaagc atatcacgaa tggttataaa taactgttca tctctcattt   2100
ttcggttttc agtgtctcgg agctttgtaa catcagcaat ttcggttccc agaccttttt   2160
cgatttttccc ataggaatt cctgaatttc agtaatgaat tctgatagct tcttttata    2220
aaacttactc aagaacgtct cagctggctt agctcttagc aatgcttcct ccaacttgtt   2280
aatgatttta tgactctttc tggttttcaa aattaaaaac gcccaaatca atcccttaat   2340
tggctcgaac accactgccc atagaatcag actgatcaga aatcggatat agaaagagtt   2400
```

-continued

```
ggctaaatca tccatcaagc tcattccagc tccagaaata taaataagac ccatgagaac    2460
tggaaatact atgatggtac gtgccatccc agccatgaac atcggccatg aaccactatt    2520
atccttgaat tccggatcct ctctctttcg tttttttgtag tagtaatgtt cactgtggga   2580
acgacatttg gtgcataata aaatgtgcaa tgagttgagg aaagtgataa gaacaccgaa    2640
tccaactccg aatgcaatat cttttatagt gaaagtgaac tcggagacac tcttcgaatc   2700
actgataatc gaattatcgc tcttcagaat tgtgatgcta atcatgctga ccacaacaag   2760
tgagaagatg atactgacag aatagtcttg ccttgacact cgatccctca accgattgcc   2820
tccaccagta acatggcaa accaggaaat tgtttgagcc agcatatgca tactcattga    2880
ctcatccaaa accttcgct tatactccac tcgcgctagt cttcagtct ctccgtctcc     2940 gttttagtt ccaagccaat tgttgaaagg gaagtagtag atatcctgag tctgtagatc    3000
tttcacaatt attcgattgc aataccacga ctctcggtga tctagaccag catcgtcaag   3060
ccagagtctc atgtattcca actcgccaag agggctgaaa tattaaattt ggtaaatgat   3120
ttttgatttg aaaacttgaa ttagtccatc aaaaaccaaa acaagttagg gggataaaaa   3180
aaactacacg tccaatctat aattagctca actcacactt gaaccaatca gcgttgtccg   3240
aatttgcata attggttgaa acgtgtgtgg agctaatcgg tattatttat tttaattatt   3300
tttttattgc taaaaatcag cgtcttctaa cttacaatgc cgttgtcatc acaaatcgat   3360
cagtggttcc ccatgaaaac ggaaactccc aattaccatc ttcttctgat ctgaacgatc   3420
ggaaaatctg atccccttca tttccagata aattgaaaca tatcgtacta tccgtagttg   3480
caaacattcg atatccagtc tccacggcaa tcacatacat gtatccatca tgaggctcat   3540
tgtctttcag aaaacgaagt ctcccgcgtg atgcatcttt acgttgacag atgattgcat   3600
tgatggtaag acatccgtaa actactagca tgaaaacagc ggcaatcatc actttcacat   3660
tcttttcgat ttcattcaca ttataattgt aagagaaatc tgcatcaata gttggattga   3720
atgcaccaac agagaacatt gttaaatgat cagttgaaca attaacgaac tgcattcctt   3780
gtccatcact tggatacatt ccttcagaat tgaagacatc cgatgttttc tgatagaagt   3840
aacatccttt actcactgca gcgacttgat aatccattgg tacacttcgt gcaaatgacc   3900
actgcattga atcgtactga ccatagttta caatatccga actatttcca gtgttagtag   3960
agctatttct ttttccaatt ccaataaaga aaagtccagt gttgttgatc aaatttccgg   4020
cggtgacaaa ataattgctt gtcttgttca atgtgttcaa gtcaaagatc cattcatgat   4080
ttgattcaag tgggccagga agactttgga atgatgagaa catgtaggtg tcatcgttgt   4140
ttggaatttc atagtcttga gatgcaataa tctctacttg aagcgagttg ttccagttag   4200
tggttcgaaa agcatgaaga tctaatatct gataactggc aaagtctcct tgttgcatta   4260
aagttagcac tgcatcatcc tcacttcccc tgccgttcac ataaattgga gcagtagttc   4320
cggttattct aaaaacattt taacttatat tggaaaaatt ataggttatt caataaactt   4380
acggaatgat tatctgattc tcatctttga tatgtgcttc aagtgcacct gaggtaatta   4440
acatatcaaa gttatccaca taagttctcg ggtttgtggc atagcaaact aatccaactt   4500
gaatcagtgt tttatctgtg atctcagcag tattcagagt tgaagcgggc gatggaagtt   4560
tgaatgccca ttcttcacag ttttgagttt ttcctacaat atttgatgca tcatcgataa   4620
cgattaccat tccggttccg tcgacgctat tctaaaaatt tgattgacat tagtgtaaac   4680
tgtaactttt tgattaccga gtagtcataa ggtaagttgc cagttgctat agctctagct   4740
gctagcgtgt tttccagggt atctagtgta gatgcaagtt ggttggctag attttttggcc  4800
```

-continued

```
tgaatagaat atgaataatt ccaaactcaa aaagttttaa aaactcacga tgttcttctg      4860
gaacattttt gtgacgtaag cagcccattc ttctgacgtc atttcctcca cgtacacaat      4920
attgtctgga tcacttggta gcacgttgta caaggaatca tagttatctg ttgcatattt      4980
caaattggca gctagatcag aagaaagagg attgtcgaga gcaatcttca acgctgatgt      5040
taaagatccc gcaattgaaa ggagagagtt ggatgtctga aaattattat tatgacatct      5100
accaaagttt agtgtatgaa tacatcatta atctctgcat ctgtcatagt cattccatta      5160
tttgtaagaa aatcttgagt attgctaaga atcgtttcaa tttgttgctg ggattcttga      5220
ttcatcaaac tttgcggcac aatatctgga tatttaaaat gatttgtatg catttgtgta      5280 tttattttt tgagttacca attttagttc ccgaaacatc gccttccgtc gaacttgtc       5340 cattctgaat tacatatcca ttcgttccat ttctaataat caaccctcca tcgattctca      5400
ttttctgtgt gtcagagaat tccattaaag ttctcaaaat taaagttcct atacaaaata      5460
tccattcgag actatactta caccgtatga gtttgagaac cagatgtgta agttccggct      5520
gttatctgaa taccgtaacc tccaagcgcc aaagaaacaa tattgtaggt gggagaactg      5580
atcaccagag ttgtcacaga gtttgacaaa taaagggcgg tggagtctac gaaaaatgag      5640
tagccgctga catcgatgga tgacgctttg gagaagaata gctgcaagaa aagttatttt      5700
gatattaaca actcatcagc aaagtctta cagttcccga aacggtgaca agtgtttgtt        5760
ccttaatcaa tgattgcaaa tcatctttgg tgtacgaagc cgtcggtgaa agagtagata      5820
ttgagacagt ttgagataaa gcagagacag ctggaattcc aatgtcctgc ggagacagca      5880
ccattcgcat tgaataactt cccgcgtttg agaacacaag tggagaagta gtttgattga      5940
ataaagcaag gttgacgtct gaaattttta gcgtcataac cagaccactc ccattgcata      6000
cttactctca ataactatcg gcatctgaat caacttctta accgtgctcg ctgaggatcc      6060
atctgatgcc acaaccgtga agctgtcagc attgtatgag aaaatggcat tatctgtgtc      6120
tacttcaaca aactttcctg ttccattcgt gcaagttatt gtgtaagtaa ctccaccata      6180
tgatgcagtt actactagtc ctctagatac aatattttga gtagaatgca gttttatcat      6240
tgttccagat tcaatctgaa taaaaattga aaaatttcat gtgctctacg atttataaat      6300
ttaccaataa tatgtattga acttctgaga ctgggatatt gaacgaaaat gaagtgttct      6360
tctgacttgt ggatcctact gttgaattgt cataagtgac attccaagca gttacataca      6420
tatcattata actatattcc cctgattgaa catctccaac tccactcatt gtagccatta      6480
tatttccaga aaccagtgat cgtttgtcat ctatttatc ctgctcaact tgcacagtcc        6540 ttccattgt tgcgaacatt ccttggattc cgatggcagc tgctagcata gtgtccgcct       6600
gaacagtttc acataaacta caatgttcta tattcaaaaa gtcttacagt aacggtatct      6660
ccatcaagct gtttataaga tgcccgggta tctcctgtaa ggtatattgt agatccgtaa      6720
atgctgagct gtaagttgaa aacaattaac tctcccaacc atcatttct taccgtacac        6780 ctaggcgata ccaatgtata tcccgatgca ataacatatc aaaaataac cgcgtaagtt        6840 ccatcttttg attttgtact tgatactccc aaggtataga ctgtacttcc tttgagagca      6900
agatcgagag aagacagtac ggagttcaag gattgtgcgg aagtcatatt gacatttgct      6960
agtttagtga taacttttgc catttcgtcg gccaattccg aatttgttgt tgcaatattg      7020
tcttgcaatg ttttcaaaac atcaacactt gacatatttc cgactccagg gattttgagg     7080
gtatttgaga gcaaactttg agcaacttcc actagatctg cggcaggtag agatgagatt      7140
```

```
tgattgagaa gagagctgct tgtgtttaga gagttgttgg atgcagatcc atccattatc      7200
ccagccagtt ggttcattac atcagctttt tgagcatcta tgatcgcttg ttcagctgca      7260
gaaattggag aaactgttgc aagagagctg cgagttttag tagttcttgt agatggttgc      7320
gcggtagcag agaatgcacc atttgcacca gaggaatcgg aagatccaga cgtatcggag      7380
ccagatgagc tcttggttga aacaccagaa gatccatttg aatctgatcc tgagccagat      7440
gtactaccac cgtctcctaa atgggatcct ggtgtggtag ctgttccaga tcctgtacca      7500
tctccattca atgccgttgt ttttccagag tttaccccgt ccgaacccgt ccctgaagac      7560 cccctgacc cacttccaga agcggtcgtt cctgatccac cagcccccga tcccgttgat       7620
gattgtccac ttccagatcc agaagtggtt gatctgactg catcacccgt gctaagagtt      7680
gtcgcagatc ctcctgaacc tgttccacca gttcccccag tagctccagt tccaccggtt      7740
ttgccaccgg catcatccga cgagctgaca gtggttggtg gggtttctaa aaattgaatt      7800
ttatgaaaaa aaaacagtaa tgcgcttacc agtagttgta gttggaagaa ctacattcat      7860
agtaaagatg tgactggcag attctccaga tgcacgattg gtaacattaa ttaagaattc      7920
ataagttcca gttgcaggta caaagctggt cattgggttg aaagatacgg aggcactata      7980
tgcaccattt tttccaactg taatatagta cataaatgaa aattgataac gttgctaact      8040
agggagtgct ctttgtactc catggaaata tgagtcggaa aactacttt cgggtagttt       8100 atgtcatttt ctacacgatt ctgaaagaaa atcctgccgg ttttgggttt tagtgtgaaa      8160
agtttgcgtt tgaaaatacc accctaaatt cagttgattt aacactacgc gacccatatt      8220
tcatgtgcaa cgggaaagcc aagtacactg aaaactcact ttcaaatttt caaagcaaag      8280
tcataatttc ggtggtccag tggataacgg cgggagcggc gccagttttc agtgtacttg      8340
gctttcccgt tgcacatgaa atatgggtcg cgtagtgtta aatcaactga atttagggtg      8400
gtattttcaa acgcaaactt ttcacactaa aacccaaaac cggcaggatt ttctttcaga      8460
atcgtgtaga aaatgatatc aactaccgga aaagtagttt tccgactcat atttccatgg      8520
agtacaaaaa gcactcccta gtaggcaaaa tctcacactc tgtcaagcaa ttgctttcct      8580
tcagtaaaac aaatggctga gaagaatcgt ttcgacattg acaggtcata gcagtcttaa      8640
aatattaagg tttttttaa gtaagattga tttgaatatc ttaccgttaa agctccgggc       8700
tctttgtttg gaattggtgt aatataaaat ggattttcag agtaatacac tgtctcgttc      8760
catgtcaaat tttccaatac aaagtcgtaa ggggtttctg tacttgcgtc tggatccaca      8820
gttgttgttc tcatgctatc agatgcactt gatgaatcgg atggtgtttg agataaacca      8880
gatgaatctg aagtggatgg agttgagtta gatgagtcta tggtggtgga atctgaagtt      8940
gtgccagaat ccgatgttga tgtagaactg tcttgtgaag catcagtcgt gctagcttcc      9000
aaagtcgacg tagattcaat tcctgaagtt gtggaaatgg ctgaactttc ggaagaagat      9060
ccagttgaag ttgtactggt aacttcggat gtacttgttg aatccgcaac aacattcaat      9120
gtgaaaatgt ggctgaccac ttgcattgtc gtcaaatccg tcatgttgat tcgaaactca      9180
taggtgccaa tgccaacaag aaatgtttca attggttgaa ttggaatatt agaagaataa      9240
gttgcgttta ggaccgtgtt tgctggaaat tcgctttaat tcaataattt caaaaagttt      9300
gttaatccta cagtagttta agcaagtgga ttccttaatt ataagaaaag gctcagtaga      9360
cacatttctg cattcaaatg tttggcttct ctaaaatcat tcgtttcatt tggctcaacg      9420
atttattaaa cccgcctcag taggagtaat ggcattagtt ggtaaaggta caatgttgat      9480
gctgtcttca ttgtgacgtg tctcgttcca tgacaatcca ctgtccaaga tgaaatcgaa      9540
```

```
ctgatcgact gacaaagtgg aagttgaatc agcagtggta gaactcggac tggaagaagt   9600
tgtggatgtg tccgagatgg tagttgtact ggaatcagta gtactttctt cggaagttgt   9660
tgtggattct tgtaaagtag ttgtgctccc agccgacgtt gtcgtagaat cgcttgaacg   9720
tgtggatgac ggctctgtga ctgtggatgt tgataatgtg gaagatggag ttgatggtgt   9780
agatgacgta gagcttgcta cagcagatgt agaagattcc gactctatgg tggtggaaga   9840
atattcctga atataaacgt tcgcatacgt gtagtaaact tttttatcgt cggttgtcat   9900
agttgctctg aaggtgtagt ttccaggacc aacgaatgtg ctagcagggt acgtccctcc   9960
gagacgtggc attgatacac tttctgaata tattgaaaaa atatgtgtaa aaaatctaaa  10020
taactatcgc ccgaaaaagg tttgcttttt ttccgatttg aagtttttat agaaacgttt  10080
tcagaattaa agattttgcc tgtctctaat ttataataag tctttataaa caattactcg  10140
tgaaacatgc tccgtcttta gtggttgaaa cataattaga agatgtaggg cttgtacatt  10200
cgatggatgt ttgatactga aatacagtgt tacatttgaa taatgcagtc ttcaatattg  10260
tacttactcc aatgattccg aggccggaat taagcgttag gttcacactt gtggaatcat  10320
agaacgttgt agttgccttt tctacaaaat agaagtctgg attagttccg tccgagctag  10380
tagttgtctc agattttgtt gttgttgaac tttgctgagt agacgtggat gattgagtag  10440
aagaagcggt gcttgacaca gacgaagaag ccgttgaact tggagtggaa gaagaactcg  10500
atggcccagt agttgatgtt gaaggagcag ttgtgctggt tgttactgta gacgaaggag  10560
atgtcgatgt ggactcagtg cttgttgggg tcgttacagt agtcgaggag cttgaactag  10620
atgtcaccgt agaagtcaca ggggatgttg acggggaagt agttacagta ctcgtcgatg  10680
gttcggttgt tgacgttgaa gcagtcgagg tggtcaaagt agtggttggt tcagttgttg  10740
taacagtaga agatgtagat gtaacttctg ttgtggttgt ggaagtagat ggttcttcgg  10800
tagtagtgga tgtcaacata gtggtggtga aagtggtaga cgtagtggtc tcgtcaaggt  10860
aggagcaaat cgcattatcc gggagagacg acaaagttgc tgaaaatttt cgttaaggat  10920
tttctggata actaacaatg cacaacaagg tgatcggtaa tagtgactgc tttgttttac  10980
cctgagcaaa ctgtaattgt ataaaatctg aaatattggc aatacaaacg ggtttgaaga  11040
aaattattaa caattttatt cctgcctctc aatcataaca gcaaattctg gtttgcttgt  11100
aattattatt gtgcgtccga aactcacatg tgatttcggg tgttgtagtg gttggaatac  11160
ttgtactcag tgtggtggag ctcggcgagc ttgtgattgt gctagaactc tgctgagttg  11220
tgctagttga tgatgtcgac gtggatgctg tggaagtgaa cgttgttgac gtggattcga  11280
tggtggtgga tgttgatgga gttgatgtgc ttgtgctcat tgcggtagtc accgtacttg  11340
tacttgttgg gacggttgtt gtagatgtca cggtactagt cacggttgtg gtagttggag  11400
ttgtagtcga ggttgaagtt gactcaatag tgtagtcgca agtattatca ccctggaata  11460
aaatgaaagt aaacactatc tgagaaatcg tactcacagc gtctcgtttc attcttctca  11520
aagtaggtga tccagaagtc ctcatgctaa actgttttgc cctgacaccc ttaagtacct  11580
gcccatcata atacactcct tgactatcac tgatagctgt gctctttca gaacgatctg  11640 aaatactgtt tagccaatgt tcatgagcaa ttaagaactg acaaggtcgc ttgcacattc  11700
ttctcgcata ctcttcgttg atctctccgc tctcacactt ctctcggtag cccagcaacg  11760
ccatctcgtt tccaccgact tggagccacc ataggagcc atcacatctg tcgataccgt  11820
catctgagaa agagtttcta ttaaaatgtt agaaacacat agcactacat atgcaaataa  11880
```

```
cgtttcacca gattcagaat gcgcaattca tgcctatctc atagcctacc tatgtgtcta    11940
cctgagtatc tacttgagta ccttgcaaag aagattaatc ggcacaaacc aagtcaagac    12000
tttgttggca taggtcttcc aggtgagtaa cgccgacatt atacataggt acgcacaaaa    12060
ccttccccaa ataataatcc ttaccataac aaacttcata tttcgcctcc acagcaatac    12120
tgatctcatc gtcatcattc acttcattca agtaatccaa agttgagttc aaaaagagtc    12180
cgacaagcct ggtctctgtt tggatgcagt tgtgaatctg aataggaaca caaggtttt     12240 acaactaaaa aaatacacga ctaaccaatt ccaaacttga acttccgta accttgttct      12300 caactgaaag tctattcaat ccgcagctca atttgatttt aacgactcct tgtgaattcc    12360
ttggaactcc tccaattgtt gtgtcatcgt tgtctaatcg aaaagttgcg atcccgtcaa    12420
gaagttggta atgcaatcca tcaatttgta tcttaaaagt agttttattc agcttttcct    12480
tctgagattt ttcactcacc gccgatattg ccagtagcaa tagaacaaag aagtttgact    12540
tcttcatcca atgagctgga aggttatctt gtagaagttt tgtaaaaatt cgcctgaaaa    12600
caaaaatgaa ttcagagcag aaaagacaac aactgaaaaa tgaagttgtc gaaaagcgaa    12660
aaggcgggct gaatcgaagg accat                                          12685
```

<210> SEQ ID NO 4
<211> LENGTH: 3178
<212> TYPE: PRT
<213> ORGANISM: C. Elegans Lov-1 protein

<400> SEQUENCE: 4

```
Met Val Leu Arg Phe Ser Pro Pro Phe Arg Phe Ser Thr Thr Ser Phe
  1               5                  10                  15

Phe Ser Cys Cys Leu Phe Cys Ser Glu Phe Ile Phe Val Phe Arg Arg
                 20                  25                  30

Ile Phe Thr Lys Leu Leu Gln Asp Asn Leu Pro Ala His Trp Met Lys
             35                  40                  45

Lys Ser Asn Phe Phe Val Leu Leu Leu Ala Ile Ser Ala Ile Gln
         50                  55                  60

Ile Asp Gly Leu His Tyr Gln Leu Leu Asp Gly Ile Ala Thr Phe Arg
 65                  70                  75                  80

Leu Asp Asn Asp Asp Thr Thr Ile Gly Gly Val Pro Arg Asn Ser Gln
                 85                  90                  95

Gly Val Val Lys Ile Lys Leu Ser Cys Gly Leu Asn Arg Leu Ser Val
                100                 105                 110

Glu Asn Lys Val Thr Glu Val Ser Ser Leu Glu Leu Ile His Asn Cys
            115                 120                 125

Ile Gln Thr Glu Thr Arg Leu Val Gly Leu Phe Leu Asn Ser Thr Trp
        130                 135                 140

Ile Thr Leu Asn Glu Val Asn Asp Asp Glu Ile Ser Ile Ala Val
145                 150                 155                 160

Glu Ala Lys Tyr Glu Val Cys Tyr Asp Asp Gly Ile Asp Arg Cys Asp
                165                 170                 175

Gly Ser Leu Trp Trp Leu Gln Val Gly Gly Asn Glu Met Ala Leu Leu
            180                 185                 190

Gly Tyr Arg Glu Lys Cys Glu Ser Gly Glu Ile Asn Glu Glu Tyr Ala
        195                 200                 205

Arg Arg Met Cys Lys Arg Pro Tyr Arg Ser Glu Lys Ser Thr Ala Ile
    210                 215                 220

Ser Asp Ser Gln Gly Val Tyr Tyr Asp Gly Gln Val Leu Lys Gly Val
```

-continued

```
            225                 230                 235                 240
        Arg Ala Lys Gln Phe Ser Met Arg Thr Ser Gly Ser Pro Thr Leu Arg
                        245                 250                 255

Arg Met Lys Arg Asp Ala Gly Asp Asn Thr Cys Asp Tyr Thr Ile Glu
                        260                 265                 270

Ser Thr Ser Thr Ser Thr Thr Thr Pro Thr Thr Thr Val Thr Ser
                    275                 280                 285

Thr Val Thr Ser Thr Thr Val Pro Thr Ser Thr Ser Thr Val Thr
                290                 295                 300

Thr Ala Met Ser Thr Ser Ser Thr Pro Ser Ser Thr Thr Ile
        305                 310                 315                 320

Glu Ser Thr Ser Thr Thr Phe Thr Ser Thr Ala Ser Thr Ser Thr Ser
                        325                 330                 335

Ser Thr Ser Thr Thr Gln Gln Ser Ser Ser Thr Ile Thr Ser Ser Pro
                        340                 345                 350

Ser Ser Thr Thr Leu Ser Thr Ser Ile Pro Thr Thr Thr Pro Glu
                    355                 360                 365

Ile Thr Ser Thr Leu Ser Ser Leu Pro Asp Asn Ala Ile Cys Ser Tyr
                370                 375                 380

Leu Asp Glu Thr Thr Thr Ser Thr Thr Phe Thr Thr Thr Met Leu Thr
        385                 390                 395                 400

Ser Thr Thr Thr Glu Glu Pro Ser Thr Ser Thr Thr Thr Glu Val
                        405                 410                 415

Thr Ser Thr Ser Ser Thr Val Thr Thr Thr Glu Pro Thr Thr Thr Leu
                        420                 425                 430

Thr Thr Ser Thr Ala Ser Thr Ser Thr Thr Glu Pro Ser Thr Ser Thr
                        435                 440                 445

Val Thr Thr Ser Pro Ser Thr Ser Pro Val Thr Ser Thr Val Thr Ser
                450                 455                 460

Ser Ser Ser Ser Ser Thr Thr Val Thr Thr Pro Thr Ser Thr Glu Ser
        465                 470                 475                 480

Thr Ser Thr Ser Pro Ser Ser Thr Val Thr Thr Ser Thr Thr Ala Pro
                        485                 490                 495

Ser Thr Ser Thr Thr Gly Pro Ser Ser Ser Ser Thr Pro Ser Ser
                    500                 505                 510

Thr Ala Ser Ser Ser Val Ser Ser Thr Ala Ser Ser Thr Gln Ser Ser
                    515                 520                 525

Thr Ser Thr Gln Gln Ser Ser Thr Thr Lys Ser Glu Thr Thr Thr
                530                 535                 540

Ser Ser Asp Gly Thr Asn Pro Asp Phe Tyr Phe Val Glu Lys Ala Thr
        545                 550                 555                 560

Thr Thr Phe Tyr Asp Ser Thr Ser Val Asn Leu Thr Leu Asn Ser Gly
                        565                 570                 575

Leu Gly Ile Ile Gly Tyr Gln Thr Ser Ile Glu Cys Thr Ser Pro Thr
                        580                 585                 590

Ser Ser Asn Tyr Val Ser Thr Lys Asp Gly Ala Cys Phe Thr Lys
                    595                 600                 605

Ser Val Ser Met Pro Arg Leu Gly Gly Thr Tyr Pro Ala Ser Thr Phe
                    610                 615                 620

Val Gly Pro Gly Asn Tyr Thr Phe Arg Ala Thr Met Thr Thr Asp Asp
        625                 630                 635                 640

Lys Lys Val Tyr Tyr Thr Tyr Ala Asn Val Tyr Ile Gln Glu Tyr Ser
                        645                 650                 655
```

```
Ser Thr Thr Ile Glu Ser Glu Ser Ser Thr Ser Ala Val Ala Ser Ser
            660                 665                 670

Thr Ser Ser Thr Pro Ser Thr Pro Ser Ser Thr Leu Ser Thr Ser Thr
        675                 680                 685

Val Thr Glu Pro Ser Ser Thr Arg Ser Ser Asp Ser Thr Thr Thr Ser
        690                 695                 700

Ala Gly Ser Thr Thr Thr Leu Gln Glu Ser Thr Thr Thr Ser Glu Glu
705                 710                 715                 720

Ser Thr Thr Asp Ser Ser Thr Thr Thr Ile Ser Asp Thr Ser Thr Ser
                725                 730                 735

Thr Ser Ser Pro Ser Ser Thr Thr Ala Asp Ser Thr Ser Thr Leu Ser
                740                 745                 750

Val Asp Gln Phe Asp Phe Ile Leu Asp Ser Gly Leu Ser Trp Asn Glu
            755                 760                 765

Thr Arg His Asn Glu Asp Ser Ile Asn Ile Val Pro Leu Pro Thr Asn
        770                 775                 780

Ala Ile Thr Pro Thr Glu Arg Ser Gln Thr Phe Glu Cys Arg Asn Val
785                 790                 795                 800

Ser Thr Glu Pro Phe Leu Ile Ile Lys Glu Ser Thr Cys Leu Asn Tyr
                805                 810                 815

Ser Asn Thr Val Leu Asn Ala Thr Tyr Ser Ser Asn Ile Pro Ile Gln
                820                 825                 830

Pro Ile Glu Thr Phe Leu Val Gly Ile Gly Thr Tyr Glu Phe Arg Ile
            835                 840                 845

Asn Met Thr Asp Leu Thr Thr Met Gln Val Val Ser His Ile Phe Thr
        850                 855                 860

Leu Asn Val Val Ala Asp Ser Thr Ser Thr Ser Glu Val Thr Ser Thr
865                 870                 875                 880

Thr Ser Thr Gly Ser Ser Ser Glu Ser Ser Ala Ile Ser Thr Thr Ser
                885                 890                 895

Gly Ile Glu Ser Thr Ser Thr Leu Glu Ala Ser Thr Thr Asp Ala Ser
                900                 905                 910

Gln Asp Ser Ser Thr Ser Thr Ser Asp Ser Gly Thr Thr Ser Asp Ser
            915                 920                 925

Thr Thr Ile Asp Ser Ser Asn Ser Thr Pro Ser Thr Ser Asp Ser Ser
        930                 935                 940

Gly Leu Ser Gln Thr Pro Ser Asp Ser Ser Ala Ser Asp Ser Met
945                 950                 955                 960

Arg Thr Thr Thr Val Asp Pro Asp Ala Ser Thr Glu Thr Pro Tyr Asp
                965                 970                 975

Phe Val Leu Glu Asn Leu Thr Trp Asn Glu Thr Val Tyr Tyr Ser Glu
            980                 985                 990

Asn Pro Phe Tyr Ile Thr Pro Ile Pro Asn Lys Glu Pro Gly Ala Leu
        995                 1000                1005

Thr Thr Ala Met Thr Cys Gln Cys Arg Asn Asp Ser Ser Gln Pro Phe
    1010                1015                1020

Val Leu Leu Lys Glu Ser Asn Cys Leu Thr Glu Phe Gly Lys Asn Gly
1025                1030                1035                1040

Ala Tyr Ser Ala Ser Val Ser Phe Asn Pro Met Thr Ser Phe Val Pro
                1045                1050                1055

Ala Thr Gly Thr Tyr Glu Phe Leu Ile Asn Val Thr Asn Arg Ala Ser
                1060                1065                1070
```

-continued

```
Gly Glu Ser Ala Ser His Ile Phe Thr Met Asn Val Val Leu Pro Thr
        1075                1080                1085

Thr Thr Thr Glu Thr Pro Pro Thr Val Ser Ser Ser Asp Asp Ala
    1090                1095                1100

Gly Gly Lys Thr Gly Gly Thr Gly Ala Thr Gly Gly Thr Gly Gly Thr
1105                1110                1115                1120

Gly Ser Gly Gly Ser Ala Thr Ser Leu Ser Thr Gly Asp Ala Val Arg
            1125                1130                1135

Ser Thr Thr Ser Gly Ser Gly Ser Gly Gln Ser Ser Thr Gly Ser Gly
            1140                1145                1150

Ala Gly Gly Ser Gly Thr Thr Ala Ser Gly Ser Gly Ser Gly Gly Ser
        1155                1160                1165

Ser Gly Thr Gly Ser Asp Gly Val Asn Ser Gly Lys Thr Thr Ala Leu
    1170                1175                1180

Asn Gly Asp Gly Thr Gly Ser Gly Thr Ala Thr Thr Pro Gly Ser His
1185                1190                1195                1200

Leu Gly Asp Gly Gly Ser Thr Ser Gly Ser Gly Ser Asp Ser Asn Gly
            1205                1210                1215

Ser Ser Gly Val Ser Thr Lys Ser Ser Ser Gly Ser Asp Thr Ser Gly
            1220                1225                1230

Ser Ser Asp Ser Ser Gly Ala Asn Gly Ala Phe Ser Ala Thr Ala Gln
            1235                1240                1245

Pro Ser Thr Arg Thr Thr Lys Thr Arg Ser Ser Leu Ala Thr Val Ser
    1250                1255                1260

Pro Ile Ser Ala Ala Glu Gln Ala Ile Ile Asp Ala Gln Lys Ala Asp
1265                1270                1275                1280

Val Met Asn Gln Leu Ala Gly Ile Met Asp Gly Ser Ala Ser Asn Asn
            1285                1290                1295

Ser Leu Asn Thr Ser Ser Ser Leu Leu Asn Gln Ile Ser Ser Leu Pro
            1300                1305                1310

Ala Ala Asp Leu Val Glu Val Ala Gln Ser Leu Leu Ser Asn Thr Leu
            1315                1320                1325

Lys Ile Pro Gly Val Gly Asn Met Ser Ser Val Asp Val Leu Lys Thr
    1330                1335                1340

Leu Gln Asp Asn Ile Ala Thr Thr Asn Ser Glu Leu Ala Asp Glu Met
1345                1350                1355                1360

Ala Lys Val Ile Thr Lys Leu Ala Asn Val Asn Met Thr Ser Ala Gln
            1365                1370                1375

Ser Leu Asn Ser Val Leu Ser Ser Leu Asp Leu Ala Leu Lys Gly Ser
            1380                1385                1390

Thr Val Tyr Thr Leu Gly Val Ser Ser Thr Lys Ser Lys Asp Gly Thr
        1395                1400                1405

Tyr Ala Val Ile Phe Gly Tyr Val Ile Ala Ser Gly Tyr Thr Leu Val
    1410                1415                1420

Ser Pro Arg Cys Thr Leu Ser Ile Tyr Gly Ser Thr Ile Tyr Leu Thr
1425                1430                1435                1440

Gly Asp Thr Arg Ala Ser Tyr Lys Gln Leu Asp Gly Asp Thr Val Thr
            1445                1450                1455

Ala Asp Thr Met Leu Ala Ala Ala Ile Gly Ile Gln Gly Met Phe Ala
            1460                1465                1470

Thr Asn Gly Arg Thr Val Gln Val Glu Gln Asp Lys Ile Asp Asp Lys
        1475                1480                1485

Arg Ser Leu Val Ser Gly Asn Ile Met Ala Thr Met Ser Gly Val Gly
```

-continued

```
            1490                1495                1500

Asp Val Gln Ser Gly Glu Tyr Ser Tyr Asn Asp Met Tyr Val Thr Ala
1505                1510                1515                1520

Trp Asn Val Thr Tyr Asp Asn Ser Thr Val Gly Ser Thr Ser Gln Lys
                1525                1530                1535

Asn Thr Ser Phe Ser Phe Asn Ile Pro Val Ser Glu Val Gln Tyr Ile
            1540                1545                1550

Leu Leu Ile Glu Ser Gly Thr Met Ile Lys Leu His Ser Thr Gln Asn
        1555                1560                1565

Ile Val Ser Arg Gly Leu Val Val Thr Ala Ser Tyr Gly Gly Val Thr
    1570                1575                1580

Tyr Thr Ile Thr Cys Thr Asn Gly Thr Gly Lys Phe Val Glu Val Asp
1585                1590                1595                1600

Thr Asp Asn Ala Ile Phe Ser Tyr Asn Ala Asp Ser Phe Thr Val Val
                1605                1610                1615

Ala Ser Asp Gly Ser Ser Ala Ser Thr Val Lys Lys Leu Ile Gln Met
            1620                1625                1630

Pro Ile Val Ile Glu Asn Val Asn Leu Ala Leu Phe Asn Gln Thr Thr
        1635                1640                1645

Ser Pro Leu Val Phe Ser Asn Ala Gly Ser Tyr Ser Met Arg Met Val
    1650                1655                1660

Leu Ser Pro Gln Asp Ile Gly Ile Pro Ala Val Ser Ala Leu Ser Gln
1665                1670                1675                1680

Thr Val Ser Ile Ser Thr Leu Ser Pro Thr Ala Ser Tyr Thr Lys Asp
                1685                1690                1695

Asp Leu Gln Ser Leu Ile Lys Glu Gln Thr Leu Val Thr Val Ser Gly
            1700                1705                1710

Thr Thr Ser Asn Ser Leu Leu Ser Ile Ala Gly Ser Leu Thr Ser Ala
        1715                1720                1725

Leu Lys Ile Ala Leu Asp Asn Pro Leu Ser Ser Asp Leu Ala Ala Asn
    1730                1735                1740

Leu Lys Tyr Ala Thr Asp Asn Tyr Asp Ser Leu Tyr Asn Val Leu Pro
1745                1750                1755                1760

Ser Asp Pro Asp Asn Ile Val Tyr Val Glu Glu Met Thr Ser Glu Glu
                1765                1770                1775

Trp Ala Ala Tyr Val Thr Lys Met Phe Gln Lys Asn Ile Ala Lys Asn
            1780                1785                1790

Leu Ala Asn Gln Leu Ala Ser Thr Leu Asp Thr Leu Glu Asn Thr Leu
        1795                1800                1805

Ala Ala Arg Ala Ile Ala Thr Gly Asn Leu Pro Tyr Asp Tyr Ser Asn
    1810                1815                1820

Ser Val Asp Gly Thr Gly Met Val Ile Val Ile Asp Asp Ala Ser Asn
1825                1830                1835                1840

Ile Val Gly Lys Thr Gln Asn Cys Glu Glu Trp Ala Phe Lys Leu Pro
                1845                1850                1855

Ser Pro Ala Ser Thr Leu Asn Thr Ala Glu Ile Thr Asp Lys Thr Leu
            1860                1865                1870

Ile Gln Val Gly Leu Val Cys Tyr Ala Thr Asn Pro Arg Thr Tyr Val
        1875                1880                1885

Asp Asn Phe Asp Met Leu Ile Thr Ser Gly Ala Leu Glu Ala His Ile
    1890                1895                1900

Lys Asp Glu Asn Gln Ile Ile Pro Ile Thr Gly Thr Thr Ala Pro
1905                1910                1915                1920
```

US 6,723,557 B1

-continued

```
Ile Tyr Val Asn Gly Arg Gly Ser Glu Asp Asp Ala Val Leu Thr Leu
            1925                1930                1935

Met Gln Gln Gly Asp Phe Ala Ser Tyr Gln Ile Leu Asp Leu His Ala
            1940                1945                1950

Phe Arg Thr Thr Asn Trp Asn Asn Ser Leu Gln Val Glu Ile Ile Ala
            1955                1960                1965

Ser Gln Asp Tyr Glu Ile Pro Asn Asn Asp Thr Tyr Met Phe Ser
1970                1975                1980

Ser Phe Gln Ser Leu Pro Gly Pro Leu Glu Ser Asn His Glu Trp Ile
1985                1990                1995                2000

Phe Asp Leu Asn Thr Leu Asn Lys Thr Ser Asn Tyr Phe Val Thr Ala
            2005                2010                2015

Gly Asn Leu Ile Asn Asn Thr Gly Leu Phe Phe Ile Gly Ile Gly Lys
            2020                2025                2030

Arg Asn Ser Ser Thr Asn Thr Gly Asn Ser Ser Asp Ile Val Asn Tyr
            2035                2040                2045

Gly Gln Tyr Asp Ser Met Gln Trp Ser Phe Ala Arg Ser Val Pro Met
            2050                2055                2060

Asp Tyr Gln Val Ala Ala Val Ser Lys Gly Cys Tyr Phe Tyr Gln Lys
2065                2070                2075                2080

Thr Ser Asp Val Phe Asn Ser Glu Gly Met Tyr Pro Ser Asp Gly Gln
            2085                2090                2095

Gly Met Gln Phe Val Asn Cys Ser Thr Asp His Leu Thr Met Phe Ser
            2100                2105                2110

Val Gly Ala Phe Asn Pro Thr Ile Asp Ala Asp Phe Ser Tyr Asn Tyr
            2115                2120                2125

Asn Val Asn Glu Ile Glu Lys Asn Val Lys Val Met Ile Ala Ala Val
            2130                2135                2140

Phe Met Leu Val Val Tyr Gly Cys Leu Thr Ile Asn Ala Ile Ile Cys
2145                2150                2155                2160

Gln Arg Lys Asp Ala Ser Arg Gly Arg Leu Arg Phe Leu Lys Asp Asn
            2165                2170                2175

Glu Pro His Asp Gly Tyr Met Tyr Val Ile Ala Val Glu Thr Gly Tyr
            2180                2185                2190

Arg Met Phe Ala Thr Thr Asp Ser Thr Ile Cys Phe Asn Leu Ser Gly
            2195                2200                2205

Asn Glu Gly Asp Gln Ile Phe Arg Ser Phe Arg Ser Glu Glu Asp Gly
            2210                2215                2220

Asn Trp Glu Phe Pro Phe Ser Trp Gly Thr Thr Asp Arg Phe Val Met
2225                2230                2235                2240

Thr Thr Ala Phe Pro Leu Gly Glu Leu Glu Tyr Met Arg Leu Trp Leu
            2245                2250                2255

Asp Asp Ala Gly Leu Asp His Arg Glu Ser Trp Tyr Cys Asn Arg Ile
            2260                2265                2270

Ile Val Lys Asp Leu Gln Thr Gln Asp Ile Tyr Tyr Phe Pro Phe Asn
            2275                2280                2285

Asn Trp Leu Gly Thr Lys Asn Gly Asp Gly Glu Thr Glu Arg Leu Ala
            2290                2295                2300

Arg Val Glu Tyr Lys Arg Arg Phe Leu Asp Glu Ser Met Ser Met His
2305                2310                2315                2320

Met Leu Ala Gln Thr Ile Ser Trp Phe Ala Met Phe Thr Gly Gly Gly
            2325                2330                2335
```

-continued

```
Asn Arg Leu Arg Asp Arg Val Ser Arg Gln Asp Tyr Ser Val Ser Ile
            2340                2345                2350
Ile Phe Ser Leu Val Val Ser Met Ile Ser Ile Thr Ile Leu Lys
        2355                2360                2365
Ser Asp Asn Ser Ile Ile Ser Asp Ser Lys Ser Val Ser Glu Phe Thr
2370                2375                2380
Phe Thr Ile Lys Asp Ile Ala Phe Gly Val Gly Phe Gly Val Leu Ile
2385                2390                2395                2400
Thr Phe Leu Asn Ser Leu His Ile Leu Leu Cys Thr Lys Cys Arg Ser
            2405                2410                2415
His Ser Glu His Tyr Tyr Lys Lys Arg Lys Arg Glu Asp Pro Glu
            2420                2425                2430
Phe Lys Asp Asn Ser Gly Ser Trp Pro Met Phe Met Ala Gly Met Ala
            2435                2440                2445
Arg Thr Ile Ile Val Phe Pro Val Leu Met Gly Leu Ile Tyr Ile Ser
            2450                2455                2460
Gly Ala Gly Met Ser Leu Met Asp Asp Leu Ala Asn Ser Phe Tyr Ile
2465                2470                2475                2480
Arg Phe Leu Ile Ser Leu Ile Leu Trp Ala Val Val Phe Glu Pro Ile
            2485                2490                2495
Lys Gly Leu Ile Trp Ala Phe Leu Ile Leu Lys Thr Arg Lys Ser His
            2500                2505                2510
Lys Ile Ile Asn Lys Leu Glu Glu Ala Leu Leu Arg Ala Lys Pro Ala
            2515                2520                2525
Glu Thr Phe Leu Arg Asn Pro Tyr Gly Lys Ile Glu Lys Gly Leu Gly
            2530                2535                2540
Thr Glu Ile Ala Asp Val Thr Lys Leu Arg Asp Thr Glu Asn Arg Lys
2545                2550                2555                2560
Met Arg Asp Glu Gln Leu Phe Ile Thr Ile Arg Asp Met Leu Cys Phe
            2565                2570                2575
Phe Ala Ser Leu Tyr Ile Met Val Met Leu Thr Tyr Tyr Cys Lys Asp
            2580                2585                2590
Arg His Gly Tyr Trp Tyr Gln Leu Glu Met Ser Thr Ile Leu Asn Ile
            2595                2600                2605
Asn Gln Lys Asn Tyr Gly Asp Asn Thr Phe Met Ser Ile Gln His Ala
    2610                2615                2620
Asp Asp Phe Trp Asp Trp Ala Arg Glu Ser Leu Ala Thr Ala Leu Leu
2625                2630                2635                2640
Ala Ser Trp Tyr Asp Gly Asn Pro Ala Tyr Gly Met Arg Ala Tyr Met
            2645                2650                2655
Asn Asp Lys Val Ser Arg Ser Met Gly Ile Gly Thr Ile Arg Gln Val
            2660                2665                2670
Arg Thr Lys Lys Ser Ala Glu Cys Thr Met Phe Lys Gln Phe Gln Gly
            2675                2680                2685
Tyr Ile Asn Asp Cys Gly Glu Glu Leu Thr Ser Lys Asn Glu Glu Lys
    2690                2695                2700
Thr Leu Tyr Met Gln Ala Gly Trp Thr Glu Leu Glu Ser Glu Asn Gly
2705                2710                2715                2720
Thr Asp Ala Ser Asp Glu Tyr Tyr Lys Thr Ser Glu Glu Leu Ser
            2725                2730                2735
Thr Glu Thr Val Ser Gly Leu Leu Tyr Ser Tyr Ser Gly Gly Gly Tyr
            2740                2745                2750
Thr Ile Ser Met Ser Gly Thr Gln Ala Glu Ile Ile Thr Leu Phe Asn
```

-continued

```
             2755                2760                2765

Lys Leu Asp Ser Glu Arg Trp Ile Asp Asp His Thr Arg Ala Val Ile
    2770                2775                2780

Ile Glu Phe Ser Ala Tyr Asn Ala Gln Ile Asn Tyr Phe Ser Val Val
2785                2790                2795                2800

Gln Leu Leu Val Glu Ile Pro Lys Ser Gly Ile Tyr Leu Pro Asn Ser
                2805                2810                2815

Trp Val Glu Ser Val Arg Leu Ile Lys Ser Glu Gly Ser Asp Gly Thr
            2820                2825                2830

Val Val Lys Tyr Tyr Glu Met Leu Tyr Ile Phe Phe Ser Val Leu Ile
        2835                2840                2845

Phe Val Lys Glu Ile Val Phe Tyr Leu Tyr Gly Arg Tyr Lys Val Ile
    2850                2855                2860

Thr Thr Met Lys Pro Thr Arg Asn Pro Phe Lys Ile Val Tyr Gln Leu
2865                2870                2875                2880

Ala Leu Gly Asn Phe Ser Pro Trp Asn Phe Met Asp Leu Ile Val Gly
                2885                2890                2895

Ala Leu Ala Val Ala Ser Val Leu Ala Tyr Thr Ile Arg Gln Arg Thr
            2900                2905                2910

Thr Asn Arg Ala Met Glu Asp Phe Asn Ala Asn Asn Gly Asn Ser Tyr
        2915                2920                2925

Ile Asn Leu Thr Glu Gln Arg Asn Trp Glu Ile Val Phe Ser Tyr Cys
    2930                2935                2940

Leu Ala Gly Ala Val Phe Phe Thr Ser Cys Lys Met Ile Arg Ile Leu
2945                2950                2955                2960

Arg Phe Asn Arg Arg Ile Gly Val Leu Ala Ala Thr Leu Asp Asn Ala
                2965                2970                2975

Leu Gly Ala Ile Val Ser Phe Gly Ile Ala Phe Leu Phe Phe Ser Met
            2980                2985                2990

Thr Phe Asn Ser Val Leu Tyr Ala Val Leu Gly Asn Lys Met Gly Gly
        2995                3000                3005

Tyr Arg Ser Leu Met Ala Thr Phe Gln Thr Ala Leu Ala Gly Met Leu
    3010                3015                3020

Gly Lys Leu Asp Val Thr Ser Ile Gln Pro Ile Ser Gln Phe Ala Phe
3025                3030                3035                3040

Val Val Ile Met Leu Tyr Met Ile Ala Gly Ser Lys Leu Val Leu Gln
                3045                3050                3055

Leu Tyr Val Thr Ile Ile Met Phe Glu Phe Glu Ile Arg Asn Asp
            3060                3065                3070

Ser Glu Lys Gln Thr Asn Asp Tyr Glu Ile Ile Asp His Ile Lys Tyr
        3075                3080                3085

Lys Thr Lys Arg Arg Leu Gly Leu Leu Glu Pro Lys Asp Phe Ala Pro
    3090                3095                3100

Val Ser Ile Ala Asp Thr Gln Lys Asp Phe Arg Leu Phe His Ser Ala
3105                3110                3115                3120

Val Ala Lys Val Asn Leu Leu His His Arg Ala Thr Arg Met Leu Gln
                3125                3130                3135

Thr Gln Gly Gln Tyr Gln Asn Gln Thr Val Ile Asn Tyr Thr Leu Ser
            3140                3145                3150

Tyr Asp Pro Val Ser Ala Ile His Glu Thr Gly Pro Lys Arg Phe Gln
        3155                3160                3165

Lys Trp Arg Leu Asn Asp Val Glu Lys Asp
    3170                3175
```

<210> SEQ ID NO 5
<211> LENGTH: 8073
<212> TYPE: DNA
<213> ORGANISM: C. Elegans pkd-2 gene

<400> SEQUENCE: 5

```
tcattcttct tttttgtcag caatcgaggt gattgttgga cgacgagcgg cagattcacg      60
gttacggact tggttggtga ggagggcctg gacaagtaaa atatttattg gaaatttaga     120
tatttagcag taacagcaaa attatttgta ttttgttgtt taatttacta aatagtaaaa     180
attgtaagtt ttcattaatt cttattgcca gaataaaaaa ttttctaatt ttgttttgtc     240
taatttgtct aaaactacga aagttttct  ctaaaaattt cactagataa atacaatttt     300
tcatgtttca attactttcc aaaagaagta acactataat tgcattagtt acaattttca     360
actcacactc aaatccatca aatttcctcc atcttgttgt tgaactcttt gttttcgat      420
tgtctggagt gttgcattga ctccttcaat ccgatccaca atgctgaaca ctgattcttg     480
catttgatct acacggcggt tcaaactgaa atgatttacg taatgtttat gatcatttat     540
gatagagctg atacagtaaa agttaccaat ttttgtttct attcttcgga attgtgaaaa     600
aatacaattt tctcatggtt ttcattattt gaaaattcca gtcttcacac gtataaactg     660
gaacacgaaa actatgggt  tttattctag aatactaatt ttttaatcga taaataatat     720
tatcgtcaaa aaagcataaa gttttttttg taagatatat gaaaatcgaa taacaaaagt     780
taaacttaat caatttatga aaacattgaa ccagtcaaaa atctaattgt gataccgtga     840
aaaaaaaacg tttccctcca aaagtttacc tttttcaagt cttctgttaa caaattttca     900
gaacgtttat atttgtatgg tgacggtgaa acattatttg atcaaaactg ctgtgggaac     960
tgacggttat tatataatta aggttattat ggtaacagtg aaacagtatt taaaaatagc    1020
tgtttcggta ctcaagggt  atcccatgag gaaaataaaa gtattacttt ttcagttatg    1080
aaaactgaga atgttttcac aaaatgttac ctgtggtctg tttgggaaaa aggaaatcta    1140
cgatgagaaa tttcagaac  attttttgtc aaaattctct acatgttttt ttttgttgta    1200
cgcagcacag cggaagttca ggtggttatg aaagagtaaa tattttttt  ctgtgatata    1260
aaaaatgttt gcctgtcttg acggctgcgg gccagcacat ttgcctacgt ttcaggtaaa    1320
catgattttt gtaattttcc agtggcatgt aggcccgcag gtaggcaggc ctaacaattt    1380
gaccatttaa agttgtgtac acaataaaat attaattctt taaatataa  tcatttgaaa    1440
attgaaatgc gaaccttcgg ttattatcga attgaatgaa aaacaaaaag aaaataattc    1500
taaaaactag ctgaaacatc acaatttcc  gtaaaactca ctttgcgtaa tccctgtgat    1560
tctccatata atttctttc  tgttccgtca ttctagccac ctcatcagca atatcttcag    1620
ccactttctc cggaacatgc tcagtcattg atgttacatt gaatcgagtg aatgcttcat    1680
tgatgtcttt ttcagcgtat ccggcacggt agagcatcag tttgtagtct tcatacgtgg    1740
catcctctcc aggggcatcc gggcgttttc cacgttttgt gagtcctcga actttctgga    1800
atgaggtatt ttgtggtttt agccaagcgc ccgacgtatt tcgggaactc ttagaatatg    1860
gggcgttgat gaaccctgaa gcacccgaca tattccaggt tcaacacaa  acccagaaaa    1920
tgtccgacgc tagtttaggt acaccaagta acttacattc ataaaccaat ccaaaatccc    1980
ctctccatct ttctttctag ccagctctgc tttcacttca acgtaggaat cattgatgat    2040
agccaagaac atgttcaata ggatgaacga gacgaagaag acgtaggcaa tgaagaaggc    2100
```

```
gggtccgaag aatcgattgc aggattctag agccgagaag ttaaagtcac cgagaatgag    2160
acggagcagg gcgaacgcag agttgtagag gttggagtag tcggcgatct tagaaaaatg    2220
tgaagcgccc gacatttacc gggttttgtg taggcaaaac ccggaagatg tcggatgcaa    2280
gaatgtaaca tgccgattag gatacttggt atcactcagt cagataacca ccattttgt    2340 taaaagaaaa tttactgttt cattcaagtt atataagtaa ttggaagatc ccgctgcggt    2400
gaagcgtatt taagattgtt aaaatagctg tgttgatatt tgggtacgtc aaaataaagg    2460
aaatgaatgt tgtaatggat cagacatctg gcgggctcgg tgtaggcaga accaggcaga    2520
tgtcggatgc atgaatgtaa aacgcatccg acatctgccg ggttcttggt tcaaggtaag    2580
cttgataata tttaaaaatg aaaaaaaaac accaggcaga tgtcgggtgc taaaataatt    2640
gctgcgaatt tcccgtttcg taaactttat gagatggaaa tgaatcaaaa tgtcattgta    2700
cctaagaatg cattcgaatg gtagtaaaaa taatgttttt tcatataaaa ttggtgaaac    2760
tgcgattttt ttctaatttt atatttttta aatttcacag caatataaaa cgttacagta    2820
ccccaactat tctaaactcc acgaataaaa caaagatctt aaagattaag ttacctgtgt    2880
cccaaagcac aaatatccaa actgtgcgaa tgcaaaaaag aaaacagcga acatcactgc    2940
aaatcctcca atatcctttg cagatctggt caacgtagag acaactgtg acatggtctt    3000 gttaactgag atgaacttga acactttcac ccaagcaaca aataccacac atgctttgat    3060
gttcagataa gagttctcgg aagaagtgac gtcatcgaat ggtgcatttg tcaatccgtt    3120
ctcaatgaca gagttgacac gatttactcc ggttttttgtg cgattcactg acagaattat    3180
tgtggctact gaaaatccta gcagcacaac gtctaccaaa ttccagaact gggtgagata    3240
gtggagacgg tgacggccga tagcaaaaag ctcctcgaaa atgaagtata gtatgaatcc    3300
acagaagatt ccttcaaaaa tcatcattcg ggtgcctcca gatgtttgat aggtcagaag    3360
atcgtaagtc ataagctttg gagttgtgat aacaccgcca gatgcaggga gctcaaatag    3420
gagtctgaaa tgggaaattt cgaaaaaaat ttaactcgct gcttcagctt tatcataaaa    3480
ttggcgcact tatttgaaaa ttattatctg atcgacattg attggaatgc aaatatttat    3540
aataaatttg ttgacgtaac taaagtttaa aaatccagtt taaaaaaact atgtaaaatt    3600
tcagtactct tgaaactaga caagatttat acttgttttc atttccatag acaccctcac    3660
agttggccgg gtgactgata tgtatggccc gacatttttc gggttactgt ggattcatag    3720
ttttcggtgt ggcccattgc aaggcaaagc tagtgcggcg cgaaactcgg aaaacgtcgg    3780
accatgcata tcagtcaaat gccactcgaa tttcgaaatt tttgaatgaa cgtttactct    3840
tgttgaaata cttataatta cagtttcaca aacattgtaa aattttagtc aaaaacgaga    3900
caccattcca ccaaacatga tagaactcac ttcaccacac aaaacagatt aatattcgca    3960
ttgtacagag caaagtccac aataattgca cgtgatcctc tgtcgatcca gcgattagcc    4020
tttaacgtgg caattgcaga ttgagcttca gttgagccag ctactggaag gcgttgaaca    4080
aatccaccac ctccatatga agcaatggtg cccacggttt tcaggttttc aagctctttt    4140
gccgtggcgt agatgaatct gaatataata ttttatttaa aaaaggatt ggtgagactg    4200 ttttttatag gaattatatg ttgacaataa ctatctaaga ctaacaatta aatgaaaatt    4260
gcatgacaac cataatgttc taaaatttaa aaaaggagc atgaaacatt acgaatatta    4320
gttagaatat ttcaattttc gaggtacttt tcacaaactt tacatttttt tcaacgtttt    4380
ttaataagaa tactctttca ggtagttaat atataagcta aattttgcat ttgtgtattg    4440
aagcttttgc aaaaacacat aaacagatat aactgataat ttcttggaac ataaaattgt    4500
```

```
attttcatgc aaatttcgta acattctttc aaatacagtt tcataatatt gttaaaaaga    4560
aattggggtt ttctcaatag tccataaaat tctaaatatt tttaaaataa aactaagtat    4620
tttccgcaaa taagtcaagt tttgcaataa aatttactgt ttcacattat gatcaagttt    4680
gcatcacaat aagaaataat agtaaaaatt ggttctccat gaaaaaaccc cataaatgcc    4740
atgaaacaac gttagctccg cctttcacca atcgccgatt ggtcagcaga attcaaaagg    4800
tactagaagc tgctgattca acgaccaaac ttggccgaat ttacaaaatt gacgtcactc    4860
acgcatcaac acttccatca ccgaccatcg tcttatcctc gagcttttcc tcataatttg    4920
caaaacattc cttaatctcc cgctggaaac ttttcatcac agtacacgag tcatttgtca    4980
ctttcaacat tctgatccga ggttccccaa gcaaacgatt ctcatagtag atcatattct    5040
cgttatccgt cgaattggaa gtttccgtcc aatatatgcc aggtattagg acttgtgaca    5100
gccactgaaa gtttgatttg aaggttttca tttaaaaatt gaggaaactt catcccaaa     5160 tattatccat tgaggtacaa gatccaaatg ctggagctcc ggaggcaccg gtgctcgcca    5220
caaacaggtc gctcattact ttggagtagt agtaagattg gatgctgttt tgggcgaacg    5280
caactgtaaa tttttgaatt tagaaaaaaa aaacccgtga agtgtcgggt gctaactggg    5340
cgtgctcgat atatcacagg attagcccga ctacctgcga ggtgtcgcgc gaaacactag    5400
atgaaaattt tacaagaaaa tgattttcga aaatacaaac atttgttaac attaattgta    5460
tttttaagtt gtaaacgcaa aaataaatat tggaaatttg aaaatgtttt gttacaaaaa    5520
ttctgctgtt ttgcttacta agtaaaccta acaaattata ggtaaaaata gtatgtgaac    5580
gtttcatgag gttattcaag tagtgtcgga aaattaaaaa gtgtagaaaa attacgtcac    5640
aactgtatta aaatacataa aaacatgtat tttaatacat ttgtgacgtc acaaatgtat    5700
ttaaatacat tttgctacat tacttgatta accccattaa caaagttgta ctcgtaaaat    5760
ttcagttgaa atgctcaaac tcactaaacg tgttgaggaa aaaaaataaa aatttaaaaa    5820
aaaactgttc caccgttgta acaaatgttg tacgcgtttg tcttaaatag tattcggagg    5880
attcagcctg caatggacag ttttcaaaag agaaaaattt aactaattgg aagccattta    5940
atcaaaaatt atgaatttag agattacttt gaaaatgta tgattctaaa cgtttctttt      6000
gtgtttattt gcaaaattca aatataagtt tttccacttt tcaaaaccta tttataaaaa    6060
ttagaaaatt aaacaatttt ccaaacaaca tttttcccg tactgcatta aagtaacaac      6120
ataaattgga agattagtaa ctactttggt catagtgttt ccaacaaagt gtggttttta    6180
tgatgctcac aataaatttt tcgaatgcca gttgaaacat ttttgaaaaa ttataaaaca    6240
cgaaatgaat attttgcagt tgatagttac aaatccctgc caaatctttt ttttcacaaa    6300
cttgaatttt aagaaatttg ctaaaaaaaa acttcggctg tttcatacat gccatataat    6360
ttgtaaaaat aaagtgaaaa tcgattcgtc gtgtgtagtt tcgccactca ctataaaatt    6420
gctgattaag tatagtgagt ggcgaaactc ggaaattgtc ggccgccgtg gaaacctacc    6480
ccaaaaccgg acgcagtgcg tccggtggtg ttaaaatcgg acgaccggac gccgatttgt    6540
acagccctat ttgaaagtaa tgacgtcata cttactttca tacagaaatt aaatatctga    6600
tacgttagat tttgggaaat aagcttgtca caaaaaatga tgtggtttat ttctagaagt    6660
cttactatgt agttggtaca caaaatatga aatttgtagc gtatgcttca tagcagttac    6720
aaagtcgaga actatttgta cattaatttg accaacaaac ttaccataaa ccagcacaat    6780
caagaacaca gcgtatccac caacttccat aaacgaacgg gcagtcagct tgatctttcc    6840
```

-continued

```
atccgatttc tcgtgtccgg atgccagcaa ggcttgagaa aacgagattc cctcttttg      6900 agccggattc ttcttcttat cgtgctcata ctcctcactg accatagaat ggtcaaacga      6960
ggggccatgc tccgcagcgg cgaccggctg cggtggatta gcccatcgct cgtccgcagc      7020
gccgtagttc attgaagacg gctcgctgaa acagtagaaa atttgaatta agttttgag       7080 aaaagttgaa atcgagagc tctgtagtgt aaaaactgga aaaatagagt cgaaaagagg       7140
cgagctcgcg aaatccacgt cctcgtagct cttggagatg ccgcattgct aagagatttc      7200
cgtagatact atgttttatg ggatttcacg ttttggttg gagacggttt tttgcataga      7260
aacggaaaaa tgatgcagga atagaaaacg aacatgattt gaaactgaaa accatcgact      7320
atacggcaca atcatactac atttatcggg ttattgaaac tgcatcccaa aagtttacaa      7380
tttaaattca cataccatt gaagataaca acgaataaaa agacttcgaa aggcggcaaa       7440
tgtcgtggtt tcgtggtgta gtggttatca catctgtcta acacacagaa ggtcggtggt      7500
tcgagcccgc ccgagatcat aagtttttg tcaatcatta atattgattc atctgaatga       7560
aattgtaaaa ttcttgaag gtgttctaaa atattgaact gttttttttt agatttcgtt       7620
agtatataat ttttgaaaca tacatttttt tcttccaaat ttcaagtatc ttctacgatt      7680
tttgaaaaat cccaaaaatt gtaaacatta aaattctgaa taaacggtgg aaatttgtag      7740
ttctctcaaa ttctaaataa aaattgaacg aaatttgaga aatttcctgt ttcaaaaact      7800
aaatgtctta ttttcagagt tcaacaatgc cttagagaaa gttggaaaat gataatgttt      7860
gttagtatat tgagaatatc atgcaagtga acaattagt tttttttcg ataacaatta        7920 tttaaaaaaa actactgttt caaatctttt attcaaccaa tcctgtaata aaagttcact      7980
tatcttctcc ctcttcatcc ataatgtatg cccctcttca aatggaaaat atgatgtcgg      8040
ggggaggtcc tccccctccc cacgaccctc cat                                    8073
```

<210> SEQ ID NO 6
<211> LENGTH: 815
<212> TYPE: PRT
<213> ORGANISM: C. Elegans Pkd-2 protein

<400> SEQUENCE: 6

```
Met Glu Gly Arg Gly Glu Gly Glu Asp Leu Pro Pro Thr Ser Tyr Phe
  1               5                  10                  15

Pro Phe Glu Glu Gly His Thr Leu Trp Met Lys Arg Glu Lys Ile Lys
                 20                  25                  30

His Leu Gln Arg Ile Leu Gln Phe His Ser Asp Glu Ser Ile Leu Met
             35                  40                  45

Ile Asp Lys Lys Leu Met Ile Ser Gly Leu Glu Pro Pro Thr Phe
         50                  55                  60

Cys Val Leu Asp Arg Cys Asp Asn His Tyr Thr Thr Lys Pro Arg His
 65                  70                  75                  80

Leu Pro Pro Phe Glu Val Phe Leu Phe Val Ile Phe Lys Cys Glu
                 85                  90                  95

Pro Ser Ser Met Asn Tyr Gly Ala Ala Asp Glu Arg Trp Ala Asn Pro
            100                 105                 110

Pro Gln Pro Val Ala Ala Ala Glu His Gly Pro Ser Phe Asp His Ser
        115                 120                 125

Met Val Ser Glu Glu Tyr Glu His Asp Lys Lys Asn Pro Ala Gln
    130                 135                 140

Lys Glu Gly Ile Ser Phe Ser Gln Ala Leu Leu Ala Ser Gly His Glu
145                 150                 155                 160
```

-continued

```
Lys Ser Asp Gly Lys Ile Lys Leu Thr Ala Arg Ser Phe Met Glu Val
            165                 170                 175
Gly Gly Tyr Ala Val Phe Leu Ile Val Leu Val Tyr Val Ala Phe Ala
            180                 185                 190
Gln Asn Ser Ile Gln Ser Tyr Tyr Ser Lys Val Met Ser Asp Leu
            195                 200                 205
Phe Val Ala Ser Thr Gly Ala Ser Gly Ala Pro Ala Phe Gly Ser Cys
            210                 215                 220
Thr Ser Met Asp Asn Ile Trp Asp Trp Leu Ser Gln Val Leu Ile Pro
225                 230                 235                 240
Gly Ile Tyr Trp Thr Glu Thr Ser Asn Ser Thr Asp Asn Glu Asn Met
                245                 250                 255
Ile Tyr Tyr Glu Asn Arg Leu Leu Gly Glu Pro Arg Ile Arg Met Leu
                260                 265                 270
Lys Val Thr Asn Asp Ser Cys Thr Val Met Lys Ser Phe Gln Arg Glu
                275                 280                 285
Ile Lys Glu Cys Phe Ala Asn Tyr Glu Glu Lys Leu Glu Asp Lys Thr
            290                 295                 300
Met Val Gly Asp Gly Ser Val Asp Ala Phe Ile Tyr Ala Thr Ala Lys
305                 310                 315                 320
Glu Leu Glu Asn Leu Lys Thr Val Gly Thr Ile Ala Ser Tyr Gly Gly
                325                 330                 335
Gly Gly Phe Val Gln Arg Leu Pro Val Ala Gly Ser Thr Glu Ala Gln
                340                 345                 350
Ser Ala Ile Ala Thr Leu Lys Ala Asn Arg Trp Ile Asp Arg Gly Ser
                355                 360                 365
Arg Ala Ile Ile Val Asp Phe Ala Leu Tyr Asn Ala Asn Ile Asn Leu
            370                 375                 380
Phe Cys Val Val Lys Leu Leu Phe Glu Leu Pro Ala Ser Gly Gly Val
385                 390                 395                 400
Ile Thr Thr Pro Lys Leu Met Thr Tyr Asp Leu Leu Thr Tyr Gln Thr
                405                 410                 415
Ser Gly Gly Thr Arg Met Met Ile Phe Glu Gly Ile Phe Cys Gly Phe
                420                 425                 430
Ile Leu Tyr Phe Ile Phe Glu Glu Leu Phe Ala Ile Gly Arg His Arg
            435                 440                 445
Leu His Tyr Leu Thr Gln Phe Trp Asn Leu Val Asp Val Val Leu Leu
            450                 455                 460
Gly Phe Ser Val Ala Thr Ile Ile Leu Ser Val Asn Arg Thr Lys Thr
465                 470                 475                 480
Gly Val Asn Arg Val Asn Ser Val Ile Glu Asn Gly Leu Thr Asn Ala
                485                 490                 495
Pro Phe Asp Asp Val Thr Ser Ser Glu Asn Ser Tyr Leu Asn Ile Lys
                500                 505                 510
Ala Cys Val Val Phe Val Ala Trp Val Lys Val Phe Lys Phe Ile Ser
            515                 520                 525
Val Asn Lys Thr Met Ser Gln Leu Ser Ser Thr Leu Thr Arg Ser Ala
            530                 535                 540
Lys Asp Ile Gly Gly Phe Ala Val Met Phe Ala Val Phe Phe Phe Ala
545                 550                 555                 560
Phe Ala Gln Phe Gly Tyr Leu Cys Phe Gly Thr Gln Ile Ala Asp Tyr
                565                 570                 575
```

```
Ser Asn Leu Tyr Asn Ser Ala Phe Ala Leu Leu Arg Leu Ile Leu Gly
            580                 585                 590

Asp Phe Asn Phe Ser Ala Leu Glu Ser Cys Asn Arg Phe Phe Gly Pro
        595                 600                 605

Ala Phe Phe Ile Ala Tyr Val Phe Val Ser Phe Ile Leu Leu Asn
    610                 615                 620

Met Phe Leu Ala Ile Ile Asn Asp Ser Tyr Val Glu Val Lys Ala Glu
625                 630                 635                 640

Leu Ala Arg Lys Lys Asp Gly Glu Gly Ile Leu Asp Trp Phe Met Asn
                645                 650                 655

Lys Val Arg Gly Leu Thr Lys Arg Gly Lys Arg Pro Asp Ala Pro Gly
                660                 665                 670

Glu Asp Ala Thr Tyr Glu Asp Tyr Lys Leu Met Leu Tyr Arg Ala Gly
            675                 680                 685

Tyr Ala Glu Lys Asp Ile Asn Glu Ala Phe Thr Arg Phe Asn Val Thr
    690                 695                 700

Ser Met Thr Glu His Val Pro Glu Lys Val Ala Glu Asp Ile Ala Asp
705                 710                 715                 720

Glu Val Ala Arg Met Thr Glu Gln Lys Arg Asn Tyr Met Glu Asn His
                725                 730                 735

Arg Asp Tyr Ala Asn Leu Asn Arg Val Asp Gln Met Gln Glu Ser
            740                 745                 750

Val Phe Ser Ile Val Asp Arg Ile Glu Gly Val Asn Ala Thr Leu Gln
        755                 760                 765

Thr Ile Glu Lys Gln Arg Val Gln Gln Gln Asp Gly Gly Asn Leu Met
    770                 775                 780

Asp Leu Ser Ala Leu Leu Thr Asn Gln Val Arg Asn Arg Glu Ser Ala
785                 790                 795                 800

Ala Arg Arg Pro Thr Ile Thr Ser Ile Ala Asp Lys Lys Glu Glu
                805                 810                 815

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Outside
      primer for PCR screening oflov-1 genomic (sy582) deletion

<400> SEQUENCE: 7
ctctatttgt ggttcgttgg cg                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Outside
      primer for PCR screening oflov-1 genomic (sy582) deletion

<400> SEQUENCE: 8
gggagtttcc gttttcatgg gg                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Nested
      primer for PCR screening oflov-1 genomic (sy582) deletion
```

<400> SEQUENCE: 9
ctaggaccga tgcaacagcg ag                                    22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Nested
      primer for PCR screening oflov-1 genomic (sy582) deletion

<400> SEQUENCE: 10
aacgctgatt ggttcaagtg tg                                    22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Outside
      primer for PCR screening ofpkd-2 genomic (sy606) deletion

<400> SEQUENCE: 11
cccctcgttt gaccattcta tgg                                   23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Outside
      primer for PCR screening ofpkd-2 genomic (sy606) deletion

<400> SEQUENCE: 12
acgtgatcct ctgtcgatcc ag                                    22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Nested
      primer for PCR screening ofpkd-2 genomic (sy606) deletion

<400> SEQUENCE: 13
agatcaagct gactgcccgt tc                                    22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Nested
      primer for PCR screening ofpkd-2 genomic (sy606) deletion

<400> SEQUENCE: 14
gatccagcga ttagccttta acg                                   23

<210> SEQ ID NO 15
<211> LENGTH: 2870
<212> TYPE: PRT
<213> ORGANISM: C. Elegans Lov-1 sy582 deletion protein

<400> SEQUENCE: 15

Met Val Leu Arg Phe Ser Pro Pro Phe Arg Phe Ser Thr Thr Ser Phe

```
  1               5                  10                 15
Phe Ser Cys Cys Leu Phe Cys Ser Glu Phe Ile Phe Val Phe Arg Arg
            20                  25                 30

Ile Phe Thr Lys Leu Leu Gln Asp Asn Leu Pro Ala His Trp Met Lys
            35                  40                 45

Lys Ser Asn Phe Phe Val Leu Leu Leu Ala Ile Ser Ala Ile Gln
     50                  55                  60

Ile Asp Gly Leu His Tyr Gln Leu Leu Asp Gly Ile Ala Thr Phe Arg
65                  70                  75                  80

Leu Asp Asn Asp Asp Thr Thr Ile Gly Gly Val Pro Arg Asn Ser Gln
                85                  90                  95

Gly Val Val Lys Ile Lys Leu Ser Cys Gly Leu Asn Arg Leu Ser Val
            100                 105                110

Glu Asn Lys Val Thr Glu Val Ser Ser Leu Glu Leu Ile His Asn Cys
            115                 120                 125

Ile Gln Thr Glu Thr Arg Leu Val Gly Leu Phe Leu Asn Ser Thr Trp
            130                 135                 140

Ile Thr Leu Asn Glu Val Asn Asp Asp Glu Ile Ser Ile Ala Val
145                 150                 155                 160

Glu Ala Lys Tyr Glu Val Cys Tyr Asp Asp Gly Ile Asp Arg Cys Asp
                165                 170                 175

Gly Ser Leu Trp Trp Leu Gln Val Gly Gly Asn Glu Met Ala Leu Leu
                180                 185                 190

Gly Tyr Arg Glu Lys Cys Glu Ser Gly Glu Ile Asn Glu Glu Tyr Ala
            195                 200                 205

Arg Arg Met Cys Lys Arg Pro Tyr Arg Ser Glu Lys Ser Thr Ala Ile
210                 215                 220

Ser Asp Ser Gln Gly Val Tyr Tyr Asp Gly Gln Val Leu Lys Gly Val
225                 230                 235                 240

Arg Ala Lys Gln Phe Ser Met Arg Thr Ser Gly Ser Pro Thr Leu Arg
                245                 250                 255

Arg Met Lys Arg Asp Ala Gly Asp Asn Thr Cys Asp Tyr Thr Ile Glu
            260                 265                 270

Ser Thr Ser Thr Ser Thr Thr Thr Pro Thr Thr Thr Thr Val Thr Ser
            275                 280                 285

Thr Val Thr Ser Thr Thr Thr Val Pro Thr Ser Thr Ser Thr Val Thr
    290                 295                 300

Thr Ala Met Ser Thr Ser Ser Thr Pro Ser Ser Thr Thr Ile
305                 310                 315                 320

Glu Ser Thr Ser Thr Thr Phe Thr Ser Thr Ala Ser Thr Ser Thr Ser
                325                 330                 335

Ser Thr Ser Thr Thr Gln Gln Ser Ser Ser Thr Ile Thr Ser Ser Pro
            340                 345                 350

Ser Ser Thr Thr Leu Ser Thr Ser Ile Pro Thr Thr Thr Pro Glu
            355                 360                 365

Ile Thr Ser Thr Leu Ser Ser Leu Pro Asp Asn Ala Ile Cys Ser Tyr
    370                 375                 380

Leu Asp Glu Thr Thr Thr Ser Thr Thr Phe Thr Thr Met Leu Thr
385                 390                 395                 400

Ser Thr Thr Thr Glu Glu Pro Ser Thr Thr Thr Thr Glu Val
                405                 410                 415

Thr Ser Thr Ser Ser Thr Val Thr Thr Thr Glu Pro Thr Thr Thr Leu
            420                 425                 430
```

```
Thr Thr Ser Thr Ala Ser Thr Ser Thr Thr Glu Pro Ser Thr Ser Thr
            435                 440                 445

Val Thr Thr Ser Pro Ser Thr Ser Pro Val Thr Ser Thr Val Thr Ser
450                 455                 460

Ser Ser Ser Ser Ser Thr Thr Val Thr Thr Pro Thr Ser Thr Glu Ser
465                 470                 475                 480

Thr Ser Thr Ser Pro Ser Ser Thr Val Thr Thr Ser Thr Thr Ala Pro
                485                 490                 495

Ser Thr Ser Thr Thr Gly Pro Ser Ser Ser Ser Thr Pro Ser Ser
            500                 505                 510

Thr Ala Ser Ser Ser Val Ser Ser Thr Ala Ser Ser Thr Gln Ser Ser
            515                 520                 525

Thr Ser Thr Gln Gln Ser Ser Thr Thr Thr Lys Ser Glu Thr Thr Thr
            530                 535                 540

Ser Ser Asp Gly Thr Asn Pro Asp Phe Tyr Phe Val Glu Lys Ala Thr
545                 550                 555                 560

Thr Thr Phe Tyr Asp Ser Thr Ser Val Asn Leu Thr Leu Asn Ser Gly
                565                 570                 575

Leu Gly Ile Ile Gly Tyr Gln Thr Ser Ile Glu Cys Thr Ser Pro Thr
                580                 585                 590

Ser Ser Asn Tyr Val Ser Thr Thr Lys Asp Gly Ala Cys Phe Thr Lys
            595                 600                 605

Ser Val Ser Met Pro Arg Leu Gly Gly Thr Tyr Pro Ala Ser Thr Phe
            610                 615                 620

Val Gly Pro Gly Asn Tyr Thr Phe Arg Ala Thr Met Thr Thr Asp Asp
625                 630                 635                 640

Lys Lys Val Tyr Tyr Thr Tyr Ala Asn Val Tyr Ile Gln Glu Tyr Ser
                645                 650                 655

Ser Thr Thr Ile Glu Ser Glu Ser Ser Thr Ser Ala Val Ala Ser Ser
            660                 665                 670

Thr Ser Ser Thr Pro Ser Thr Pro Ser Ser Thr Leu Ser Thr Ser Thr
            675                 680                 685

Val Thr Glu Pro Ser Ser Thr Arg Ser Ser Asp Ser Thr Thr Thr Ser
690                 695                 700

Ala Gly Ser Thr Thr Thr Leu Gln Glu Ser Thr Thr Thr Ser Glu Glu
705                 710                 715                 720

Ser Thr Thr Asp Ser Ser Thr Thr Thr Ile Ser Asp Thr Ser Thr Ser
                725                 730                 735

Thr Ser Ser Pro Ser Ser Thr Thr Ala Asp Ser Thr Ser Thr Leu Ser
                740                 745                 750

Val Asp Gln Phe Asp Phe Ile Leu Asp Ser Gly Leu Ser Trp Asn Glu
            755                 760                 765

Thr Arg His Asn Glu Asp Ser Ile Asn Ile Val Pro Leu Pro Thr Asn
            770                 775                 780

Ala Ile Thr Pro Thr Glu Arg Ser Gln Thr Phe Glu Cys Arg Asn Val
785                 790                 795                 800

Ser Thr Glu Pro Phe Leu Ile Ile Lys Glu Ser Thr Cys Leu Asn Tyr
                805                 810                 815

Ser Asn Thr Val Leu Asn Ala Thr Tyr Ser Ser Asn Ile Pro Ile Gln
            820                 825                 830

Pro Ile Glu Thr Phe Leu Val Gly Ile Gly Thr Tyr Glu Phe Arg Ile
            835                 840                 845
```

-continued

```
Asn Met Thr Asp Leu Thr Thr Met Gln Val Ser His Ile Phe Thr
    850                 855                 860
Leu Asn Val Val Ala Asp Ser Thr Ser Thr Ser Glu Val Thr Ser Thr
865                 870                 875                 880
Thr Ser Thr Gly Ser Ser Ser Glu Ser Ser Ala Ile Ser Thr Thr Ser
                885                 890                 895
Gly Ile Glu Ser Thr Ser Thr Leu Glu Ala Ser Thr Thr Asp Ala Ser
            900                 905                 910
Gln Asp Ser Ser Thr Ser Thr Ser Asp Ser Gly Thr Thr Ser Asp Ser
            915                 920                 925
Thr Thr Ile Asp Ser Ser Asn Ser Thr Pro Ser Thr Ser Asp Ser Ser
    930                 935                 940
Gly Leu Ser Gln Thr Pro Ser Asp Ser Ser Ser Ala Ser Asp Ser Met
945                 950                 955                 960
Arg Thr Thr Thr Val Asp Pro Asp Ala Ser Thr Glu Thr Pro Tyr Asp
                965                 970                 975
Phe Val Leu Glu Asn Leu Thr Trp Asn Glu Thr Val Tyr Tyr Ser Glu
            980                 985                 990
Asn Pro Phe Tyr Ile Thr Pro Ile Pro Asn Lys Glu Pro Gly Ala Leu
            995                 1000                1005
Thr Thr Ala Met Thr Cys Gln Cys Arg Asn Asp Ser Ser Gln Pro Phe
    1010                1015                1020
Val Leu Leu Lys Glu Ser Asn Cys Leu Thr Glu Phe Gly Lys Asn Gly
1025                1030                1035                1040
Ala Tyr Ser Ala Ser Val Ser Phe Asn Pro Met Thr Ser Phe Val Pro
                1045                1050                1055
Ala Thr Gly Thr Tyr Glu Phe Leu Ile Asn Val Thr Asn Arg Ala Ser
                1060                1065                1070
Gly Glu Ser Ala Ser His Ile Phe Thr Met Asn Val Val Leu Pro Thr
            1075                1080                1085
Thr Thr Thr Glu Thr Pro Pro Thr Thr Val Ser Ser Ser Asp Asp Ala
    1090                1095                1100
Gly Gly Lys Thr Gly Gly Thr Gly Ala Thr Gly Gly Thr Gly Gly Thr
1105                1110                1115                1120
Gly Ser Gly Gly Ser Ala Thr Thr Leu Ser Thr Gly Asp Ala Val Arg
                1125                1130                1135
Ser Thr Thr Ser Gly Ser Gly Ser Gly Gln Ser Ser Thr Gly Ser Gly
                1140                1145                1150
Ala Gly Gly Ser Gly Thr Thr Ala Ser Gly Ser Gly Ser Gly Gly Ser
            1155                1160                1165
Ser Gly Thr Gly Ser Asp Gly Val Asn Ser Gly Lys Thr Thr Ala Leu
    1170                1175                1180
Asn Gly Asp Gly Thr Gly Ser Gly Thr Ala Thr Thr Pro Gly Ser His
1185                1190                1195                1200
Leu Gly Asp Gly Gly Ser Thr Ser Gly Ser Gly Ser Asp Ser Asn Gly
                1205                1210                1215
Ser Ser Gly Val Ser Thr Lys Ser Ser Ser Gly Ser Asp Thr Ser Gly
            1220                1225                1230
Ser Ser Asp Ser Ser Gly Ala Asn Gly Ala Phe Ser Ala Thr Ala Gln
            1235                1240                1245
Pro Ser Thr Arg Thr Thr Lys Thr Arg Ser Ser Leu Ala Thr Val Ser
    1250                1255                1260
Pro Ile Ser Ala Ala Glu Gln Ala Ile Ile Asp Ala Gln Lys Ala Asp
```

-continued

```
              1265                1270                1275                1280
Val Met Asn Gln Leu Ala Gly Ile Met Asp Gly Ser Ala Ser Asn Asn
                    1285                1290                1295
Ser Leu Asn Thr Ser Ser Ser Leu Leu Asn Gln Ile Ser Ser Leu Pro
                1300                1305                1310
Ala Ala Asp Leu Val Glu Val Ala Gln Ser Leu Leu Ser Asn Thr Leu
            1315                1320                1325
Lys Ile Pro Gly Val Gly Asn Met Ser Ser Val Asp Val Leu Lys Thr
        1330                1335                1340
Leu Gln Asp Asn Ile Ala Thr Thr Asn Ser Glu Leu Ala Asp Glu Met
1345                1350                1355                1360
Ala Lys Val Ile Thr Lys Leu Ala Asn Val Asn Met Thr Ser Ala Gln
                1365                1370                1375
Ser Leu Asn Ser Val Leu Ser Ser Leu Asp Leu Ala Leu Lys Gly Ser
            1380                1385                1390
Thr Val Tyr Thr Leu Gly Val Ser Ser Thr Lys Ser Lys Asp Gly Thr
        1395                1400                1405
Tyr Ala Val Ile Phe Gly Tyr Val Ile Ala Ser Gly Tyr Thr Leu Val
    1410                1415                1420
Ser Pro Arg Cys Thr Leu Ser Ile Tyr Gly Ser Thr Ile Tyr Leu Thr
1425                1430                1435                1440
Gly Asp Thr Arg Ala Ser Tyr Lys Gln Leu Asp Gly Asp Thr Val Thr
                1445                1450                1455
Ala Asp Thr Met Leu Ala Ala Ala Ile Gly Ile Gln Gly Met Phe Ala
            1460                1465                1470
Thr Asn Gly Arg Thr Val Gln Val Glu Gln Asp Lys Ile Asp Asp Lys
        1475                1480                1485
Arg Ser Leu Val Ser Gly Asn Ile Met Ala Thr Met Ser Gly Val Gly
    1490                1495                1500
Asp Val Gln Ser Gly Glu Tyr Ser Tyr Asn Asp Met Tyr Val Thr Ala
1505                1510                1515                1520
Trp Asn Val Thr Tyr Asp Asn Ser Thr Val Gly Ser Thr Ser Gln Lys
                1525                1530                1535
Asn Thr Ser Phe Ser Phe Asn Ile Pro Val Ser Glu Val Gln Tyr Ile
            1540                1545                1550
Leu Leu Ile Glu Ser Gly Thr Met Ile Lys Leu His Ser Thr Gln Asn
        1555                1560                1565
Ile Val Ser Arg Gly Leu Val Val Thr Ala Ser Tyr Gly Gly Val Thr
    1570                1575                1580
Tyr Thr Ile Thr Cys Thr Asn Gly Thr Gly Lys Phe Val Glu Val Asp
1585                1590                1595                1600
Thr Asp Asn Ala Ile Phe Ser Tyr Asn Ala Asp Ser Phe Thr Val Val
                1605                1610                1615
Ala Ser Asp Gly Ser Ser Ala Ser Thr Val Lys Lys Leu Ile Gln Met
            1620                1625                1630
Pro Ile Val Ile Glu Asn Val Asn Leu Ala Leu Phe Asn Gln Thr Thr
        1635                1640                1645
Ser Pro Leu Val Phe Ser Asn Ala Gly Ser Tyr Ser Met Arg Met Val
    1650                1655                1660
Leu Ser Pro Gln Asp Ile Gly Ile Pro Ala Val Ser Ala Leu Ser Gln
1665                1670                1675                1680
Thr Val Ser Ile Ser Thr Leu Ser Pro Thr Ala Ser Tyr Thr Lys Asp
                1685                1690                1695
```

-continued

```
Asp Leu Gln Ser Leu Ile Lys Glu Gln Thr Leu Val Thr Val Ser Gly
        1700                1705                1710

Thr Thr Ser Asn Ser Leu Leu Ser Ile Ala Gly Ser Leu Thr Ser Ala
        1715                1720                1725

Leu Lys Ile Ala Leu Asp Asn Pro Leu Ser Ser Asp Leu Ala Ala Asn
        1730                1735                1740

Leu Lys Tyr Ala Thr Asp Asn Tyr Asp Ser Leu Tyr Asn Val Leu Pro
1745                1750                1755                1760

Ser Asp Pro Asp Asn Ile Val Tyr Val Glu Glu Met Thr Ser Glu Glu
            1765                1770                1775

Trp Ala Ala Tyr Val Thr Lys Met Phe Gln Lys Asn Ile Ala Lys Asn
            1780                1785                1790

Leu Ala Asn Gln Leu Ala Ser Thr Leu Asp Thr Leu Glu Asn Thr Leu
            1795                1800                1805

Ala Ala Arg Ala Ile Ala Thr Gly Asn Leu Pro Tyr Asp Tyr Ser Asn
            1810                1815                1820

Ser Val Asp Gly Thr Gly Met Val Ile Val Ile Asp Asp Ala Ser Asn
1825                1830                1835                1840

Ile Val Gly Lys Thr Gln Asn Cys Glu Glu Trp Ala Phe Lys Leu Pro
            1845                1850                1855

Ser Pro Ala Ser Thr Leu Asn Thr Ala Glu Ile Thr Asp Lys Thr Leu
            1860                1865                1870

Ile Gln Val Gly Leu Val Cys Tyr Ala Thr Asn Pro Arg Thr Tyr Val
            1875                1880                1885

Asp Asn Phe Asp Met Leu Ile Thr Ser Gly Ala Leu Glu Ala His Ile
            1890                1895                1900

Lys Asp Glu Asn Gln Ile Ile Pro Ile Thr Gly Thr Thr Ala Pro
1905                1910                1915                1920

Ile Tyr Val Asn Gly Arg Gly Ser Glu Asp Asp Ala Val Leu Thr Leu
            1925                1930                1935

Met Gln Gln Gly Asp Phe Ala Ser Tyr Gln Ile Leu Asp Leu His Ala
            1940                1945                1950

Phe Arg Thr Thr Asn Trp Asn Asn Ser Leu Gln Val Glu Ile Ile Ala
            1955                1960                1965

Ser Gln Asp Tyr Glu Ile Pro Asn Asn Asp Asp Thr Tyr Met Phe Ser
        1970                1975                1980

Ser Phe Gln Ser Leu Pro Gly Pro Leu Glu Ser Asn His Glu Trp Ile
1985                1990                1995                2000

Phe Asp Leu Asn Thr Leu Asn Lys Thr Ser Asn Tyr Phe Val Thr Ala
            2005                2010                2015

Gly Asn Leu Ile Asn Asn Thr Gly Leu Phe Phe Ile Gly Ile Gly Lys
            2020                2025                2030

Arg Asn Ser Ser Thr Asn Thr Gly Asn Ser Ser Asp Ile Val Asn Tyr
        2035                2040                2045

Gly Gln Tyr Asp Ser Met Gln Trp Ser Phe Ala Arg Ser Val Pro Met
    2050                2055                2060

Asp Tyr Gln Val Ala Ala Val Ser Lys Gly Cys Tyr Phe Tyr Gln Lys
2065                2070                2075                2080

Thr Ser Asp Val Phe Asn Ser Glu Gly Met Tyr Pro Ser Asp Gly Gln
            2085                2090                2095

Gly Met Gln Phe Val Asn Cys Ser Thr Asp His Leu Thr Met Phe Ser
            2100                2105                2110
```

-continued

```
Val Gly Ala Phe Asn Pro Thr Ile Asp Ala Asp Phe Ser Tyr Asn Tyr
        2115                2120                2125

Asn Val Asn Glu Ile Glu Lys Asn Val Lys Val Met Ile Ala Ala Val
        2130                2135                2140

Phe Met Leu Val Val Tyr Gly Cys Leu Thr Ile Asn Ala Ile Ile Cys
2145                2150                2155                2160

Gln Arg Lys Asp Ala Ser Arg Gly Arg Leu Arg Phe Leu Lys Asp Asn
        2165                2170                2175

Glu Pro His Asp Gly Tyr Met Tyr Val Ile Ala Val Glu Thr Gly Tyr
        2180                2185                2190

Arg Met Phe Ala Thr Thr Asp Ser Thr Ile Cys Phe Asn Leu Ser Gly
        2195                2200                2205

Asn Glu Gly Asp Gln Ile Phe Arg Ser Phe Arg Ser Glu Glu Asp Gly
        2210                2215                2220

Asn Trp Glu Phe Pro Phe Ser Trp Gly Thr Thr Asp Arg Phe Val Met
2225                2230                2235                2240

Thr Thr Ala Phe Pro Leu Gly Glu Leu Glu Tyr Met Arg Leu Trp Leu
        2245                2250                2255

Asp Asp Ala Gly Leu Asp His Arg Glu Ser Trp Tyr Cys Asn Arg Ile
        2260                2265                2270

Ile Val Lys Asp Leu Gln Thr Gln Asp Ile Tyr Tyr Phe Pro Phe Asn
        2275                2280                2285

Asn Trp Leu Gly Thr Lys Asn Gly Asp Gly Glu Thr Glu Arg Leu Ala
        2290                2295                2300

Arg Val Glu Tyr Lys Arg Arg Phe Leu Asp Glu Ser Met Ser Met His
2305                2310                2315                2320

Met Leu Ala Gln Thr Ile Ser Trp Phe Ala Met Phe Thr Gly Gly Gly
        2325                2330                2335

Asn Arg Leu Arg Asp Arg Val Ser Arg Gln Asp Tyr Ser Val Ser Ile
        2340                2345                2350

Ile Phe Ser Leu Val Val Ser Met Ile Ser Ile Thr Ile Leu Lys
        2355                2360                2365

Ser Asp Asn Ser Ile Ile Ser Asp Ser Lys Ser Val Ser Glu Phe Thr
        2370                2375                2380

Phe Thr Ile Lys Asp Ile Ala Phe Gly Val Gly Phe Gly Val Leu Ile
2385                2390                2395                2400

Thr Phe Leu Asn Ser Leu His Ile Leu Leu Cys Thr Lys Cys Arg Ser
        2405                2410                2415

His Ser Glu His Tyr Tyr Tyr Lys Lys Arg Lys Arg Glu Asp Pro Glu
        2420                2425                2430

Phe Lys Asp Asn Ser Gly Ser Trp Pro Met Phe Met Ala Gly Met Ala
        2435                2440                2445

Arg Thr Ile Ile Val Phe Pro Val Leu Met Gly Leu Ile Tyr Ile Ser
        2450                2455                2460

Gly Ala Gly Met Ser Leu Met Asp Asp Leu Ala Asn Ser Phe Tyr Ile
2465                2470                2475                2480

Arg Phe Leu Ile Ser Leu Ile Leu Trp Ala Val Val Phe Glu Pro Ile
        2485                2490                2495

Lys Gly Leu Ile Trp Ala Phe Leu Ile Leu Lys Thr Arg Lys Ser His
        2500                2505                2510

Lys Ile Ile Asn Lys Leu Glu Gly Ser Asp Gly Thr Val Val Lys Tyr
        2515                2520                2525

Tyr Glu Met Leu Tyr Ile Phe Phe Ser Val Leu Ile Phe Val Lys Glu
```

2530              2535              2540
Ile Val Phe Tyr Leu Tyr Gly Arg Tyr Lys Val Ile Thr Thr Met Lys
2545              2550              2555              2560

Pro Thr Arg Asn Pro Phe Lys Ile Val Tyr Gln Leu Ala Leu Gly Asn
                2565              2570              2575

Phe Ser Pro Trp Asn Phe Met Asp Leu Ile Val Gly Ala Leu Ala Val
            2580              2585              2590

Ala Ser Val Leu Ala Tyr Thr Ile Arg Gln Arg Thr Thr Asn Arg Ala
        2595              2600              2605

Met Glu Asp Phe Asn Ala Asn Asn Gly Asn Ser Tyr Ile Asn Leu Thr
    2610              2615              2620

Glu Gln Arg Asn Trp Glu Ile Val Phe Ser Tyr Cys Leu Ala Gly Ala
2625              2630              2635              2640

Val Phe Phe Thr Ser Cys Lys Met Ile Arg Ile Leu Arg Phe Asn Arg
                2645              2650              2655

Arg Ile Gly Val Leu Ala Ala Thr Leu Asp Asn Ala Leu Gly Ala Ile
            2660              2665              2670

Val Ser Phe Gly Ile Ala Phe Leu Phe Ser Met Thr Phe Asn Ser
        2675              2680              2685

Val Leu Tyr Ala Val Leu Gly Asn Lys Met Gly Gly Tyr Arg Ser Leu
    2690              2695              2700

Met Ala Thr Phe Gln Thr Ala Leu Ala Gly Met Leu Gly Lys Leu Asp
2705              2710              2715              2720

Val Thr Ser Ile Gln Pro Ile Ser Gln Phe Ala Phe Val Val Ile Met
                2725              2730              2735

Leu Tyr Met Ile Ala Gly Ser Lys Leu Val Leu Gln Leu Tyr Val Thr
            2740              2745              2750

Ile Ile Met Phe Glu Phe Glu Glu Ile Arg Asn Asp Ser Glu Lys Gln
        2755              2760              2765

Thr Asn Asp Tyr Glu Ile Ile Asp His Ile Lys Tyr Lys Thr Lys Arg
    2770              2775              2780

Arg Leu Gly Leu Leu Glu Pro Lys Asp Phe Ala Pro Val Ser Ile Ala
2785              2790              2795              2800

Asp Thr Gln Lys Asp Phe Arg Leu Phe His Ser Ala Val Ala Lys Val
                2805              2810              2815

Asn Leu Leu His His Arg Ala Thr Arg Met Leu Gln Thr Gln Gly Gln
            2820              2825              2830

Tyr Gln Asn Gln Thr Val Ile Asn Tyr Thr Leu Ser Tyr Asp Pro Val
        2835              2840              2845

Ser Ala Ile His Glu Thr Gly Pro Lys Arg Phe Gln Lys Trp Arg Leu
    2850              2855              2860

Asn Asp Val Glu Lys Asp
2865              2870

<210> SEQ ID NO 16
<211> LENGTH: 200
<212> TYPE: PRT
<213> ORGANISM: C. Elegans Pkd-2 deletion mutant (sy606) protein

<400> SEQUENCE: 16

Met Glu Gly Arg Gly Glu Gly Glu Asp Leu Pro Pro Thr Ser Tyr Phe
 1               5                  10                  15

Pro Phe Glu Glu Gly His Thr Leu Trp Met Lys Arg Glu Lys Ile Lys
            20                  25                  30

-continued

```
His Leu Gln Arg Ile Leu Gln Phe His Ser Asp Glu Ser Ile Leu Met
         35                  40                  45

Ile Asp Lys Lys Leu Met Ile Ser Gly Gly Leu Glu Pro Pro Thr Phe
         50                  55                  60

Cys Val Leu Asp Arg Cys Asp Asn His Tyr Thr Thr Lys Pro Arg His
 65              70                  75                      80

Leu Pro Pro Phe Glu Val Phe Leu Phe Val Val Ile Phe Lys Cys Glu
                 85                  90                  95

Pro Ser Ser Met Asn Tyr Gly Ala Ala Asp Glu Arg Trp Ala Asn Pro
             100                 105                 110

Pro Gln Pro Val Ala Ala Glu His Gly Pro Ser Phe Asp His Ser
         115                 120                 125

Met Val Ser Glu Glu Tyr Glu His Asp Lys Lys Lys Asn Pro Ala Gln
         130                 135                 140

Lys Glu Gly Ile Ser Phe Ser Gln Ala Leu Leu Ala Ser Gly His Glu
145                 150                 155                 160

Lys Ser Asp Gly Lys Ile Lys Leu Thr Ala Arg Ser Phe Met Glu Val
             165                 170                 175

Gly Gly Tyr Ala Val Phe Leu Ile Val Leu Val Tyr Asp Ser Ser Thr
             180                 185                 190

Pro Arg Gln Lys Ser Leu Lys Thr
         195                 200
```